US011058478B2

(12) United States Patent
Walberg et al.

(10) Patent No.: US 11,058,478 B2
(45) Date of Patent: Jul. 13, 2021

(54) LAPAROSCOPIC RADIOFREQUENCY SURGICAL DEVICE

(71) Applicant: Aesculap AG, Tuttlingen (DE)

(72) Inventors: Erik Walberg, Redwood City, CA (US); Brandon Loudermilk, San Francisco (CA)

(73) Assignee: AESCULAP AG, Tuttlingen (DE)

(*) Notice: Subject to any disclaimer, the term of this patent is extended or adjusted under 35 U.S.C. 154(b) by 549 days.

(21) Appl. No.: 15/905,005

(22) Filed: Feb. 26, 2018

(65) Prior Publication Data
US 2018/0185087 A1   Jul. 5, 2018

Related U.S. Application Data

(63) Continuation of application No. 13/021,633, filed on Feb. 4, 2011, now Pat. No. 9,918,778, which is a (Continued)

(51) Int. Cl.
*A61B 18/14* (2006.01)
*A61B 17/29* (2006.01)
(Continued)

(52) U.S. Cl.
CPC .. *A61B 18/1445* (2013.01); *A61B 2017/2932* (2013.01); *A61B 2018/0063* (2013.01);
(Continued)

(58) Field of Classification Search
CPC .......... A61B 17/295; A61B 2018/2934; A61B 2018/2933; A61B 18/1442;
(Continued)

(56) References Cited

U.S. PATENT DOCUMENTS

| 1,918,700 A | 7/1931 | Harris |
|---|---|---|
| 3,356,408 A | 12/1967 | Stutz |

(Continued)

FOREIGN PATENT DOCUMENTS

| CA | 2061215 A1 | 8/1992 |
|---|---|---|
| CA | 2237423 A1 | 11/1998 |

(Continued)

OTHER PUBLICATIONS

Nojarov et al., "High-Energy Scissors Mode", Phys. Rev. C. Nucl. Phys., vol. 51, No. 5, 1995—pp. 2449-2456.
(Continued)

*Primary Examiner* — Ronald Hupczey, Jr.

(57) ABSTRACT

Embodiments of the disclosed technology relate to a bipolar electrosurgical device for a laparoscopic environment, as well as methods for the use of such a device. Embodiments of the device may include a set of opposing jaws comprising at least one bipolar electrode pair disposed thereon, the set of jaws configured to deliver radiofrequency energy to a target tissue. Embodiments of the set of jaws, when closed, may have a diameter no greater than about 5 mm. The device may further include a shaft with a diameter that may be no greater than about 5 mm. Each of the jaws has a tissue-facing surface of each jaw that may include a complementary self-aligning configuration with respect to the longitudinal axis of the other jaw. Embodiments of the device may further include a pinless rotation assembly formed from rotatably cooperative features of the first jaw and the second jaw that connect the jaws together and enable the jaw set to pivot between an open position and a closed position.

25 Claims, 33 Drawing Sheets

Related U.S. Application Data continuation-in-part of application No. 11/743,579, filed on May 2, 2007, now Pat. No. 8,574,229, which is a continuation-in-part of application No. 11/382,652, filed on May 10, 2006, now Pat. No. 7,942,874.

(60) Provisional application No. 61/301,295, filed on Feb. 4, 2010, provisional application No. 60/746,256, filed on May 2, 2006.

(51) Int. Cl.
*A61B 18/00* (2006.01)
*A61B 90/00* (2016.01)

(52) U.S. Cl.
CPC .......... *A61B 2018/00505* (2013.01); *A61B 2018/00589* (2013.01); *A61B 2018/00595* (2013.01); *A61B 2018/00601* (2013.01); *A61B 2018/00678* (2013.01); *A61B 2018/00702* (2013.01); *A61B 2018/00791* (2013.01); *A61B 2018/00827* (2013.01); *A61B 2018/00875* (2013.01); *A61B 2018/1412* (2013.01); *A61B 2018/1455* (2013.01); *A61B 2090/064* (2016.02)

(58) Field of Classification Search
CPC .......... A61B 18/1445; A61B 18/1447; A61B 2018/1452; A61B 2018/1455
See application file for complete search history.

(56) References Cited

U.S. PATENT DOCUMENTS

| | | |
|---|---|---|
| 3,527,224 A | 9/1970 | Rabinowitz |
| 3,709,215 A | 1/1973 | Richmond |
| 3,742,955 A | 7/1973 | Battista et al. |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai et al. |
| 4,041,952 A | 8/1977 | Morrison et al. |
| 4,072,153 A | 2/1978 | Swartz |
| 4,094,320 A | 6/1978 | Newton et al. |
| 4,231,372 A | 11/1980 | Newton |
| 4,492,231 A | 1/1985 | Auth |
| 4,532,924 A | 8/1985 | Auth et al. |
| 4,590,934 A | 5/1986 | Malis et al. |
| 4,644,953 A | 2/1987 | Lahodny et al. |
| 4,671,274 A | 6/1987 | Sorochenko |
| 4,972,846 A | 11/1990 | Owens et al. |
| 4,976,717 A | 12/1990 | Boyle |
| 4,979,948 A | 12/1990 | Gedes et al. |
| 4,998,527 A | 3/1991 | Meyer |
| 5,037,379 A | 8/1991 | Clayman et al. |
| 5,041,101 A | 8/1991 | Seder et al. |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang et al. |
| 5,151,102 A | 9/1992 | Kamiyama et al. |
| 5,156,603 A | 10/1992 | Olsen |
| 5,156,613 A | 10/1992 | Sawyer |
| 5,178,618 A | 1/1993 | Kandarpa |
| 5,190,541 A | 3/1993 | Abele et al. |
| 5,207,691 A | 5/1993 | Nardella |
| 5,217,030 A | 6/1993 | Yoon |
| 5,234,425 A | 8/1993 | Fogarty et al. |
| 5,250,074 A | 10/1993 | Wilk et al. |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox et al. |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,068 A | 4/1994 | Rosar et al. |
| 5,300,087 A | 4/1994 | Knoepfler |
| 5,312,023 A | 5/1994 | Green et al. |
| 5,324,289 A | 6/1994 | Eggers |
| 5,330,471 A | 7/1994 | Eggers |
| 5,330,502 A | 7/1994 | Hassler et al. |
| 5,336,229 A | 8/1994 | Noda |
| 5,336,237 A | 8/1994 | Chin et al. |
| 5,341,807 A | 8/1994 | Nardella |
| 5,342,381 A | 8/1994 | Tidemand |
| 5,352,223 A | 10/1994 | McBrayer et al. |
| 5,352,235 A | 10/1994 | Koros et al. |
| 5,354,336 A | 10/1994 | Kelman et al. |
| 5,356,408 A | 10/1994 | Rydell |
| 5,366,477 A * | 11/1994 | LeMarie, III .......... A61B 17/29 606/208 |
| 5,374,277 A | 12/1994 | Hasslet |
| 5,377,415 A | 1/1995 | Gibson |
| 5,391,166 A | 2/1995 | Eggers |
| 5,395,369 A | 3/1995 | McBrayer et al. |
| 5,395,375 A * | 3/1995 | Turkel .......... A61B 17/1608 606/174 |
| 5,396,900 A | 3/1995 | Slater et al. |
| 5,397,320 A | 3/1995 | Essig et al. |
| 5,403,312 A | 4/1995 | Yates et al. |
| 5,417,687 A | 5/1995 | Nardella et al. |
| 5,423,814 A | 6/1995 | Zhu et al. |
| 5,431,676 A | 7/1995 | Dubrul et al. |
| 5,438,302 A | 8/1995 | Goble |
| 5,443,463 A | 8/1995 | Stern et al. |
| 5,443,470 A | 8/1995 | Stern et al. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,462,546 A | 10/1995 | Rydell |
| 5,472,442 A | 12/1995 | Klicek |
| 5,480,399 A | 1/1996 | Hebbron |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,520,698 A | 5/1996 | Koh |
| 5,531,744 A | 7/1996 | Nardella et al. |
| 5,540,684 A | 7/1996 | Hassler |
| 5,540,685 A | 7/1996 | Parins et al. |
| 5,542,945 A | 8/1996 | Fritzsch |
| 5,549,637 A | 8/1996 | Crainich |
| 5,556,397 A | 9/1996 | Long et al. |
| 5,558,100 A | 9/1996 | Cox |
| 5,558,671 A | 9/1996 | Yates |
| 5,562,700 A | 10/1996 | Huitema et al. |
| 5,562,701 A | 10/1996 | Huitema et al. |
| 5,562,702 A | 10/1996 | Huitema et al. |
| 5,562,720 A | 10/1996 | Stern et al. |
| 5,569,243 A | 10/1996 | Kortenbach et al. |
| 5,571,100 A | 11/1996 | Goble et al. |
| 5,573,535 A | 11/1996 | Viklund |
| 5,578,052 A | 11/1996 | Koros et al. |
| 5,599,350 A | 2/1997 | Schulze et al. |
| 5,601,224 A | 2/1997 | Bishop et al. |
| 5,603,700 A | 2/1997 | Daneshvar |
| 5,603,711 A | 2/1997 | Parins et al. |
| 5,611,803 A | 3/1997 | Heaven et al. |
| 5,624,452 A | 4/1997 | Yates et al. |
| 5,637,110 A | 6/1997 | Pennybacker et al. |
| 5,637,111 A | 6/1997 | Sutcu et al. |
| 5,653,692 A | 8/1997 | Masterson et al. |
| 5,658,281 A | 8/1997 | Heard |
| 5,662,662 A | 9/1997 | Bishop et al. |
| 5,662,676 A | 9/1997 | Koninckx |
| 5,665,085 A | 9/1997 | Nardella |
| 5,665,100 A | 9/1997 | Yoon |

(56) References Cited

U.S. PATENT DOCUMENTS

| | | |
|---|---|---|
| 5,667,526 A | 9/1997 | Levin |
| 5,669,907 A | 9/1997 | Platt et al. |
| 5,673,840 A | 10/1997 | Schulze et al. |
| 5,673,841 A | 10/1997 | Schulze et al. |
| 5,674,220 A | 10/1997 | Fox et al. |
| 5,675,184 A | 10/1997 | Kei et al. |
| 5,680,983 A | 10/1997 | Plyley et al. |
| 5,681,282 A | 10/1997 | Eggers et al. |
| 5,683,385 A | 11/1997 | Kortenbach et al. |
| 5,683,388 A | 11/1997 | Slater |
| 5,688,270 A | 11/1997 | Yates et al. |
| 5,693,051 A | 12/1997 | Schulze et al. |
| 5,697,949 A | 12/1997 | Giurtino et al. |
| 5,700,261 A | 12/1997 | Brinkerhoff |
| 5,702,390 A | 12/1997 | Austin et al. |
| 5,704,534 A | 1/1998 | Huitema et al. |
| 5,707,369 A | 1/1998 | Vaitekunas et al. |
| 5,709,680 A | 1/1998 | Yates et al. |
| 5,713,896 A | 2/1998 | Nardella |
| 5,715,832 A | 2/1998 | Koblish et al. |
| 5,718,703 A | 2/1998 | Chin |
| 5,720,719 A | 2/1998 | Edwards et al. |
| 5,728,143 A | 3/1998 | Gough et al. |
| 5,733,283 A | 3/1998 | Malis et al. |
| 5,735,289 A | 4/1998 | Pfeffer et al. |
| 5,735,848 A | 4/1998 | Yates et al. |
| 5,735,849 A | 4/1998 | Baden et al. |
| 5,741,285 A | 4/1998 | McBrayer et al. |
| 5,746,750 A | 5/1998 | Prestel et al. |
| 5,749,895 A | 5/1998 | Sawyer et al. |
| 5,755,717 A | 5/1998 | Yates et al. |
| 5,776,130 A | 7/1998 | Buysse et al. |
| 5,788,662 A | 8/1998 | Antanavich et al. |
| 5,797,941 A | 8/1998 | Schulze et al. |
| 5,810,811 A | 9/1998 | Yates et al. |
| 5,817,091 A | 10/1998 | Nardella et al. |
| 5,817,092 A | 10/1998 | Behl |
| 5,823,066 A | 10/1998 | Huitema et al. |
| 5,833,689 A | 11/1998 | Long et al. |
| 5,836,990 A | 11/1998 | Li |
| 5,840,077 A | 11/1998 | Rowden et al. |
| 5,855,576 A | 1/1999 | LeVeen et al. |
| 5,860,975 A | 1/1999 | Goble et al. |
| 5,891,142 A | 4/1999 | Eggers et al. |
| 5,893,835 A | 4/1999 | Witt et al. |
| 5,893,874 A | 4/1999 | Bourque et al. |
| 5,931,835 A | 8/1999 | Mackey |
| 5,931,836 A | 8/1999 | Hatta et al. |
| 5,954,720 A | 9/1999 | Wilson et al. |
| 5,967,128 A | 10/1999 | Onushi et al. |
| 5,979,453 A | 11/1999 | Savage et al. |
| 6,003,517 A | 12/1999 | Sheffield et al. |
| 6,004,319 A | 12/1999 | Goble et al. |
| 6,030,384 A | 2/2000 | Nezhat |
| 6,050,993 A | 4/2000 | Tu et al. |
| 6,050,995 A | 4/2000 | Durgin |
| 6,056,744 A | 5/2000 | Edwards |
| 6,059,766 A | 5/2000 | Greff |
| 6,059,782 A | 5/2000 | Novak et al. |
| 6,066,139 A | 5/2000 | Ryan et al. |
| 6,068,626 A | 5/2000 | Harrington et al. |
| 6,071,281 A | 6/2000 | Burnside et al. |
| 6,074,386 A | 6/2000 | Goble et al. |
| 6,086,586 A | 7/2000 | Hooven |
| 6,090,106 A | 7/2000 | Goble et al. |
| 6,093,186 A | 7/2000 | Goble |
| 6,096,037 A | 8/2000 | Mulier et al. |
| 6,099,550 A | 8/2000 | Yoon |
| 6,123,701 A | 9/2000 | Nezhat |
| H1904 H | 10/2000 | Yates et al. |
| 6,142,992 A | 11/2000 | Cheng et al. |
| 6,152,920 A | 11/2000 | Thompson et al. |
| 6,152,932 A | 11/2000 | Ternström |
| 6,162,220 A | 12/2000 | Nezhat |
| 6,174,309 B1 | 1/2001 | Wrublewski et al. |
| 6,179,832 B1 | 1/2001 | Jones et al. |
| 6,197,026 B1 | 3/2001 | Farin et al. |
| 6,203,541 B1 | 3/2001 | Keppel |
| 6,203,542 B1 | 3/2001 | Ellsberry et al. |
| 6,206,877 B1 | 3/2001 | Kese et al. |
| 6,210,406 B1 | 4/2001 | Webster |
| 6,212,426 B1 | 4/2001 | Swanson |
| 6,217,894 B1 | 4/2001 | Sawhney et al. |
| 6,228,084 B1 | 5/2001 | Kirwan |
| 6,234,178 B1 | 5/2001 | Goble et al. |
| 6,241,139 B1 | 6/2001 | Milliman et al. |
| 6,245,069 B1 | 6/2001 | Gminder |
| 6,254,601 B1 | 7/2001 | Burbank et al. |
| 6,258,085 B1 | 7/2001 | Eggleston |
| 6,277,114 B1 | 8/2001 | Bullivant et al. |
| 6,283,963 B1 | 9/2001 | Regula |
| 6,287,304 B1 | 9/2001 | Eggers et al. |
| 6,290,715 B1 | 9/2001 | Sharkey et al. |
| 6,293,942 B1 | 9/2001 | Goble et al. |
| 6,293,946 B1 | 9/2001 | Thorne |
| 6,296,636 B1 | 10/2001 | Cheng et al. |
| 6,312,430 B1 | 11/2001 | Wilson et al. |
| 6,322,494 B1 | 11/2001 | Bullivant et al. |
| 6,327,505 B1 | 12/2001 | Medhkour et al. |
| 6,334,861 B1 | 1/2002 | Chandler et al. |
| 6,350,274 B1 | 2/2002 | Li |
| 6,361,559 B1 | 3/2002 | Houser et al. |
| 6,364,879 B1 | 4/2002 | Chen et al. |
| 6,371,956 B1 | 4/2002 | Wilson et al. |
| 6,391,024 B1 | 5/2002 | Sun et al. |
| 6,391,029 B1 | 5/2002 | Hooven et al. |
| 6,398,779 B1 | 6/2002 | Buysse et al. |
| 6,398,781 B1 | 6/2002 | Goble et al. |
| H2037 H | 7/2002 | Yates et al. |
| 6,416,509 B1 | 7/2002 | Goble et al. |
| 6,428,550 B1 | 8/2002 | Vargas et al. |
| 6,436,096 B1 | 8/2002 | Hareyama |
| 6,464,702 B2 | 10/2002 | Schulze et al. |
| 6,485,486 B1 | 11/2002 | Trembly et al. |
| 6,485,489 B2 | 11/2002 | Teirstein et al. |
| 6,491,690 B1 | 12/2002 | Goble et al. |
| 6,494,881 B1 | 12/2002 | Bales et al. |
| 6,500,176 B1 | 12/2002 | Truckai et al. |
| 6,514,252 B2 | 2/2003 | Nezhat et al. |
| 6,517,530 B1 | 2/2003 | Klevin |
| 6,520,185 B1 | 2/2003 | Bommannan et al. |
| 6,533,784 B2 | 3/2003 | Truckai et al. |
| 6,546,933 B1 | 4/2003 | Yoon |
| 6,554,829 B2 | 4/2003 | Schulze et al. |
| 6,564,806 B1 | 5/2003 | Fogarty et al. |
| 6,565,560 B1 | 5/2003 | Goble et al. |
| 6,565,561 B1 | 5/2003 | Goble et al. |
| 6,584,360 B2 | 6/2003 | Francischelli et al. |
| 6,610,074 B2 | 8/2003 | Santilli |
| 6,616,654 B2 | 9/2003 | Mollenauer |
| 6,616,659 B1 | 9/2003 | de la Torre et al. |
| 6,619,529 B2 | 9/2003 | Green et al. |
| 6,623,482 B2 | 9/2003 | Pendekanti et al. |
| 6,626,901 B1 | 9/2003 | Treat et al. |
| 6,645,198 B1 | 11/2003 | Bommannan et al. |
| 6,645,201 B1 | 11/2003 | Utley et al. |
| 6,648,839 B2 | 11/2003 | Manna et al. |
| 6,652,518 B2 | 11/2003 | Wellman et al. |
| 6,656,177 B2 | 12/2003 | Truckai et al. |
| 6,666,859 B1 | 12/2003 | Fleenor et al. |
| 6,669,696 B2 * | 12/2003 | Bacher ............... A61B 18/1445 606/206 |
| 6,673,085 B1 | 1/2004 | Berg |
| 6,676,660 B2 | 1/2004 | Wampler et al. |
| 6,682,526 B1 | 1/2004 | Jones et al. |
| 6,682,527 B2 | 1/2004 | Strul |
| 6,695,840 B2 | 2/2004 | Schulze |
| 6,699,245 B2 | 3/2004 | Dinger et al. |
| 6,719,754 B2 | 4/2004 | Underwood et al. |
| 6,722,371 B1 | 4/2004 | Fogarty et al. |
| 6,736,814 B2 | 5/2004 | Manna et al. |
| 6,743,229 B2 | 6/2004 | Buysse et al. |
| 6,746,488 B1 | 6/2004 | Bales |
| 6,752,154 B2 | 6/2004 | Fogarty et al. |

(56) References Cited

U.S. PATENT DOCUMENTS

| | | |
|---|---|---|
| 6,752,803 B2 | 6/2004 | Goldman et al. |
| 6,770,070 B1 | 8/2004 | Balbierz |
| 6,770,072 B1 | 8/2004 | Truckai et al. |
| 6,808,525 B2 | 10/2004 | Latteral et al. |
| 6,817,974 B2 | 11/2004 | Cooper et al. |
| 6,821,273 B2 | 11/2004 | Mollenauer |
| 6,837,888 B2 | 1/2005 | Ciarrocca et al. |
| 6,840,938 B1 | 1/2005 | Morley et al. |
| 6,843,789 B2 | 1/2005 | Goble |
| 6,852,108 B2 | 2/2005 | Barry et al. |
| 6,858,028 B2 | 2/2005 | Mulier et al. |
| 6,889,089 B2 | 5/2005 | Behl et al. |
| 6,893,435 B2 | 5/2005 | Goble |
| 6,896,672 B1 | 5/2005 | Eggers et al. |
| 6,896,673 B2 | 5/2005 | Hooven |
| 6,905,497 B2 | 6/2005 | Truckai et al. |
| 6,905,506 B2 | 6/2005 | Burbank et al. |
| 6,913,579 B2 | 7/2005 | Truckai et al. |
| 6,918,907 B2 | 7/2005 | Kelly et al. |
| 6,918,909 B2 | 7/2005 | Ohyama et al. |
| 6,923,803 B2 | 8/2005 | Goble |
| 6,926,712 B2 | 8/2005 | Phan |
| 6,929,642 B2 | 8/2005 | Xiao et al. |
| 6,936,048 B2 | 8/2005 | Hurst |
| 6,939,346 B2 | 9/2005 | Kannenberg et al. |
| 6,953,461 B2 | 10/2005 | McClurken et al. |
| 6,981,628 B2 | 1/2006 | Wales |
| 7,011,657 B2 | 3/2006 | Truckai et al. |
| 7,033,356 B2 | 4/2006 | Latterall et al. |
| 7,063,699 B2 | 6/2006 | Hess et al. |
| 7,090,637 B2 | 8/2006 | Danitz et al. |
| 7,090,673 B2 | 8/2006 | Dycus et al. |
| 7,090,685 B2 | 8/2006 | Kortenbach et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,118,587 B2 | 10/2006 | Dycus et al. |
| 7,125,409 B2 | 10/2006 | Truckai et al. |
| 7,137,980 B2 | 11/2006 | Buysse et al. |
| 7,150,097 B2 * | 12/2006 | Sremcich ........... A61B 18/1445 29/854 |
| 7,159,750 B2 | 1/2007 | Racenet et al. |
| 7,166,102 B2 | 1/2007 | Fleenor et al. |
| 7,169,146 B2 | 1/2007 | Truckai et al. |
| 7,179,254 B2 | 2/2007 | Pendekanti et al. |
| 7,195,627 B2 | 3/2007 | Amoah et al. |
| 7,220,260 B2 | 5/2007 | Fleming et al. |
| 7,238,195 B2 | 7/2007 | Viola |
| 7,250,048 B2 | 7/2007 | Francischelli et al. |
| 7,267,677 B2 | 9/2007 | Johnson et al. |
| 7,270,664 B2 | 9/2007 | Johnson et al. |
| 7,276,068 B2 | 10/2007 | Johnson et al. |
| 7,278,991 B2 | 10/2007 | Morris et al. |
| 7,291,143 B2 | 11/2007 | Swanson |
| 7,364,577 B2 | 4/2008 | Wham et al. |
| 7,367,972 B2 | 5/2008 | Francischelli et al. |
| 7,410,483 B2 | 8/2008 | Danitz et al. |
| 7,494,039 B2 | 2/2009 | Racenet et al. |
| 7,506,790 B2 | 3/2009 | Shelton |
| 7,540,872 B2 | 6/2009 | Schechter et al. |
| 7,549,564 B2 | 6/2009 | Boudreaux |
| 7,624,902 B2 | 12/2009 | Marczyk et al. |
| 7,641,651 B2 | 1/2010 | Nezhat et al. |
| 7,703,653 B2 | 4/2010 | Shah et al. |
| 7,794,461 B2 | 9/2010 | Eder et al. |
| 7,803,156 B2 | 9/2010 | Eder et al. |
| 7,862,565 B2 | 1/2011 | Eder et al. |
| 7,942,874 B2 | 5/2011 | Eder et al. |
| 8,419,727 B2 | 4/2013 | Koss et al. |
| 8,827,992 B2 | 9/2014 | Koss et al. |
| 8,870,867 B2 | 10/2014 | Walberg et al. |
| 2001/0001820 A1 | 5/2001 | Wampler et al. |
| 2001/0029367 A1 | 10/2001 | Fleenor et al. |
| 2002/0062123 A1 | 5/2002 | McClurken et al. |
| 2002/0062136 A1 | 5/2002 | Hillstead et al. |
| 2002/0107514 A1 | 8/2002 | Hooven |
| 2002/0111624 A1 | 8/2002 | Witt et al. |
| 2002/0124853 A1 | 9/2002 | Burbank et al. |
| 2002/0128643 A1 | 9/2002 | Simpson et al. |
| 2002/0151882 A1 | 10/2002 | Marko et al. |
| 2002/0177848 A1 | 11/2002 | Truckai et al. |
| 2002/0183738 A1 | 12/2002 | Chee et al. |
| 2003/0073994 A1 | 4/2003 | Schulze |
| 2003/0078577 A1 | 4/2003 | Truckai et al. |
| 2003/0114851 A1 | 6/2003 | Truckai et al. |
| 2003/0144652 A1 | 7/2003 | Baker et al. |
| 2003/0144653 A1 | 7/2003 | Francischelli et al. |
| 2003/0158547 A1 | 8/2003 | Phan |
| 2003/0171745 A1 | 9/2003 | Francischelli et al. |
| 2003/0216726 A1 | 11/2003 | Eggers et al. |
| 2003/0229344 A1 | 12/2003 | Dycus et al. |
| 2003/0236549 A1 | 12/2003 | Bonadio et al. |
| 2004/0006339 A1 | 1/2004 | Underwood et al. |
| 2004/0010245 A1 | 1/2004 | Cerier et al. |
| 2004/0068274 A1 | 4/2004 | Hooven |
| 2004/0097919 A1 | 5/2004 | Wellman et al. |
| 2004/0122423 A1 | 6/2004 | Dycus et al. |
| 2004/0143263 A1 | 7/2004 | Schechter et al. |
| 2004/0199226 A1 | 10/2004 | Shadduck et al. |
| 2004/0236320 A1 | 11/2004 | Protsenko et al. |
| 2005/0010212 A1 | 1/2005 | McClurken et al. |
| 2005/0015085 A1 | 1/2005 | McClurken et al. |
| 2005/0021026 A1 | 1/2005 | Bailey |
| 2005/0021027 A1 | 1/2005 | Shields et al. |
| 2005/0033276 A1 | 2/2005 | Adachi |
| 2005/0033277 A1 | 2/2005 | Clague et al. |
| 2005/0033278 A1 | 2/2005 | McClurken et al. |
| 2005/0070895 A1 | 3/2005 | Ryan et al. |
| 2005/0070978 A1 | 3/2005 | Bek et al. |
| 2005/0090819 A1 | 4/2005 | Goble |
| 2005/0096645 A1 | 5/2005 | Wellman et al. |
| 2005/0096694 A1 | 5/2005 | Lee |
| 2005/0107781 A1 | 5/2005 | Ostrovsky et al. |
| 2005/0107784 A1 | 5/2005 | Moses et al. |
| 2005/0113817 A1 | 5/2005 | Isaacson et al. |
| 2005/0113820 A1 | 5/2005 | Goble et al. |
| 2005/0119654 A1 | 6/2005 | Swanson et al. |
| 2005/0124987 A1 | 6/2005 | Goble |
| 2005/0131390 A1 | 6/2005 | Heinrich et al. |
| 2005/0149073 A1 | 7/2005 | Arani et al. |
| 2005/0171533 A1 | 8/2005 | Latterell et al. |
| 2005/0187561 A1 | 8/2005 | Lee-Sepsick et al. |
| 2005/0192633 A1 | 9/2005 | Montpetit |
| 2005/0196421 A1 | 9/2005 | Hunter et al. |
| 2005/0203500 A1 | 9/2005 | Saadat et al. |
| 2005/0203504 A1 | 9/2005 | Wham et al. |
| 2005/0209664 A1 | 9/2005 | Hunter et al. |
| 2005/0226682 A1 | 10/2005 | Chersky et al. |
| 2005/0256522 A1 | 11/2005 | Francischelli et al. |
| 2005/0256524 A1 | 11/2005 | Long et al. |
| 2005/0261676 A1 | 11/2005 | Hall et al. |
| 2006/0025765 A1 | 2/2006 | Landman et al. |
| 2006/0025812 A1 | 2/2006 | Shelton |
| 2006/0041254 A1 | 2/2006 | Francischelli et al. |
| 2006/0047278 A1 * | 3/2006 | Christian ........... A61B 18/1492 606/41 |
| 2006/0052778 A1 | 3/2006 | Chapman et al. |
| 2006/0052779 A1 | 3/2006 | Hammill |
| 2006/0064084 A1 | 3/2006 | Haemmerich et al. |
| 2006/0079872 A1 | 4/2006 | Eggleston et al. |
| 2006/0079891 A1 | 4/2006 | Arts et al. |
| 2006/0167451 A1 | 7/2006 | Cropper |
| 2006/0190029 A1 | 8/2006 | Wales |
| 2006/0199999 A1 | 9/2006 | Ikeda et al. |
| 2006/0217709 A1 | 9/2006 | Couture et al. |
| 2006/0226196 A1 | 10/2006 | Hueil et al. |
| 2006/0229665 A1 | 10/2006 | Wales et al. |
| 2006/0253117 A1 | 11/2006 | Hovda et al. |
| 2006/0258954 A1 | 11/2006 | Timberlake et al. |
| 2006/0259035 A1 | 11/2006 | Nezhat et al. |
| 2006/0271037 A1 | 11/2006 | Maroney et al. |
| 2006/0271041 A1 | 11/2006 | Eder et al. |
| 2006/0271042 A1 | 11/2006 | Latterell et al. |

(56) References Cited

U.S. PATENT DOCUMENTS

| | | |
|---|---|---|
| 2006/0287674 A1 | 12/2006 | Ginn et al. |
| 2006/0289602 A1 | 12/2006 | Wales et al. |
| 2006/0293655 A1 | 12/2006 | Sartor |
| 2007/0005061 A1 | 1/2007 | Eder et al. |
| 2007/0055231 A1 | 3/2007 | Dycus et al. |
| 2007/0062017 A1 | 3/2007 | Dycus et al. |
| 2007/0073340 A1 | 3/2007 | Shelton et al. |
| 2007/0128174 A1 | 6/2007 | Kleinsek et al. |
| 2007/0129726 A1 | 6/2007 | Eder et al. |
| 2007/0173804 A1 | 7/2007 | Wham et al. |
| 2007/0173805 A1 | 7/2007 | Weinberg et al. |
| 2007/0173811 A1 | 7/2007 | Couture et al. |
| 2007/0179497 A1 | 8/2007 | Eggers et al. |
| 2007/0185482 A1 | 8/2007 | Eder et al. |
| 2007/0208336 A1 | 9/2007 | Kim et al. |
| 2007/0244538 A1 | 10/2007 | Eder et al. |
| 2007/0250113 A1 | 10/2007 | Hegeman et al. |
| 2007/0265613 A1 | 11/2007 | Edelstein et al. |
| 2007/0282318 A1 | 12/2007 | Spooner et al. |
| 2007/0282320 A1 | 12/2007 | Buysse et al. |
| 2008/0172052 A1 | 7/2008 | Eder et al. |
| 2008/0188844 A1 | 8/2008 | McGreevy et al. |
| 2008/0195093 A1 | 8/2008 | Couture et al. |
| 2008/0221565 A1 | 9/2008 | Eder et al. |
| 2008/0228179 A1 | 9/2008 | Eder et al. |
| 2008/0275446 A1 | 11/2008 | Messerly |
| 2008/0308607 A1 | 12/2008 | Timm et al. |
| 2009/0018535 A1 | 1/2009 | Schechter et al. |
| 2009/0112246 A1 | 4/2009 | Weisshaupt et al. |
| 2009/0138006 A1 | 5/2009 | Bales et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0182323 A1 | 7/2009 | Eder et al. |
| 2009/0182333 A1 | 7/2009 | Eder et al. |
| 2009/0198272 A1 | 8/2009 | Kerver et al. |
| 2009/0209953 A1 | 8/2009 | Schoenman |
| 2009/0240245 A1 | 9/2009 | Deville et al. |
| 2009/0299367 A1 | 12/2009 | Ginnebaugh et al. |
| 2010/0042093 A9 | 2/2010 | Wham et al. |
| 2010/0076427 A1 | 3/2010 | Heard |
| 2010/0094282 A1 | 4/2010 | Kabaya et al. |
| 2010/0280508 A1 | 11/2010 | Eder |
| 2010/0298823 A1 | 11/2010 | Cao et al. |
| 2011/0184404 A1 | 7/2011 | Walberg et al. |
| 2011/0202058 A1 | 8/2011 | Eder et al. |
| 2011/0230875 A1 | 9/2011 | Walberg et al. |
| 2011/0238056 A1 | 9/2011 | Koss et al. |
| 2012/0071871 A1 | 3/2012 | Lue et al. |

FOREIGN PATENT DOCUMENTS

| | | |
|---|---|---|
| CA | 2237429 A1 | 11/1998 |
| CN | 1250360 A | 4/2000 |
| CN | 1882289 A | 12/2006 |
| CN | 1889893 A | 1/2007 |
| DE | 202007005510 U1 | 6/2007 |
| DE | 202007015547 U1 | 1/2008 |
| DE | 102007017966 B3 | 11/2008 |
| DE | 102007053359 B3 | 6/2009 |
| DE | 202011000800 U1 | 5/2011 |
| EP | 0134750 A1 | 3/1985 |
| EP | 0440385 A2 | 8/1991 |
| EP | 0487269 A1 | 5/1992 |
| EP | 0502268 A1 | 9/1992 |
| EP | 0562195 A1 | 9/1993 |
| EP | 0658333 A1 | 12/1994 |
| EP | 0923907 A1 | 6/1999 |
| EP | 0833593 B1 | 2/2001 |
| EP | 1254637 A1 | 11/2002 |
| EP | 0737446 B1 | 12/2002 |
| EP | 0717960 B1 | 2/2003 |
| EP | 0869742 B1 | 5/2003 |
| EP | 1330991 A1 | 7/2003 |
| EP | 0873089 B1 | 10/2003 |
| EP | 0742696 B1 | 11/2003 |
| EP | 1041933 B1 | 3/2004 |
| EP | 1004277 B1 | 7/2004 |
| EP | 0959786 B1 | 9/2004 |
| EP | 0913126 B1 | 10/2004 |
| EP | 0956827 B1 | 10/2004 |
| EP | 1472984 A1 | 11/2004 |
| EP | 1621146 A2 | 2/2006 |
| EP | 1645237 A1 | 4/2006 |
| EP | 0875209 B1 | 5/2006 |
| EP | 1293170 B1 | 6/2006 |
| EP | 1293169 B1 | 7/2006 |
| EP | 1064886 B1 | 8/2006 |
| EP | 1767164 A1 | 3/2007 |
| EP | 1810625 A1 | 7/2007 |
| EP | 1518498 B1 | 12/2007 |
| EP | 1862138 A1 | 12/2007 |
| EP | 1039862 B1 | 5/2008 |
| EP | 1532933 B1 | 5/2008 |
| EP | 1707143 B1 | 6/2008 |
| EP | 1518499 B1 | 8/2008 |
| EP | 1632192 B1 | 3/2009 |
| EP | 1486177 B1 | 8/2009 |
| EP | 1852081 B1 | 8/2009 |
| EP | 1747761 B1 | 10/2009 |
| EP | 2106764 A2 | 10/2009 |
| JP | 06237936 A | 8/1994 |
| JP | 11137562 A | 5/1999 |
| JP | 2001095813 A | 4/2001 |
| JP | 2003088534 | 3/2003 |
| JP | 2004049566 | 2/2004 |
| JP | 2005160889 A | 6/2005 |
| JP | 2005144193 | 9/2005 |
| WO | 9222257 A1 | 12/1992 |
| WO | 9308754 A1 | 5/1993 |
| WO | 9400060 A1 | 1/1994 |
| WO | 9406179 A1 | 11/1994 |
| WO | 9502371 A1 | 1/1995 |
| WO | 9605776 A1 | 2/1996 |
| WO | 9616605 A1 | 6/1996 |
| WO | 9623449 A1 | 6/1996 |
| WO | 9724073 A1 | 7/1997 |
| WO | 9724074 A1 | 7/1997 |
| WO | 9812999 A2 | 4/1998 |
| WO | 9843548 A1 | 10/1998 |
| WO | 9853750 A1 | 12/1998 |
| WO | 9923933 A2 | 5/1999 |
| WO | 9952459 A1 | 10/1999 |
| WO | 9956646 A1 | 11/1999 |
| WO | 0013192 A1 | 3/2000 |
| WO | 0013193 A1 | 3/2000 |
| WO | 0112090 A1 | 2/2001 |
| WO | 0135846 A1 | 5/2001 |
| WO | 0154602 A2 | 8/2001 |
| WO | 0158372 A1 | 8/2001 |
| WO | 0158373 A1 | 8/2001 |
| WO | 0182812 A1 | 11/2001 |
| WO | 0224092 A1 | 3/2002 |
| WO | 02058542 A2 | 8/2002 |
| WO | 02067798 A1 | 9/2002 |
| WO | 03088806 A2 | 10/2003 |
| WO | 03103522 A1 | 12/2003 |
| WO | 2004032596 A2 | 4/2004 |
| WO | 2004032776 A1 | 4/2004 |
| WO | 2004073490 A2 | 9/2004 |
| WO | 2004098383 A2 | 11/2004 |
| WO | 2005009213 A2 | 2/2005 |
| WO | 2005034729 A2 | 4/2005 |
| WO | 2005079901 A1 | 9/2005 |
| WO | 2005115251 A1 | 12/2005 |
| WO | 2006060431 A1 | 6/2006 |
| WO | 2007002227 A2 | 1/2007 |
| WO | 2007082061 A2 | 7/2007 |

(56) References Cited

FOREIGN PATENT DOCUMENTS

| WO | 2008094554 A2 | 8/2008 |
|---|---|---|
| WO | 2008124112 A1 | 10/2008 |

OTHER PUBLICATIONS

Novare, "U.S. Patent Issued for Novare Surgical Systems Cygnet® Surgical Clamp; Novare Multi-Year Supply Agreement with Boston Scientific", PR Newswire, pNA, Sep. 2, 2003—2 pages.
Office Action for U.S. Appl. No. 13/536,149, dated Oct. 6, 2014—8 pages.
Parikh et al., "Three Dimensional Virtual Reality Model of the Normal Female Pelvic Floor", Annuals of Biomedical Engineering, vol. 32, Feb. 2004—pp. 292-296.
Refractec, Inc. "Medical Use of Radiofrequency (RF) Energy", http://www.locateadoc.com/Site_Tools/Print.cfm, Aug. 23, 2008, downloaded Feb. 7, 2011—2 pages.
SAGES 2001 Hands on Course I—"Taking it to the Next Level: Advanced Laparoscopic Techniques", http://www.sages.org/01program/syllabi/ho1/ho1.html#schrime, downloaded Oct. 5, 2005—24 pages.
SAGES 2001 Nurses Program, Session 1, http://sages.org/01programs/syllabi/nurse.html, downloaded Jan. 24, 2011—5 pages.
Srisombut et al., "Laparoscopic Hysterectomy Using Laparosonic Coagulating Shears: Experience of 15 Cases", J. Med. Assoc. Thai., vol. 83, No. 8, Aug. 2000—pp. 915-920.
SURGRX 510(K) Summary (K031133), Palo Alto, CA, Jul. 3, 2003—5 pages.
Treat, M., "A New Thermal Device for Sealing and Dividing Blood Vessels", http:///www.starioninstruments.com/PDFs/Teeat.pdf, downlaoded Jun. 29, 2005—2 pages.
Tyco Healthcare, "The Ligasure* Vessel Sealing System" (Brochure), Apr. 2002—8 pages.
Valleylab Products, "Electrosurgical Forceps: The Surgeons Choice for Quality and Precision", (Product information) http://www.valleylab.com/product/es/accessories/forceps_over.html, downloaded Oct. 20, 2005—1 page.
Valleylab Products, "Ligasure Vessel Sealing System" (Product information) http://www.valleylab.com/product/vessel_seal/index.html, downloaded Oct. 20, 2005—1 page.
Notice of Allowance for U.S. Appl. No. 15/094,332, dated Apr. 18, 2018, 10 pages.
Entire patent prosecution history of U.S. Appl. No. 13/021,633, filed Feb. 4, 2011, entitled "Laparoscopic Radiofrequency Surgical Device".
Aoki et ai., "Thoracoscopic Resection of the Lung With the Ultrasonic Scalpel", Ann. Thorac. Surg., vol. 67, No. 4, Apr. 1999—pp. 1181-1183.
ArthroCare, "ArthroCare Receives Clearance to Market Coblation-based Devices for Gynecology and Laproscopic Surgery: Clearance Includes Plasma Forceps and 21 Specific Indications", Business Wire, Oct. 25, 2001—p. 524.
Australian Examination Report for Australian Application No. 2011212786, dated Apr. 16, 2014—4 pages.
Australian Examination Report for Australian Application No. 2007352602, dated Aug. 21, 2012—4 pages.
Bergamaschi et al., "Laparoscopic Intracorporeal Bowel Resection with Ultrasound Versus Electrosurgical Dissection", Journal of the Society of Laproscopic Surgeons, vol. 5, No. 1, Jan.-Mar. 2001—pp. 17-20.
Business Wire, "Radiofrequency Energy Proven Effective Against Leading Cause of Obstructive Sleep Apnea", Business Wire, Sep. 14, 1998 (p09140175)—4 pages.
Chinese Examination Report for Chinese Application No. 200780053005.9, dated Jun. 26, 2012—15 pages.
Chinese Examination Report for Chinese Application No. 200780053005.9, dated Oct. 18, 2011—8 pages.
First Office Action for Chinese Application No. 201180003207.9, dated Jul. 9, 2014—31 pages.
Fourth Chinese Office Action for Chinese Application No. 200780053005.9, dated Mar. 27, 2013—36 pages.
First Office Action for Chinese Application No. 200880005613.7, dated Mar. 19, 2012—15 pages.
Curon, "Curon Announces the Publication of Data Supporting Durability and Effectiveness of Stretta® System;—Positive One Year Follow-Up Data of U.S. Clinical Trial Published in Gastrointestinal Endoscopy", PR Newswire; pNYTH10307022002, Feb. 2002—2 pages.
Curon, "Curon Medical Announces Presentation of Positive Clinical Study Results of Stretta® Procedure for Gastroesophageal Reflux Disease (GERD);—Follow-Up Data from Vanderbuilt University Study Presented at the 8th World Congress of Surgery and the Society of American Gastrointestinal Endoscopic Surgeons", PR Newswire, pNYW07920032002, Mar. 20, 2002—3 pages.
Eichfeld et al., "Evaluation of Ultracision in Lung Metastatic Surgery", Ann. Thorac. Surg., vol. 70, No. 4, Oct. 2000—pp. 1181-1184 2018.
Enable, "Enable Medical Introduces Second Generation Bipolar Scissors", Health Industry Today, pNA, Dec. 1998—2 pages.
European Office Action for European Application No. 07 811 938.5, dated Mar. 5, 2012—5 pages.
ERBE Elektromedizin GmbH; ERBE BiClamp®: Bipolar Electrosurgical Coagulation—Effective Large-Scale Coagulation of Tissue Structures in Open Surgery and Laparoscopy, http://www.erbe-med.com/erbe/media/Marketingmaterialien/85100-139_ERBE_EN_Biclamp_D024676.pdf; downloaded Jan. 24, 2011—6 pages.
Everest, "Everest Medical Announces Introduction of 3mm Bipolar Forceps", PR Newswire, p1002MNW021, Oct. 2, 1996—2 pages.
Everest, "Everest Medical Discusses Patent Status; Forecasts $1 Million Revenue First Quarter; Introduces Next Generation Bipolar Scissors", PR Newswire, pN/a, Mar. 31, 1994—1 page.
Everest, "Everest Medical Introduces New Quadripolar™ Cutting Forceps at the Global Congress of Gynecologic Endoscopy Meeting", PR Newswire, Nov. 8, 1999—p. 8927.
Everest, Everest Medical Reports Record First Quarter Results: Introduces Next Generation Bipolar Scissors; PR Newswire, pN/A, Apr. 1994—1 page.
Everest, Quadripolar Cutting Forceps Introduced by Everest Medical, Health Industry Today, vol. 63, No. 1, pNA, Jan. 2000—1 page.
Final Office Action for U.S. Appl. No. 15/094,332, dated Nov. 2, 2017—9 pages.
GYRUS Medical, Cutting Forceps (Product Information), downloaded Oct. 5, 2005—1 page.
GYRUS Medical, Lyons™ Dissecting Forceps (Product Information), downloaded Oct. 5, 2005—1 page.
GYRUS Medical, LP Scissors (Product Information), downloaded Oct. 5, 2005—1 page.
GYRUS Medical, Micro/macro-Jaw Forceps (Product Information), downloaded Oct. 5, 2005—1 page.
GYRUS Medical, PKS Seal™ Open Forceps (Product Information), downloaded Jan. 24, 2011—1 page.
GYRUS Medical, Seal™ Open Forceps (Product Information), downloaded Jan. 24, 2011—1 page.
Hayashi et al., "Experimental and Clinical Evaluation of the Harmonic Scalpel in Thoracic Surgery", Kurume Med. J., vol. 46, No. 1, 1999—pp. 25-29.
Hefni et al., "Safety and Efficacy of Using the LigaSure Vessel Sealing System for Securing the Pedicles in Vaginal Hysterectomy: Radomised Controlled Trial", BJOG, vol. 112, No. 3, Mar. 2005—pp. 329-333.
Heniford et al., "Initial Results with an Electrothermal Bipolar Vessel Sealer", Surg. Endosc., vol. 15, No. 8, Aug. 2001—pp. 799-801.
International Preliminary Report on Patentability for International Application No. PCT/US2011/023731, dated Aug. 7, 2012—6 pages.
International Search Report for International Application No. PCT/US2011/023731, dated Oct. 13, 2011—11 pages.
Johnson & Johnson Gateway, LLC, The Gynecare Versapoint (Product Information) downloaded Oct. 20, 2005—3 pages.
Japanese Examination Report for Application No. 2010/506177, dated Sep. 29, 2011—6 pages.
Kamat et al., "Superiority of Electrocautery Over the Suture Method for Achieving Cervical Cone Bed Hemostasis", Obstet Gynocol., vol. 102, No. 4, Oct. 2003—pp. 726-730.

(56) References Cited

OTHER PUBLICATIONS

Kennedy et al., "High-burst-strength, Feedback-controlled Bipolar Vessel Sealing", Surg. Endosc, vol. 12, No. 6, Jun. 1998—pp. 876-878.

Kim et al., "Design and Fabrication of a Locomotive Mechanism for Capsule-type Endoscopes Using Shape Memory Alloys (SMAs)", IEEE/ASME Trans on Mechatronics, vol. 10, No. 1, Feb. 2005—pp. 77-86.

Kovac, S., "Transvaginal Hysterectomy: Rationale and Surgical Approach", Obstet. Gynecol., vol. 103, 2004—pp. 1321-1325.

Landman et al., "Evaluation of a Vessel Sealing System, Bipolar Electrosurgery, Harmonic Scalpel, Titanium Clips, Endoscopic Gastrointestinal Anastomosis Vascular Staples and Sutures for Arterial and Venous Ligation in a Porcine Model", J. of Urology, vol. 169, Feb. 2003—pp. 697-700.

Levy et al., "Update on Hysterectomy: New Technologies and Techniques", A Supplement to OBG Management, Feb. 2003—16 pages.

Levy et al., "Use of a New Vessel Litigation Device During Vaginal Hysterectomy", (Presentation Abstract), presented at FIGO 2000: Washington D.C., 2000—1 page.

Lin et al., "Application of Ultrasonic Scalpel in Gynecologic Operative Laparoscopy", Chin. Med. J., vol. 114, No. 12, Dec. 2001—pp. 1283-1285.

Live Tissue Connect Technologies; Company profile, http://www.onemedplace.com/database/compdisplay_print.php?CompanyID=11508, Oct. 19, 2010, downloaded Feb. 7, 2011—1 page.

Lyons et al., "An Innovative Bipolar Instrument for Laparoscopic Surgery", JSLS, vol. 9, No. 1, Jan.-Mar. 2005—pp. 39-41.

McClurkin et al., "Collagen Shrinkage and Vessel Sealing", Technical Brief #300, Dover, NH, Tissue Link Medical 2001—2 pages.

Non-Final Office Action for U.S. Appl. No. 15/094,332, dated Apr. 7, 2017—32 pages.

Non-Final Office Action for U.S. Appl. No. 13/536,149, dated Nov. 6, 2015—30 pages.

Notice of Allowance for U.S. Appl. No. 13/536,149, dated Jan. 13, 2016—5 pages.

\* cited by examiner

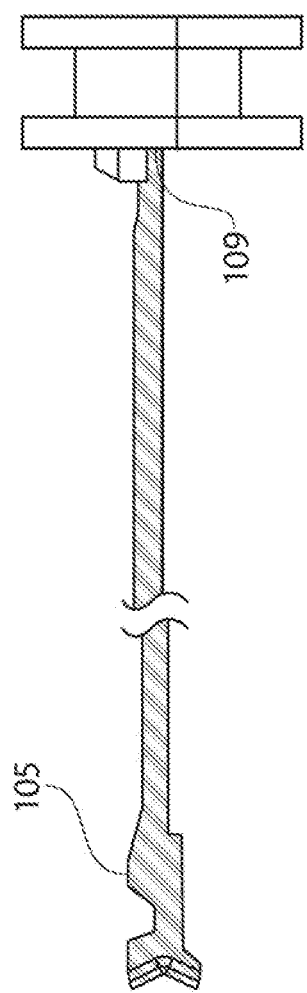
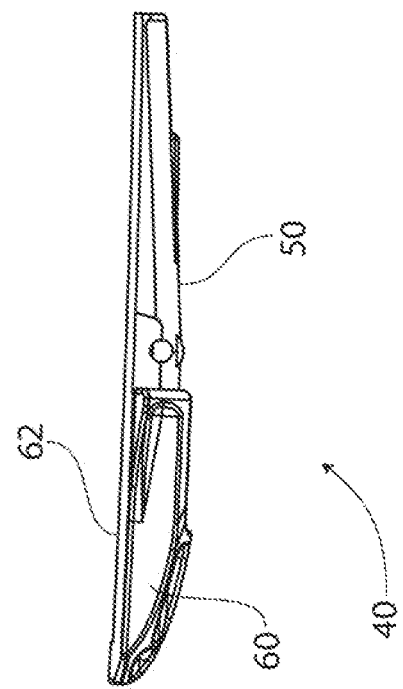
FIG. 4D

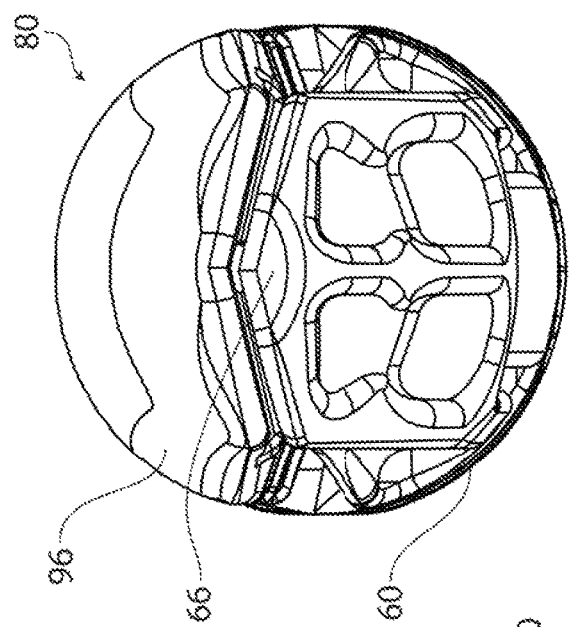
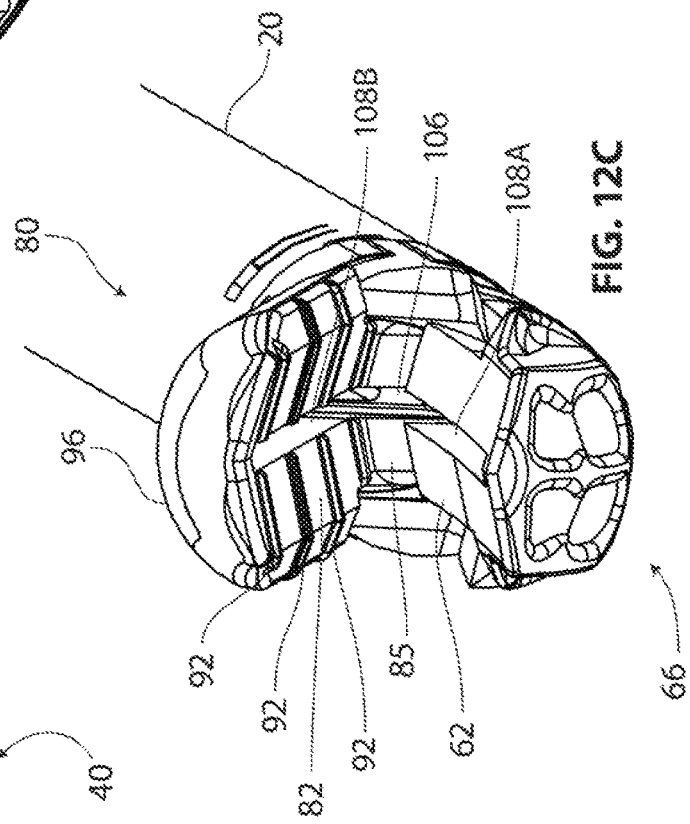
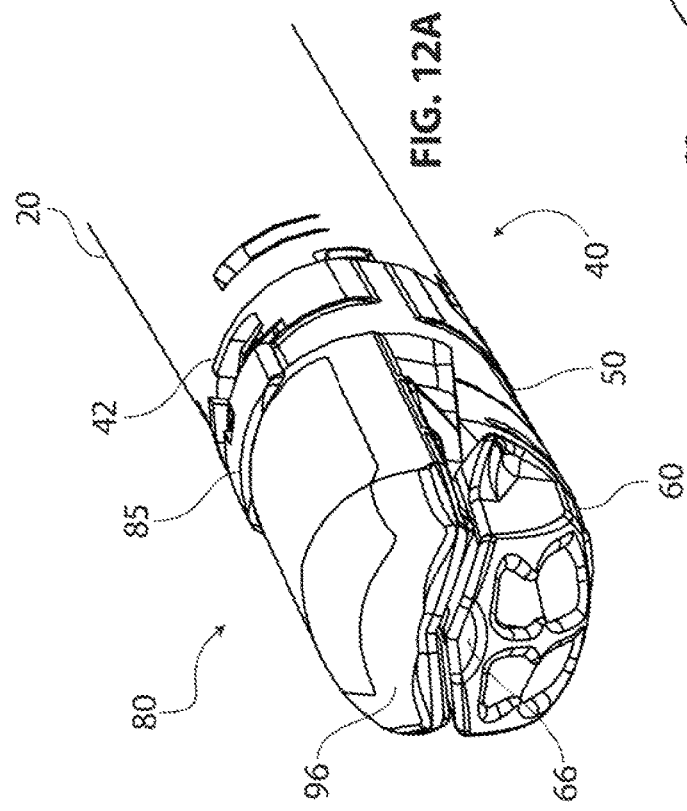

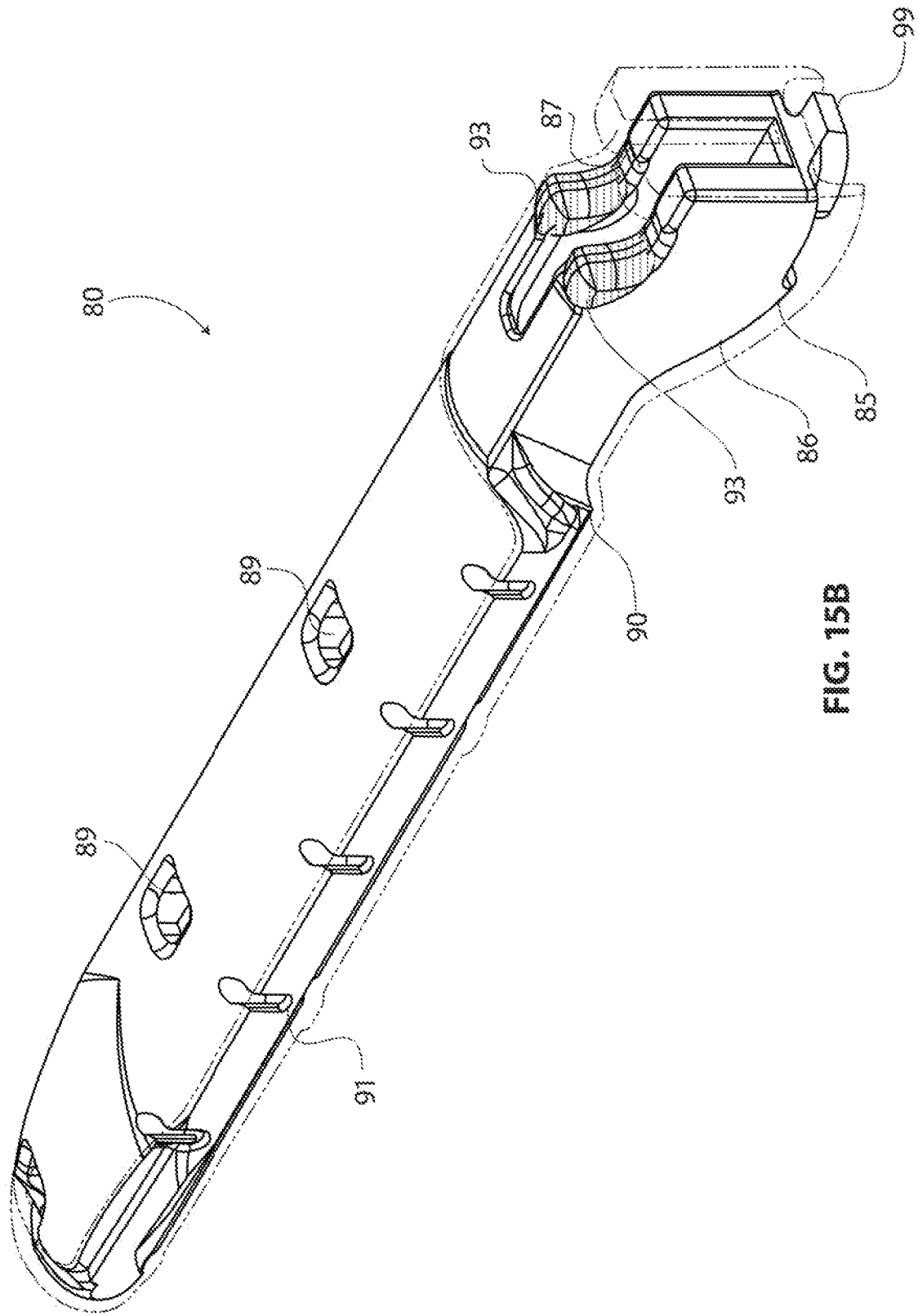

LAPAROSCOPIC RADIOFREQUENCY SURGICAL DEVICE

CROSS-REFERENCE TO RELATED APPLICATIONS

This application is a continuation of U.S. application Ser. No. 13/021,633, filed Feb. 4, 2011, which claims the benefit of priority of U.S. Provisional Patent Application No. 61/301,295 filed Feb. 4, 2010, now lapsed, and which is a continuation-in-part of U.S. patent application Ser. No. 11/743,579, filed May 2, 2007, now U.S. Pat. No. 8,574,229, which is a continuation-in-part of U.S. patent application Ser. No. 11/382,652, filed May 10, 2006, now U.S. Pat. No. 7,942,874, which claims priority to U.S. Provisional Patent Application No. 60/746,256, filed May 2, 2006, now lapsed.

INCORPORATION BY REFERENCE

All publications, patent applications, and patents mentioned in this specification are herein incorporated by reference to the same extent as if each such individual publication or patent application were specifically and individually indicated to be so incorporated by reference.

TECHNICAL FIELD

The disclosed technology relates to systems and methods for electrosurgery. More particularly, the technology relates to an electrosurgical device appropriate for laparoscopic surgery through a trocar with a 5 mm port.

BACKGROUND

Biopolar electrosurgical instruments apply radiofrequency (RF) energy to a surgical site to cut, ablate, or coagulate tissue. A particular application of these electrosurgical effects is to seal blood vessels or tissue sheets. A typical instrument takes the form of a set of forceps or pair of jaws, with one or more electrodes on each jaw tip. In an electrosurgical procedure, the electrodes are placed in close proximity to each other as the jaws are closed on a target site such that the path of alternating current between the two electrodes passes through tissue within the target site. The mechanical force exerted by the jaws and the electrical current combine to create the desired surgical effect. By controlling the level of mechanical and electrical parameters, such as the pressure applied by the jaws, the gap distance between electrodes, and the voltage, current, frequency, and duration of the electrosurgical energy applied to the tissue, the surgeon can coagulate, cauterize, or seal tissue toward a therapeutic end.

Electrosurgical procedures can be performed in an open environment, through conventional incisions, or they may be performed laparoscopically, through small incisions, typically 0.5 cm-1.5 cm in length. A laparoscopic procedure may include the use of a telescopic rod lens system that is connected to a video camera and to a fiber optic cable system that conveys light to illuminate the operative field. A laparoscope is typically inserted into a port in the body through a 5 mm or 10 mm cannula or trocar to view the operative field. Surgery is performed during a laparoscopic procedure with any of various tools that are typically arranged at the distal end of a shaft and are operable by manipulation of a handle or an actuator positioned at the proximal end of the shaft, and are dimensioned such that they can pass through a port provided by the 5 mm or 10 mm cannula.

As electrosurgical tools are applied in laparoscopic procedures, challenges to the devices arise regarding dimensional constraints imposed by the operating environment, including the smallness of a typical port of entry, which includes the use of conventional trocars with a 5 mm inner diameter. The technology provided herein addresses the need for improvements in device technology, that permit downsizing of the device while maintaining appropriate levels of mechanical strength and electrosurgical capability. For example, it is generally desirable to extend the length of conventional forceps in order to allow the sealing of greater lengths of tissue. As forceps length increases, it becomes a challenge to exert an appropriate level of force, particularly from the distal end of the forceps. The present disclosure provides technologies that represent progress in addressing these challenges.

SUMMARY OF THE DISCLOSURE

Embodiments of the technology relate to an electrosurgical device that is particularly suitable for laparoscopic procedures in that its distal insertable portion, including a shaft and an end effector, may have a diameter no wider than about 5 mm. This 5 mm insertable profile allows insertion of the device through a conventional 5 mm trocar. Commercially available trocars that are conventionally referred to as being "5 mm" generally have an internal diameter specification commonly expressed in inch units, and actually vary in range between about 0.230 inch and about 0.260 inch, even though 5 mm actually is the equivalent of 0.197 inches. In the present disclosure, therefore, "5 mm" or "about 5 mm", when referring to the insertable profile of the device, or to the diameter of the shaft or the jaws in a closed configuration, refers to a diameter that is accommodated by presently available "5 mm" trocars. More particularly, embodiments of the shaft and closed jaws disclosed herein typically have a diameter in the range of about 0.215 inch to about 0.222 inch.

Embodiments of the electrosurgical device have an end effector such as a set of two opposing jaws or forceps that include one or more bipolar electrode pairs disposed on tissue engaging surfaces of the jaws, the device being adapted to effect tissue sealing and cutting. In some embodiments, the device includes a single bipolar electrode pair, one electrode in each of the jaws. In these embodiments, the electrodes are typically powered by a generator operating with a single radiofrequency channel. Other embodiments of the device may include a plurality of bipolar electrode pairs, and an operation by way of a plurality of radiofrequency channels. Some particular embodiments of the technology may take the form of non-electrical surgical device whose operation takes advantage of the mechanical and dimensional aspects of the technology.

Embodiments of electrosurgical device may have jaws that self align with respect to their longitudinal axes when the jaws are approaching closure. Self-alignment, as used herein, may further be understood to include lateral alignment, such that when longitudinally aligned jaws converge on closure, they meet opposingly, their lateral or tissue engaging faces meeting each other fully, from respective proximal end to distal end. The mutual alignment of the jaws can be particularly challenged when the jaws are closing around a piece of tissue, whose presence can urge the jaws to skew laterally out of alignment such that they do not meet opposingly. Accordingly, in these jaw set embodiments, the tissue-engaging surfaces of each of the opposing jaws, respectively, have mutually complementary longitudinally oriented self-aligning features that are sufficiently robust to be effective when there is a surgically appropriate amount of target tissue within the space between the closing jaws. Aspects and details of embodiments of self-alignable jaws are described further below.

Embodiments of the jaws may be rotatable with respect to each other by way of a pinless rotation mechanism that operates by way of rotatably cooperative features of the jaws that connect the jaws together. The pinless rotatable mechanism, in addition to securing the jaws together, allows the jaws to pivot between the open position and the closed position. Embodiments of the jaw set may pivot as a whole between an open and a closed position by virtue of one jaw pivoting with respect to a shaft while the other jaw remains fixed with respect to the shaft. The center of rotation of this pinless rotation system is not necessarily disposed at a position on a line corresponding to a central longitudinal axis of the shaft. Particular embodiments of the pinless rotation mechanism are displaced from that line. An advantage of this pivotal or rotational mechanism is that force that is transferred to the mechanism from an actuator wire is increased by the angular moment provided by the distance of displacement of the center of rotation from the longitudinal axis of the shaft, or more particularly by the distance between the axis of the actuator wire within the shaft and the center of rotation.

In some embodiments, the rotatably cooperative features of the pinless rotation mechanism of the jaws include a first jaw in which a proximal aspect of the jaw has a first arcuate track, and second jaw in which a proximal aspect has a second arcuate track, the first and second arcuate tracks being mutually complementary and slidably engageable with each other. In one arrangement of these rotatable components, the arcuate track aspect of first jaw is generally external or female with respect to the arcuate aspect of the second jaw. Thus, the track of the first jaw accommodates and generally encloses the track portion of the second jaw, and the second jaw is rotatable within the space provided by the first jaw. The complementary rotatable portions of the first and second jaws are dimensioned such that their facing surfaces can be easily moved slidably past each other. In some of these embodiments, the second arcuate track substantially resides within an enclosure formed by the first arcuate track. Although the proximally positioned arcuate tracks are rotatable with respect to each other, in some embodiments, at least the proximal portion of the first jaw is fixed with regard to the shaft, while the second jaw is pivotable with respect to the shaft.

In some embodiments of the pinless rotation mechanism, the first arcuate track has two concentric surfaces facing each other, one smaller and the other larger, and the second arcuate track has two concentric surfaces facing away each other, one smaller and the other larger. The concentric surfaces of the two tracks are mating surfaces between the tracks. More particularly, the smaller concentric surfaces of the first and second tracks, respectively, are complementary to each other. The larger concentric surfaces of the first track and second track, respectively, are complementary to each other. The second arcuate track substantially resides within an enclosure formed by the first arcuate track. In particular embodiments, the first jaw includes a retaining strap that backs the smaller concentric surface of the first arcuate track and is positioned laterally across a surface of a housing of first jaw within a portion of the housing overlaying and securing the smaller concentric surface of the second jaw. This strap is configured to retain the proximal aspect of the second jaw within the enclosure provided by the first arcuate track.

From a general perspective, in embodiments of the device in which the shaft and the jaws are freely rotatable with respect to a handle portion, designating one jaw as a lower jaw and the other jaw as an upper jaw may not be particularly meaningful. Nevertheless, in some embodiments of the device, by virtue of a convention, or by some designation, there may be a default rotational position of the jaws that particularizes one jaw as a lower jaw and the other as an upper jaw. Thus, in particular embodiments of the device, and in the examples of device embodiments depicted herein, from the perspective of an operator of the device and with the jaws in a default operating position, a referenced first jaw is a lower jaw and a referenced second jaw is an upper jaw.

Typical embodiments of an electrosurgical device as described herein may have one jaw that is pivotable with respect to the shaft and a second jaw having at least a base portion that is fixed with respect to the shaft. Embodiments such as these are described in detail herein, and are depicted as examples in the figures. Alternative embodiments of the device, however, may be configured such that both jaws are pivotable with respect to the shaft.

Typical embodiments of the device as described herein are also configured such that one jaw is a two-piece jaw, including a proximal base piece and a distal piece that is pivotable with respect to the proximal base piece, and a second jaw that is unitary. Embodiments such as these are described in detail herein, and are depicted as examples in the figures. Alternative embodiments of the device, however, may be configured such that both jaws have two pieces, with a distal portion that is pivotable with respect to a proximal base portion.

Embodiments of an electrosurgical device as provided herein may vary in tennis of the distribution of features between a first jaw and a second jaw. Thus, in some embodiments of the device (Embodiment A), a first jaw (a lower jaw, for example) is a two-piece jaw, having a proximal piece that is fixed with respect to the shaft, a distal jaw piece that is pivotable with respect to the proximal piece, and a pivotable assembly connecting the proximal piece and the distal jaw piece; and a second jaw (an upper jaw, for example) is unitary and pivotable with respect to the shaft.

In alternative embodiments of the device (Embodiment B), a first jaw (a lower jaw, for example) is unitary and fixed with respect to the shaft; and a second jaw (an upper jaw, for example) is a 2-piece jaw, having a proximal jaw piece that is pivotable with respect to the shaft, a distal jaw piece that is pivotable with respect to the proximal piece, and a pivotable assembly connecting the proximal jaw piece and the distal jaw piece. Examples of both embodiments A and B are depicted as examples in the figures.

In another aspect, Embodiment A of the device may be described as having two jaws, a first jaw that is fixed with respect to the shaft and having pivotable electrode tray positioned with in it, and a second jaw being pivotable with respect the shaft and having a fixed electrode tray disposed within it. Embodiment B of the device may be described as having two jaws, a first jaw that is fixed with respect to the shaft and having a fixed electrode tray disposed with in it, and a second jaw that is pivotable with respect to the shaft, and having a pivotable electrode tray with in it. Other than the variation associated with the distribution of jaw attributes between Embodiments A and B, other features of the Embodiment A and Embodiment B devices are substantially similar. The majority of features shown in figures included herein are consistent with Embodiment A or common to both Embodiments A and B. FIGS. 5A-5C depict Embodiment B in particular.

A further embodiment (Embodiment C) of the device may be described as having two jaws, a first jaw that is fixed with respect to the shaft and having a pivotable electrode tray positioned with in it, and a second jaw that is pivotable with respect to the shaft, and having a pivotable electrode tray with in it. Still further embodiments have both jaws pivotable with respect to the shaft. Thus Embodiment D has two jaws that are pivotable with respect to the shaft; it has a first jaw having a pivotable electrode tray positioned within it and a second jaw having a fixed electrode tray disposed with in it. Embodiment E has two jaws that are pivotable with respect to the shaft, both jaws having a pivotable electrode tray positioned within it.

In some aspects of the disclosure, an embodiment of the device consists of a set of jaws as described herein, but which are specifically absent a shaft, absent a handle, or absent both a shaft and a handle. The set of jaws per these embodiments may be appropriately fitted onto a shaftless device, or alternatively, onto a robotic device. These embodiments may or may not be configured for electrosurgery. Some embodiments include bipolar electrodes; some embodiments may be configured for mechanical functions without being enabled to deliver radiofrequency energy. These embodiments may further include various aspects of the technology disclosed herein, such as having a diameter that is no greater than about 5 mm, having a pinless rotation mechanism to open and close the jaws, or the jaws may include longitudinally aligned self-aligning features.

Some embodiments of an electrosurgical device include a blade that is capable of separating radiofrequency-sealed tissue into two portions. Embodiments of the blade maybe be positioned on a longitudinally disposed blade track; the blade may be positioned at home position at a proximal end of the track, at a distal end of the track, or at any point along the track between the distal and proximal ends of the track. In various embodiments of the device, when the jaws are in the open position, the proximal home position of the blade is configured such that the movement of the blade in a distal direction is prevented. In some embodiments, distal movement may be physically blocked by an impeding structure distal to the blade, in other embodiments distal movement may be prevented by a locking mechanism proximal to the blade.

On the other hand, when embodiments of the jaws are in the closed position, the proximal home position of the blade may be configured to allow distal movement of the blade, the first and second jaws collectively forming a clear through path to the distal end of blade track. The availability of the space for the through-path is, at least in part, due to the pinless aspect of the rotation mechanism in that the presence of a pin, for a pin-based jaw rotation mechanism, could otherwise occupy the space, and impede the path. The through path of the blade includes slots and clefts through various structures, as described below in the context of the figures. In typical embodiments of a blade of the configuration described, the blade is distal facing with a leading V-shaped notch, which cuts tissue as it is moved distally. At its proximal end, the blade is connected to a mechanical linkage in the handle that maintains it in a proximally biased position.

As noted above, dimensions of embodiments the electrosurgical device are important aspects of the technology, as embodiments of the device are intended to be compatible with trocars having an inner diameter of about 5 mm (in the conventional or commercial sense as described above). Thus, in particular embodiments, the set of jaws, when closed, has a diameter no greater than about 5 mm when the device is in an insertable configuration. An insertable configuration for a device with openable jaws is one, for example, in which the set of jaws is in a closed configuration, and wherein the jaws of the device are aligned with the longitudinal axis of the shaft. Thus, in particular embodiments of the technology described, the shaft has a diameter no greater than about 5 mm, and the set of jaws, when closed, provides a maximum diameter of about 5 mm.

Other dimensions and structural features of the technology are directed toward features and operational specifications of embodiments of the device that also need to accommodate the constraints imposed by the requirement for a 5 mm maximal diameter. For example, in particular embodiments, the jaws have a length of at least about 2.5 cm. Further, some embodiments of a 5 mm diameter constrained device that has jaws with a length of at least about 2.5 cm are able to exert a pressure in the range of about 14 lbs. to about 28 lbs. at the tip of the jaws, and in particular embodiments, the jaws are able to exert a pressure of at least about 16 lbs. at their tip.

One of the approaches to delivering high surgical performance from an electrosurgical device with 5 mm diameter constraint is to minimize the cross sectional area that is occupied by components or materials that do not provide distally projecting or contiguous structural support to the jaws, and particularly to support their ability to deliver sufficient closing force. Here are some examples of a material or component that could located in this region that do not lend distally projected support, or which interrupt longitudinal structural continuity in a portion of the cross sectional area of a device. One could consider a pin positioned orthogonally across a portion of the proximal aspect of the jaws, to be used, for example, as a structure upon which other features might pivot or rotate. A pin of this nature, while performing an operational role, does not strengthen the ability of the jaws to exert a compressive force, nor does it strengthen the ability of the jaws to maintain their position when the jaws encounter resistance provided by body structures within the laparoscopic operating space. Typical embodiments of provided device do not have a pin. Another example of a component occupying cross sectional area that does not provide distally projected structural support to the jaws relates to actuator members and electrically conductive members. Some embodiments of the provided device have connecting members that serve both a physical actuating function and an electrically conductive function, thus conserving cross sectional structural area. By these various aspects of embodiments of the device, the cross sectional fraction of the device that does not provide distally projecting structural support may be minimized.

Accordingly, with regard to a cross sectional slice taken through a portion of the device that includes the pinless rotation mechanism, in some embodiments of the device, a ratio of the structural material that contributes to supporting the set of jaws to the total cross sectional area of the device is at least about 82%. A similar analysis of distally directed structural support could make use of a volume-based constraint. For example, the central portion of the distal end of the device, at least the proximal aspect of the set of jaws, can include a given length of the shaft and/or jaws within proximal and distal boundaries. If that given length is multiplied by cross-sectional area within the set of distal and proximal boundaries, it may be understood that a measure of structural material can report structural material in terms of its volume and can be expressed as a percent of the total volume of the device portion within the boundaries.

As summarized above, some embodiments of the set jaws are configured in a manner such that the jaws self align with respect to their longitudinal axes when the jaws are approaching closure. Accordingly, in these jaw set embodiments, the tissue-engaging surfaces of each of the opposing jaws, respectively, have mutually complementary longitudinally oriented self-aligning features that prevent lateral slippage of jaws as they close toward each other. Inasmuch as these features prevent or correct incipient lateral slippage as the jaws close, these features may be characterized as longitudinally aligning and laterally stabilizing aspects of the tissue-engaging surfaces.

Embodiments of self-aligning jaw features may be disposed along the substantial entirety of the length of the jaws. In another aspect, embodiments of self-aligning jaw features may as occupy the substantial entirety of available tissue engaging surfaces of the jaws. In various embodiments, the self-aligning features may fully or substantially occupy the length tissue-engaging surfaces of the jaws; in other embodiments, the self-aligning features may occupy only a portion of the length of tissue-engaging surfaces of the jaws. The structural features associated with this approach to longitudinally aligning the jaws generally conserves on materials, costs, or dimensions, that would otherwise be associated with achieving manufacturing tolerances required to support a guarantee of collinear alignment of the two jaws when they close.

In particular embodiments, the self-aligning configuration of the tissue-engaging surfaces of the jaws includes a longitudinally aligned V-shaped projecting surface on one jaw and a complementary longitudinally aligned V-shaped receding surface or recession on the other jaw. In some embodiments, the V-shaped projection is on the lower jaw, and the V-shaped recession is on the upper jaw. The longitudinally aligned V-shaped projecting surface on one jaw and the complementary longitudinally aligned V-shaped receding surface on the other jaw, when the set of jaws is closed, form a V-shaped common interface with internal angle in the range of about 90 degrees to about 175 degrees. In particular embodiments, the V-shaped common interface has internal angle about 150 degrees.

In a more general aspect, the self-aligning configuration of embodiments of the tissue-engaging surfaces of the jaws, in a lateral cross section, form a zone or interface of tissue contact more complex than that of a single straight cross-sectional line. By virtue of being non-linear, the width of the contact zone between the closed jaws and the grasped tissue is greater than would be the tissue width of a linear tissue contact zone. Thus, the width of the tissue seal created by the V-shaped configuration of the tissue engaging surfaces of the jaws is greater than would be the width of a tissue seal created by flat tissue engaging surfaces. The arrangement just described, of complementary V-shaped projection and V-shaped recession forming a V-shaped zone of tissue being contacted by such jaws, is just one example of self-aligning tissue engaging surfaces.

In some embodiments of the technology, the electrosurgical device has an insulative layer applied over aspects of at least one of the opposing jaws, the insulative layer forming a spatial gap between the upper jaw and the lower jaw that prevents any direct electrical connection therebetween. In various embodiments, each jaw tip each has an electrically conductive surface on or within its tissue-engaging surface, and an aspect of the insulative layer includes strips aligned across the electrically conductive surface of at least one of the forcep tips. The strips farm a gap between the electrically conductive surfaces of the two jaws when the jaws are in a closed position. Such a gap is typically about 0.006 inch; more generally, the gap has a range of about 0.0045 inch to about 0.0075 inch. In various embodiments of the insulative layer, it may include a polymer, such as polyether ether ketone (PEEK), merely by way of example. In other embodiments, the insulative layer may include a ceramic material, such as any of alumina or alumina-titania, merely by way of example. Ceramic compositions can be advantageous for their relative hardness, incompressibility, and/or general durability. In some embodiments, the ceramic material is positioned at one or more sites on the surface of the device that are particularly subject to abrasive and/or compressive stress.

In some embodiments of the technology, the device includes a handle portion proximal to the shaft, a jaw actuator mechanism associated with the handle portion and configured to actuate a mechanical capability of the jaws, and a jaw actuator wire connected proximally to the actuator mechanism and connected distally to the set of jaws. In various embodiments, the mechanical capability of the jaws includes opening and closing the set of jaws. In some embodiments, the actuator wire is configured to actuate an opening and closing of the jaws by pivoting a second jaw with respect to at least a proximal piece of the first jaw, the proximal piece of the first jaw being fixed with respect to the shaft.

Further, in some embodiments, the same wire that serves as a mechanical actuator force transfer member is further configured to deliver RF energy to the jaws. From another perspective, embodiments of the device include an energy-delivery wire extending distally from the handle portion to the set of jaws. In some of these energy-delivery wire embodiments, the energy-delivery wire may be further configured to perform as an actuator of mechanical capability of the jaws, such as moving the jaws between an open and a closed position.

Some embodiments of the jaw actuator wire include a single wire in looped configuration that, in effect, forms a paired or double wire connection between the actuator mechanism and an attachment site on at least one of the jaws. In these embodiments, the looped wire has a distalmost looped terminal or turn around portion that is looped around its attachment site to one of the jaws. In embodiments wherein at least the proximal piece of the first jaw is fixed with respect to the shaft and the second jaw is pivotable with respect to the shaft, the actuator wire is attached to a proximal aspect of the second jaw.

In some embodiments, the actuator wire is configured as a push and pull mechanism, such that a distally-directed push from the wire moves the jaws to their open position, and a proximally-directed pull from the wire moves the jaws to their closed position. In some of these embodiments, the actuator wire is biased so as to support the jaws in their open position by virtue of a proximally directed pull by a spring associated with the jaw actuator.

In some embodiments, the jaw actuator includes a biasing member that maintains a push on the actuator wire, such push causing the jaws to have a default position of being held in the open position. Further, in some embodiments, the jaw actuator includes a manual lever that an operator may pull to effect a proximally-direct pull to close the jaws. Further still, in some of these embodiments, the actuator wire and connections associated with proximal and distal attachments of the wire are collectively configured to be able to operationally withstand between about 80 and about 120 lbs. of tension; in particular embodiments the actuator wire and its connections are configured to be able to withstand at least about 100 lbs. of tension.

In some embodiments of the device, each of the upper jaw and the lower jaw include a metal portion, and the entirety of each of these metal portions form an electrode. In other words, in some embodiments, there is no metal portion in either jaw that is not part of the electrode. In some embodiments, the device includes a single bipolar electrode pair, one electrode in each of the jaws. In these single bipolar pair embodiments, the electrodes are powered by a generator operating on a single radiofrequency channel. Other embodiments of the device may include a plurality of bipolar electrode pairs, and such plurality of bipolar electrode pairs may be controlled by a plurality of operating radiofrequency channels.

Some embodiments of the electrosurgical device include a shaft rotational actuator positioned proximal to the shaft; embodiments of the shaft rotator are typically associated with a handle portion of the device. In some embodiments, the shaft rotational actuator is configured to be able to rotate freely in both clockwise and counter clockwise directions, such rotation of the actuator being directly translatable to rotation of the shaft, and in turn, rotation of the set of jaws about their longitudinal axis. Free rotation in this context, whether in reference to a shaft rotator, the shaft, or the jaws, per embodiments of the technology, refers to a rotation that may occur indefinitely in either direction, without a stop, and without a change of direction. Further, per embodiments of the technology, rotation may freely occur without consequence or compromise with regard to any mechanical or electrical capability of embodiments of the electrosurgical device.

In some embodiments of the electrosurgical device, the set of two opposing jaws (including a first jaw and a second jaw) is configured such that the jaws can open to an angle in the range of about 30 degrees to about 40 degrees. In some the set of two opposing jaws is configured such that when the set is moving from an open position toward the closed position, a first point of mutual contact between the two jaws occurs at a distal end of each jaw. The set of jaws may be further configured such that after the first point of mutual contact has been made and as the set moves further toward a closed position, a distal pivotable piece of the first jaw pivots within a plane of its longitudinal axis such that the proximal end of the first jaw comes into contact with the proximal end of the second jaw.

In some embodiments, the set of two opposing jaws is configured such that when the set of jaws is moving from an open position toward the closed position, a first point of mutual contact between the two jaws occurs at a distal end of each jaw. In some of these embodiments, after the first point of mutual contact has been made and the jaw set is then moving further toward a closed position, a distal pivotable piece of the first jaw pivots within a plane of its longitudinal axis such that the proximal end of the first jaw comes into contact with the proximal end of the second jaw.

Some embodiments of the device and its dynamics of closing may be understood in terms of the response of the jaws to the presence of target tissue within the grasp of closing jaws. In some embodiments, for example, the set of jaws may be configured such that when the set is moving toward the closed position and has made an initial contact with the target tissue, a pivotable piece of the first jaw then pivots in response to the presence of the target tissue as the jaws move further toward the closed position to grasp the tissue. The pivoting of the pivotable jaw piece may effect a substantially equivalent distribution of pressure along the grasped piece of the target tissue, particularly in comparison to the unequal distribution of pressure that may occur in the absence of such intra-jaw pivotability. In a related aspect of the device, the pivotable jaw piece is configured to pivot toward a parallel relationship with the second jaw.

In various embodiments, the pivotable jaw piece may be configured such that it can pivot around its pivotable connection within an arc having pivotable range that varies between about 2 degrees to about 8 degrees. In particular embodiments, the pivotable jaw piece may be configured such that it can pivot around its pivotable connection within an arc having a pivotable range of about 6 degrees. In another aspect, the pivotable jaw piece has an arc of a given pivotable range and is biased such that a distal tip of the first jaw is canted toward the second jaw within the arc of pivotable range.

In some embodiments, the first jaw includes a proximal jaw piece fixed with respect to the shaft, a pivotable distal jaw piece, and a pivotable assembly that connects the proximal jaw piece and distal jaw piece. In various of these embodiments, the pivotable assembly may be positioned longitudinally at a substantially central site on the distal piece. In some of these embodiments, a tissue engaging surfaces comprises the substantial entirety of the distal and pivotable piece of the first jaw. Accordingly, a central location on the distal piece of the jaw also represents a central location with respect to a tissue-engaging surface of the jaw. In another aspect of some embodiments, the substantial entirety of the tissue engaging surface of the distal piece of the first jaw comprises an electrode. Thus, a central site on the distal piece of the first jaw represents a central site on the electrode. The centrality of the site of the pivotable assembly on the distal and pivotable jaw piece may be related to ability of the distal piece to pivot in such a manner so as to evenly distribute pressure across the surface target tissue as the jaws close on the tissue. In some of these embodiments, the pivotable assembly may include a laterally projecting boss on each of both sides of the distal pivotal jaw piece and an internally accessible receptacle on each of both sides of the proximal fixed jaw piece, the laterally projecting bosses and the internally accessible receptacles being mutually compatible. Other arrangements and configurations that support a pivoting capability such as that described and depicted herein are known in the art, and are be considered to included in the scope of the present technology.

In some embodiments of the device, with reference to a method of fabrication, the proximal and distal pieces of the two-piece jaw may be assembled in a snap fit manner. More particularly, in such embodiments, the fixed proximal jaw piece is sufficiently flexible that it can deflect to allow the insertion of the laterally projecting bosses of the distal pivotable jaw piece in a snap fit manner.

Another aspect to the pivoted bias of the distal and pivotable piece of a two-piece jaw relates to a biasing member that maintains the pivotable piece in a default pivot position. In some embodiments, for example, the distal pivotable piece of the first jaw includes a biasing member that is configured to press against a shelf of the proximal jaw piece, and by such pressing bias the distal pivotable piece of the first jaw such that the distal tip of the distal pivotable piece is canted toward the second jaw. With more particularity, in some of these embodiments, the biasing member takes the form a leaf spring positioned in a recess within the distal pivotable piece on an aspect of the distal pivotable piece that faces the fixed proximal piece of the first jaw.

In another aspect, the technology provides a surgical device having a set of opposing jaws disposed distal to a shaft, the set of jaws having a first jaw and a second jaw. Each of the opposing jaws has a longitudinal axis and a tissue-engaging surface, and the tissue-engaging surface of each jaw may have a complementary self-aligning configuration with respect to the longitudinal axis of the other jaw. In some embodiments of the provided surgical technology, the set of jaws, when closed, has a diameter no greater than about 5 mm, and the shaft has a diameter no greater than about 5 mm. Embodiments of the surgical device may further include a pinless rotation mechanism formed from rotatably cooperative features of the first jaw and the second jaw. This pinless rotation mechanism enables the set of jaws to pivot between an open position and a closed position. The pinless rotation mechanism is configured such that the pinless rotation mechanism creates a common center of rotation that is not necessarily positioned at a point on a line corresponding to a central longitudinal axis of the shaft.

Embodiments of the technology further relate to a method of electrosurgical sealing in a laparoscopic environment. The method may include moving a set of jaws of an electrosurgical instrument into a proximity of the target tissue, the set of jaws comprising a first jaw and a second jaws. More particularly, moving toward an electrosurgical site may include advancing a distal portion of an electrosurgical device into a patient through an in-place trocar having an internal diameter of about 5 mm. The distal portion of the electrosurgical device, in this circumstance, includes a distal aspect of a shaft and the set of jaws, including a first jaw and a second jaw, that are positioned on a distal end of the shaft. Embodiments of the method may include moving the jaws between an open position and a closed position. Moving the jaws between an open position and a closed position opening may include rotating cooperative structures of the first jaw and the second jaw, the first and second jaws not being connected by a pin. Moving the jaws to a closing position may further include grasping the target tissue with the jaws. The method may still further include delivering radiofrequency energy to the target tissue from the jaws.

In some embodiments of the method, moving the set of jaws into a proximity of the target tissue further includes rotating the jaws around their central longitudinal axis. Rotating the jaws may occur by way of rotating the shaft of the device around its central longitudinal axis. Rotating the shaft of the device may occur by rotating a shaft rotation actuator proximal to the shaft. In various embodiments of the method, embodiments of the shaft rotation actuator, the shaft, and the jaws may all have the capability of rotating freely in both clockwise and counter clockwise directions without a stop, or a need to reverse direction.

In some embodiments of the method, moving the jaws between an open position and a closed position opening includes rotating cooperative structures of the first jaw and the second jaw at their respective proximal ends, the first and second jaws not being connected by a pin. Moving the jaws between an open position and a closed position opening may include pivoting the jaws with respect to each other around a center of rotation that is not necessarily on a line corresponding to a central longitudinal axis of the shaft. In some embodiments, moving the jaws between an open position and a closed position opening includes pivoting the jaws around a center of rotation that is not on a line corresponding to a central longitudinal axis of the shaft, and in some embodiments, the center of rotation may be displaced to a position beyond the diameter of the shaft.

In another aspect, moving the jaws between an open position and a closed position opening may include at least a proximal piece of a first jaw remaining fixed with respect to the shaft and a second jaw pivoting with respect to the shaft. In some of these embodiments, moving the jaws to the closed position may included a distal piece of the first jaw pivoting with respect to the proximal piece of the jaw, and thus pivoting with respect to the shaft. In some embodiments, the pivoting of the distal piece of the first jaw with respect to the shaft includes the distal end of the distal piece pivoting away from the second jaw and the proximal end of the distal piece pivoting toward the second jaw.

In some embodiments of the method, moving the jaws to a closed position includes pivoting a distal piece of the first jaw from a pivotable connection that is positioned at a substantially central portion of the distal piece. In some aspects of the method, there is an interaction between the jaws as they are closing and the target tissue that the jaws are closing around. Thus, in some embodiments, pivoting the distal piece of the first jaw includes pivoting in response to the presence of the target tissue between the jaws, in such a manner that distributes pressure with substantial equivalence along the grasped portion of the target tissue. Further, pivoting a distal piece of a first jaw from a connection positioned at a substantially central portion of the distal piece comprises pivoting in response to the presence of the target tissue between the jaws, thereby allowing the distal piece of the first jaw to pivot toward a parallel alignment with respect to the second jaw.

In some embodiments of the method, moving the jaws to a closed position includes mutually aligning the respective central longitudinal axes of the first and second jaws. In instances when the jaws are moving to a closed position so as to grasp tissue, moving the jaws to a closed position may include mutually aligning the respective central longitudinal axes of the first and second jaws comprises in such a manner so as to resist a misaligning effect of target tissue have on the jaws as they are closing.

In some embodiments of the method, moving the jaws to a closed position comprises grasping the target tissue with a force in a range of about 14 lbs. to about 28 pounds. Further, in some embodiments, moving the jaws to a closed position includes grasping a portion of target tissue of up to about 2.5 cm in length.

In some embodiments of the method, opening and then closing the jaws includes transferring a force from a mechanical actuator to the jaws via an actuator wire. In some of these embodiments, closing the jaws includes pulling the actuator wire in a proximal direction, and in some embodiments, opening the jaws pushing the actuator wire in a distal direction. In some embodiments of the method, delivering radiofrequency energy to the target tissue may include delivering energy to the jaws via the actuator wire.

In some embodiments of the method, moving the jaws to a closed position includes moving the jaws toward a closed position in a manner such that a first point of mutual contact between the two jaws occurs at a distal end of each jaw. In some of these embodiments, moving the jaws to a closed position after the point of first mutual contact has occurred includes pivoting a distal pivotable piece of a first jaw within a plane of its longitudinal axis such that the proximal end of the first jaw comes into contact with the proximal end of the second jaw.

In some embodiments of the method, delivering radiofrequency energy to the target tissue includes energy through a wire that is further enabled to perform a mechanical function, such as actuating the jaws between an open and closed position. In various embodiments of the method, electrosurgically treating tissue particularly includes sealing edges of target tissue together.

In some embodiments of the method, after delivering radiofrequency energy to the target tissue, the method further includes separating newly sealed target tissue into two sealed tissue segments. In various embodiments, separating newly sealed target tissue into two sealed tissue segments includes advancing a blade distally through sealed target tissue.

Some embodiments of the method include electrosurgically treating more than one site during a single procedure, or treating a lengthy target site with a series of sealing maneuvers. Thus, some embodiments of the method further include identifying a second target site and then repeating the steps of grasping and delivering energy, the steps being directed toward the second target site.

BRIEF DESCRIPTION OF THE DRAWINGS

FIG. 4D is a perspective view of a blade isolated from the shaft and jaws.

FIG. 12A is a proximal-looking perspective view of an embodiment of distal tips of a closed set of jaws of an electrosurgical device, the distal tips aligned by complementary longitudinal aligning features, a V-shaped projection on the lower jaw, and a V-shaped recession on the upper jaw.

FIG. 12B is a proximal-looking front view of an embodiment of the distal tips of a closed set of jaws of a laparoscopic electrosurgical device, the distal tips aligned by complementary longitudinal aligning features, a V-shaped projection on the lower jaw, and a V-shaped recession on the upper jaw.

FIG. 12C is a proximal-looking perspective view of a distal aspect of an electrosurgical device, with a set of jaws in an open position showing complementary longitudinal aligning features, a V-shaped projection on the lower jaw, and a V-shaped recession on the upper jaw, as well as a central longitudinally-oriented gap in both V-shaped surfaces that form a through passage for a blade that is distally advanceable when the jaws are in a closed position.

FIG. 15B is a top perspective view of an embodiment of an upper jaw of an electrosurgical device that shows points of ceramic overlaying the electrode at abrasive stress points as they are embedded in a more extensive polymer layer.

DETAILED DESCRIPTION OF THE INVENTION

Figure 1A:
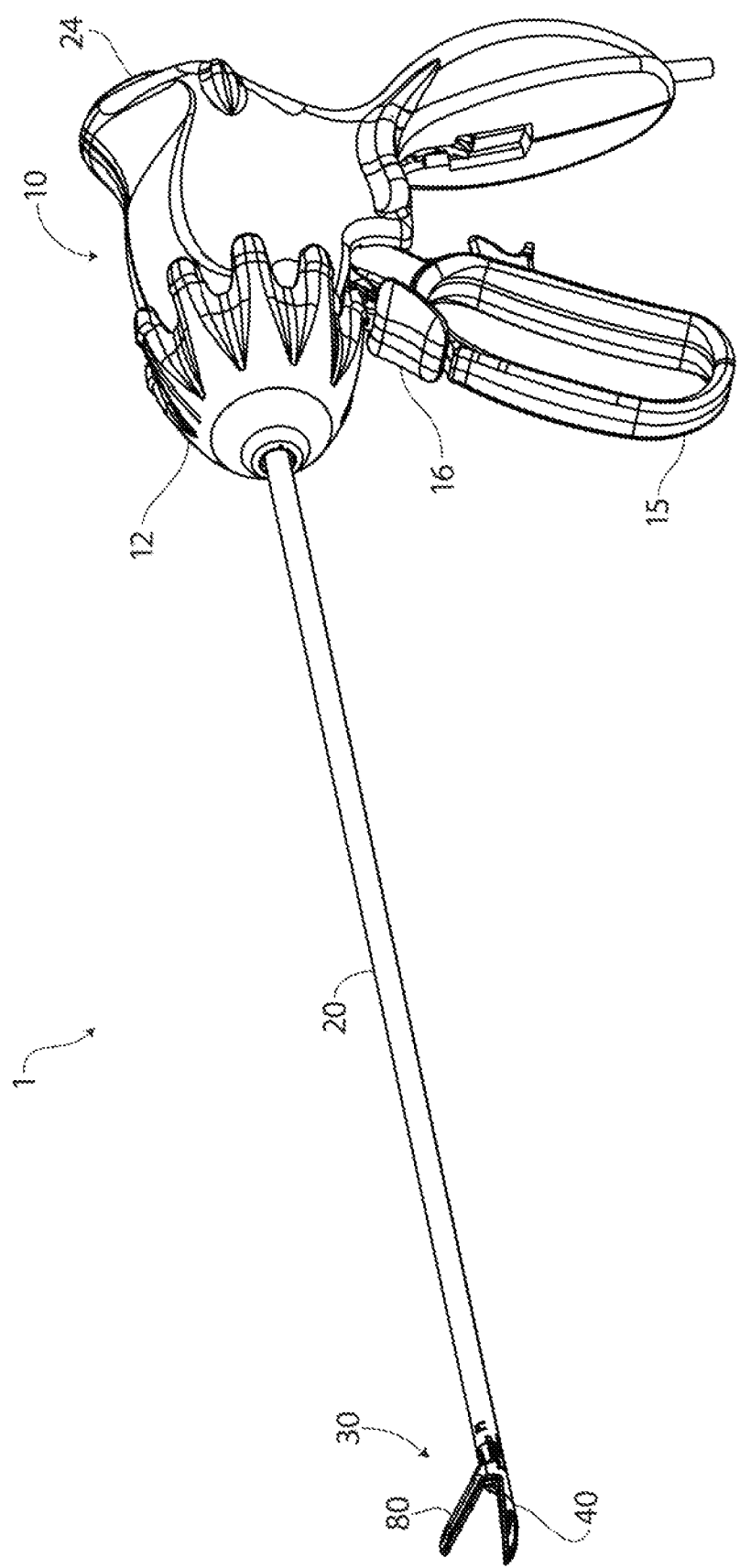
FIG. 1A is a perspective view of an embodiment of a laparoscopic electrosurgical device.

Embodiments of the technology described herein provide various improvements over available electrosurgical devices, such improvements permitting a physical downsizing of a device to a dimension that permits practical use of an electrosurgical device within the constraints of a laparoscopic surgical environment. One of these constraints to working laparoscopically relates to the 5 mm inner diameter opening provided by a commercially standard trocar. A device compatible with the 5 mm opening constraint needs to have an insertable configuration with a maximal diameter that is insertable therethrough. These technological improvements are generally directed toward creating a high degree of efficiency with regard to performance of the device per unit volume or cross sectional area. For example, a jaw set of a disclosed device, in spite of small physical dimension, is able to deliver an appropriate level of force to tissue being clamped by the jaws, and the structure and material of the jaws have sufficient strength to maintain integrity during the delivery of such force.

In one aspect, the technology includes maximizing the amount of structural material in particular areas as a percent of total amount of device material. The proximal aspect of the jaw set, for example, includes various components, some that contribute structural support for the jaws, and other components that perform other functions, such as mechanical or electrical functions. The technology, in this aspect, is directed toward minimizing cross sectional area or volume that does not directly support the jaws. Some components of conventional electrosurgical devices are typically dedicated to a single use, such as electrodes, power lines, or actuator lines; in contrast, various components of embodiments of the presently disclosed device do double duty both as structural and electrical components in embodiments of the technology. In another example of material and occupied volume efficiency, some structural components, such as a pin connecting two jaws at their base, are eliminated and replaced by a pinless mechanism that links upper and lower jaws of a jaw set together.

Aspects of the technology in the form of embodiments of the disclosed electrosurgical device and methods of using the device are illustrated in FIGS. 1-16D. With regard to Embodiments A and B, as described above, the majority of the figures depict examples of Embodiment A, or they relate to aspects of the technology that are common to both Embodiments A and B. FIGS. 5A-5C particularly depict examples in accordance with Embodiment B. It should be understood that in any reference to a lower jaw or an upper jaw when describing the figures is for a convenient visual reference with respect to a conventional positioning of the rotatable jaws, and that the two jaws could be more generally referred to as a first jaw and a second jaw. Further, with respect to orientation of the figures, in general a distal end of a device is on the left, and a proximal end of a device is on the right.

Figure 1B:
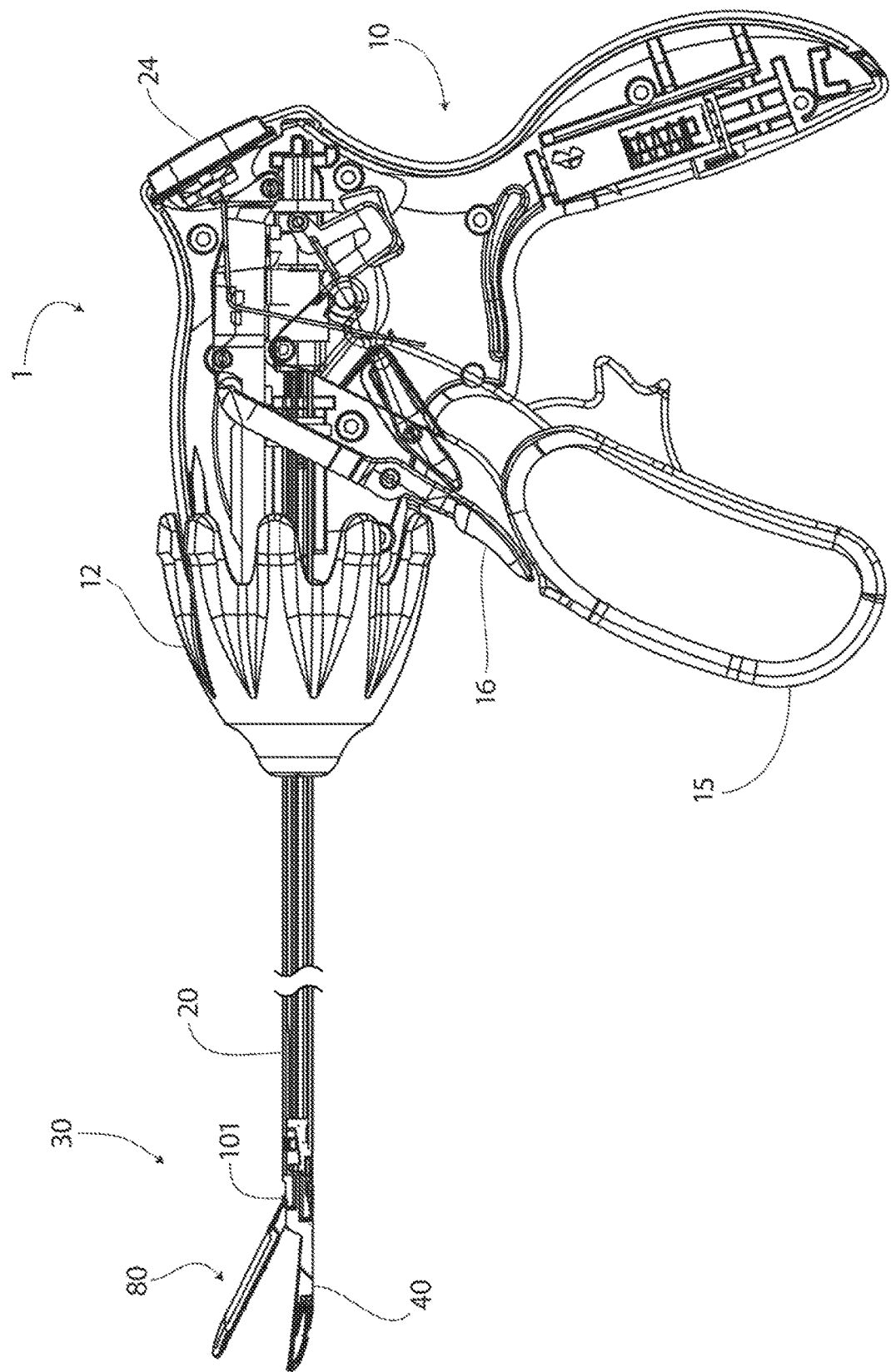
FIG. 1B is a side view of an embodiment of an electrosurgical device with the jaws in an open position.

FIGS. 1A-1D provide various views of embodiments of a laparoscopic electrosurgical device as a whole. FIG. 1A is a perspective view of an embodiment of an electrosurgical device 1 as provided herein, with a set of jaws 30 in an open position. FIG. 1B is a side view of an embodiment of an electrosurgical device 1 with the jaws 30 in the same open position as in FIG. 1A. A handle 10 supports a jaw actuator grip 15 and blade actuator lever 16, and a shaft rotator 12. A shaft 20 extends distally from the handle, and supports an end effector such as a set of jaws 30 at its distal end. In the embodiments described and depicted herein, the end effector takes the faun of a forceps or pair of jaws 30, with a first law or lower jaw 40 and a second jaw or upper jaw 80. A pinless rotation assembly or mechanism 101 operates pivoting of the jaws between an open position and a closed position.

The shaft rotator 12 is configured to move freely in both clockwise and counterclockwise directions, and in so moving, rotates the shaft around its longitudinal axis. Rotation of the shaft translates into rotation of the end effector 30 around its longitudinal axis. The jaw actuator grip 15 is operably connected to end effector 30 by an actuation wire disposed within the shaft, which is configured to open and close the jaws. The actuation wire is configured as a push and pull mechanism, where in a push of the wire opens the jaws and a pull on the wire closes them. A biasing mechanism within the handle at the proximal end of the wire maintains a distal-ward bias that pushes the wire, maintaining the jaws in a default open position. A proximal pull on the jaw actuator grip 15 pulls the actuator wire proximally, causing the jaws to pull. The jaw actuator grip is lockable in its proximally pulled position, thereby locking the jaws in a closed position. A second pull on the jaw actuator grip releases the lock, thereby allowing the jaws to open. The blade actuation lever 16, positioned in this embodiment distal to the jaw actuator grip, is connected by mechanical linkage to a blade disposed within the shaft. A pull on the blade actuation lever moves the blade forward distally, to effect a separation of tissue after it has been sealed by radiofrequency energy delivered to the tissue by bipolar electrodes within the set of jaws. A radiofrequency on/off button 24 is positioned at an upper proximal site on the handle.

Figure 1C:
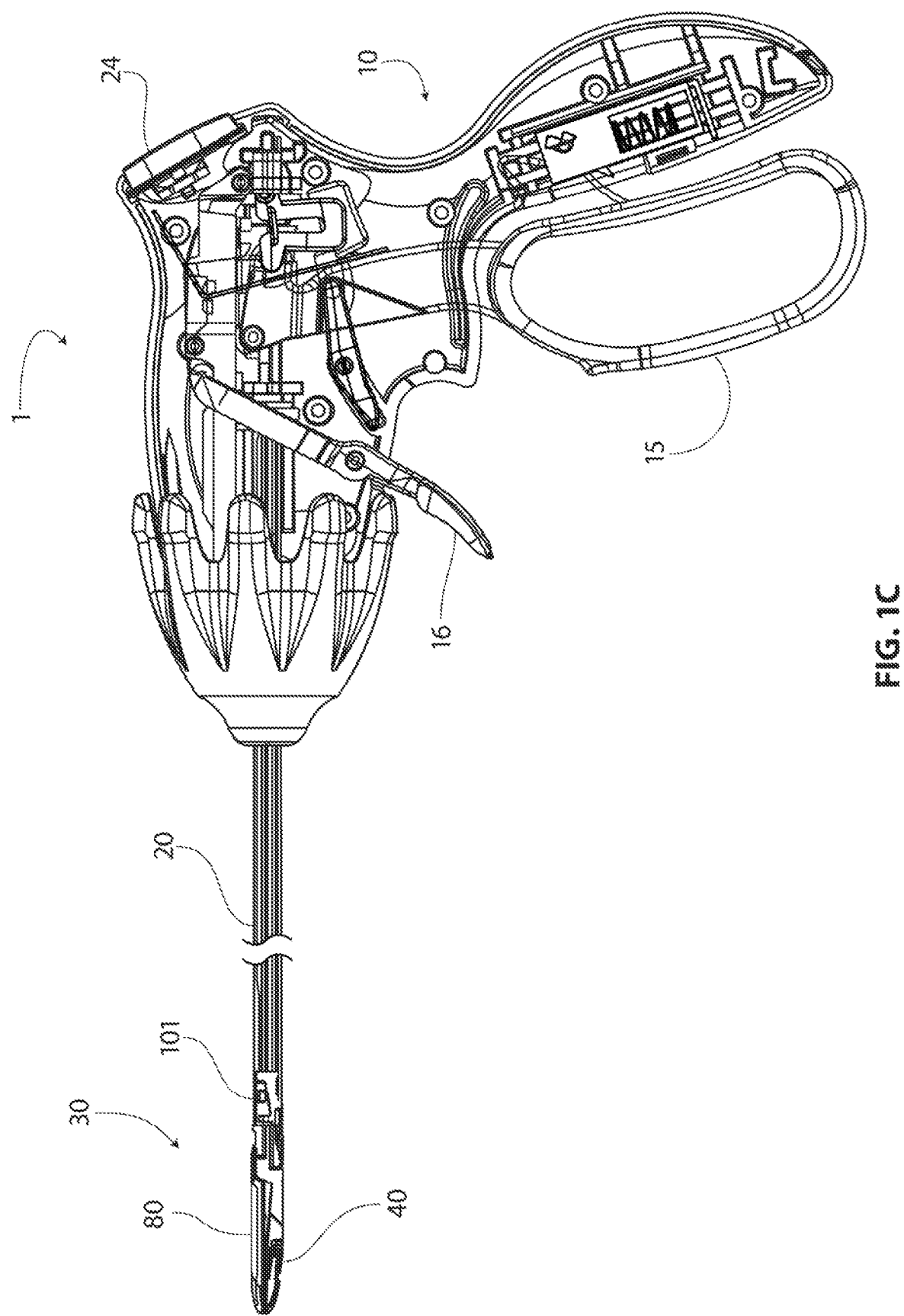
FIG. 1C is a perspective view of an embodiment of an electrosurgical device with the jaws in a closed and locked position, and with the blade in a retracted in proximal position.
Figure 1D:
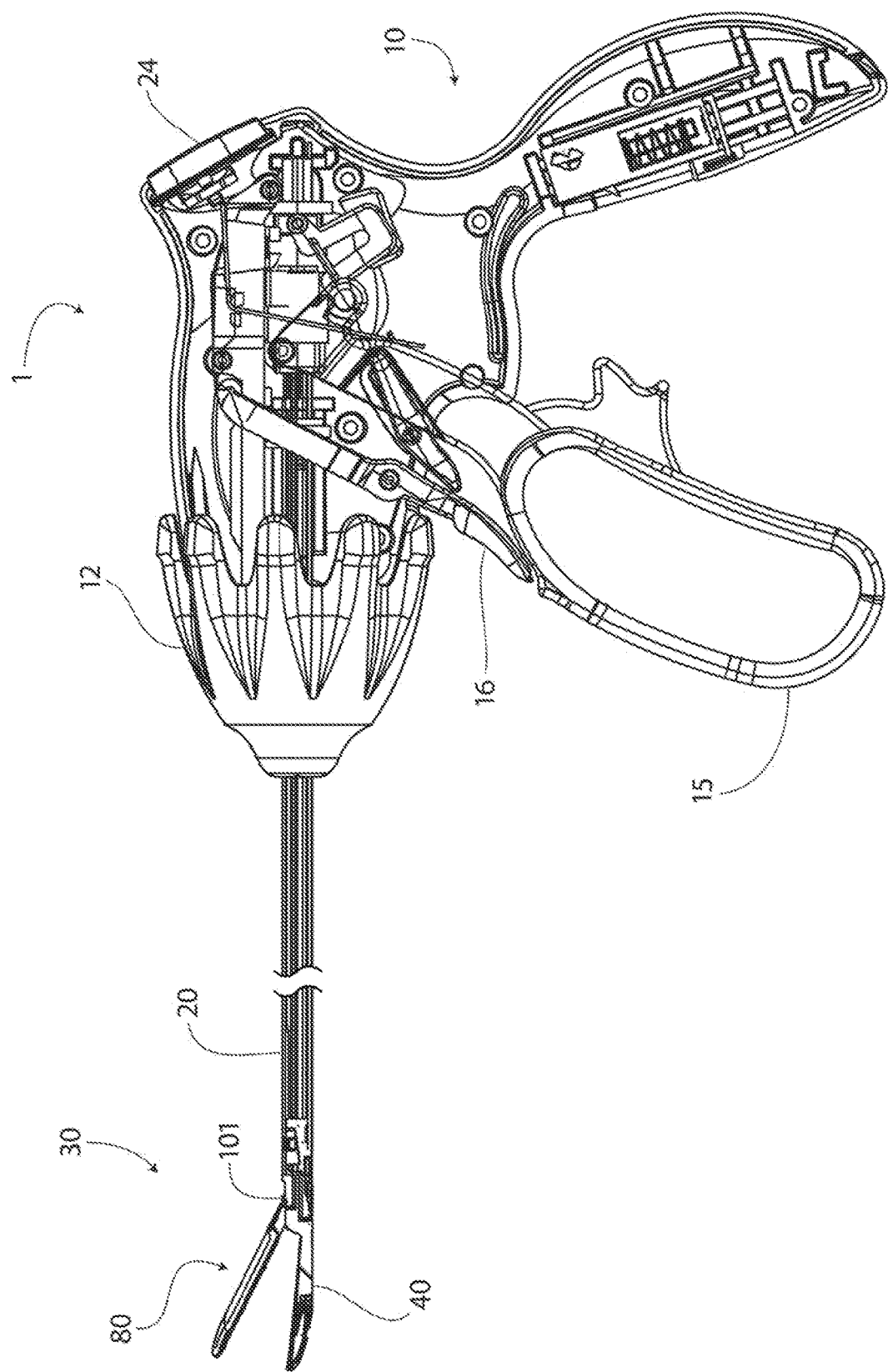
FIG. 1D is a perspective view of an electrosurgical device with the jaws in a closed and locked position, and with the blade in a distally advanced position.

FIG. 1C is a perspective view of an embodiment of an electrosurgical device 1 with the jaws 30 in a closed and locked position, and with the blade in a retracted in proximal position. FIG. 1D is a perspective view of an electrosurgical device 1 with the jaws 30 in a closed and locked position, and with the blade in a distally advanced position. The blade itself, is not visible in these figures, but the forward position of the depicted blade actuator lever 16 in FIG. 1C is indicative of the blade being in a retracted or home position, and the pulled back position of the blade actuator lever in FIG. 1D is indicative of the blade being in a forward position. FIG. 1C also shows the jaw actuator grip in a pulled back position, locked into the main handle piece 10. In this position, and typically only in this position, is the blade actuator lever free to be pulled back so as to advance the blade distally.

Embodiments of electrosurgical devices, as described herein, may be configured such that the (1) provision of radiofrequency energy delivery to seal tissue portions and (2) the movement of the blade to sever or separate sealed tissue portions are separate and independent operations. Distal movement of the blade from its proximal home position is typically allowed only when the jaws are closed and in a locked position, the locking occurring by way of engagement between the jaw actuator grip and elements within the handle. (As described further below, in the context of describing FIG. 4A, a jaw-based blocking system also operates to prevent distal movement of the blade when the jaws are closed.) Once the jaws are in such a locked position, the blade is free to move through its full range of proximal to distal movement. Although the blade is free to move when the jaws are closed and locked, its default and biased position is its proximal home position; pressure from blade actuator lever 16 needs to be maintained in order for the blade to remain at its most distal position. Further detail related to the distal movement of the blade is provided below in the context of FIGS. 4A-4D.

Figure 2A:
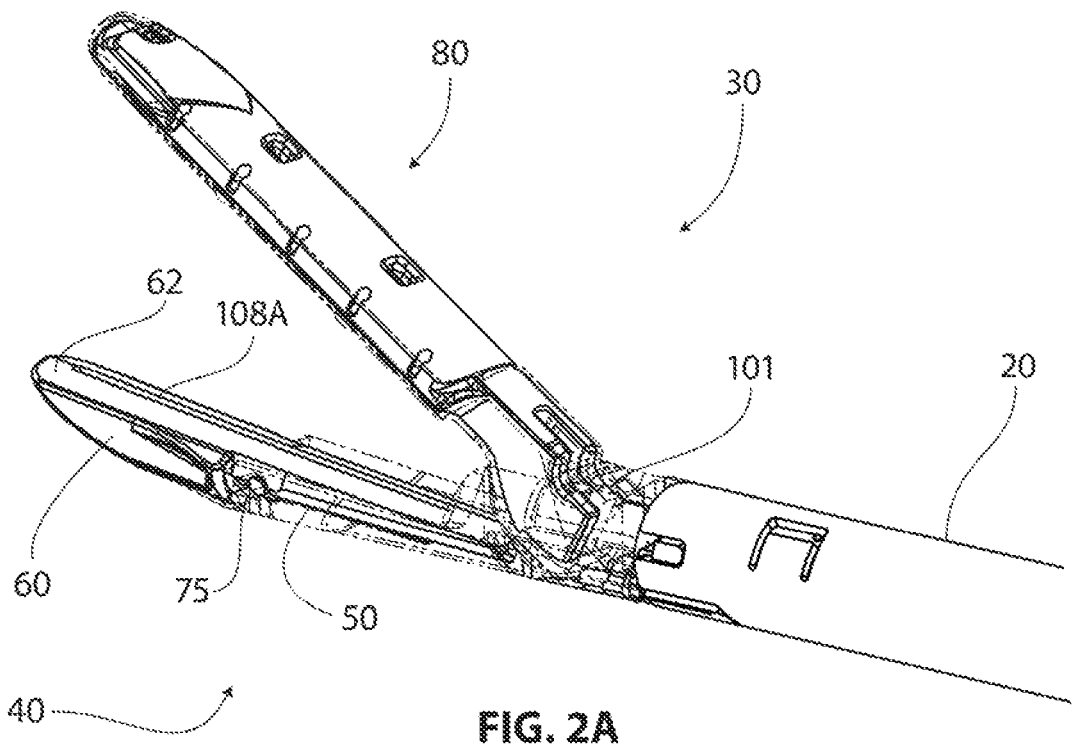
FIG. 2A is a transparent perspective view of an embodiment set of jaws of an electrosurgical device, with the jaws in an open position.
Figure 2B:
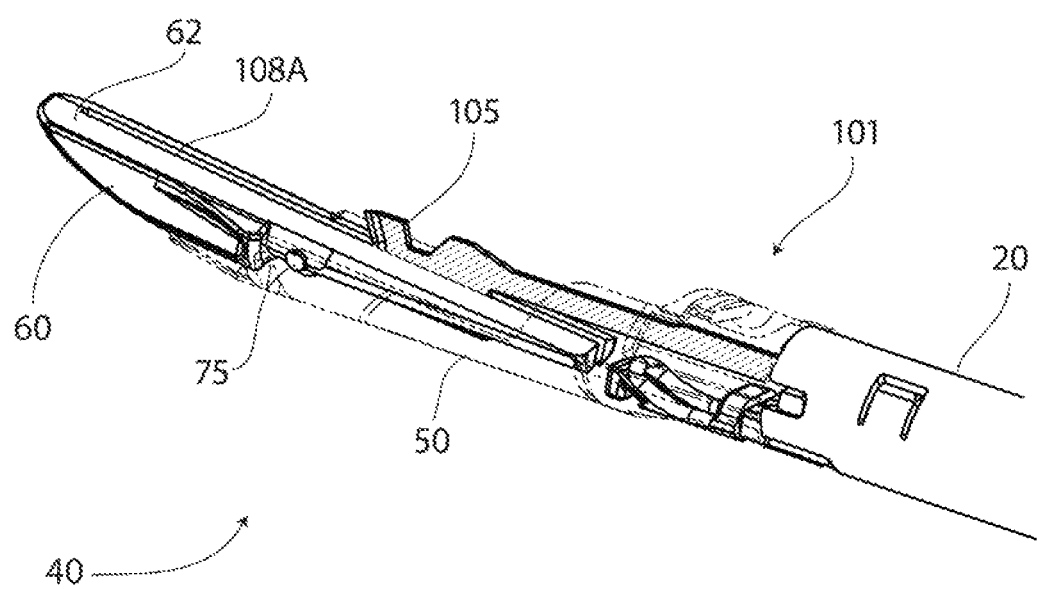
FIG. 2B is a transparent perspective view of an embodiment of a lower jaw of a set of jaws an electrosurgical device, with a blade moved distally to a position about half way to its distal stop point.

FIGS. 2A and 2B provide similar transparent views of embodiments of a set of jaws 30 in an open position; these figures show a pinless rotation mechanism or assembly 101 that comprises proximal aspects of both the lower jaw 40 and the upper jaw 80. FIG. 2A is a transparent perspective view of a set of jaws of laparoscopic electrosurgical device in an open position, with a blade 105 disposed in a proximal or home position within a proximal space in the jaws, and extending further into a distal portion of the shaft. FIG. 2B is a transparent perspective view of a lower jaw of set of jaws of laparoscopic electrosurgical device with a blade moved distally to a position about half way to its distal stop point.

An embodiment of a pinless rotation assembly 101, as shown in FIGS. 2A and 2B includes a first arcuate track portion 85 of upper jaw 80 and a second arcuate track portion 45 of lower jaw 40. Aside from the specific structures that comprise rotation assembly, identifier 101 in figures generally designates a junctional region of the devise that includes the proximal aspects of both upper and lower jaws. Because of the transparency of the drawing, arcuate track 45 of lower jaw 40 is difficult to see; it is shown in greater solid detail in further figures. Arcuate track 85 of upper jaw 80 is rendered as a solid. Further visible in these figures is the surface of an electrode tray or bipolar electrode 62, within the pivotable portion 60 of lower jaw 40. Blade track or passageway 108A is centrally disposed within electrode 62. A companion facing half of the full blade track is similarly disposed (not visible) within the electrode portion of upper jaw 80.

Figure 3A:
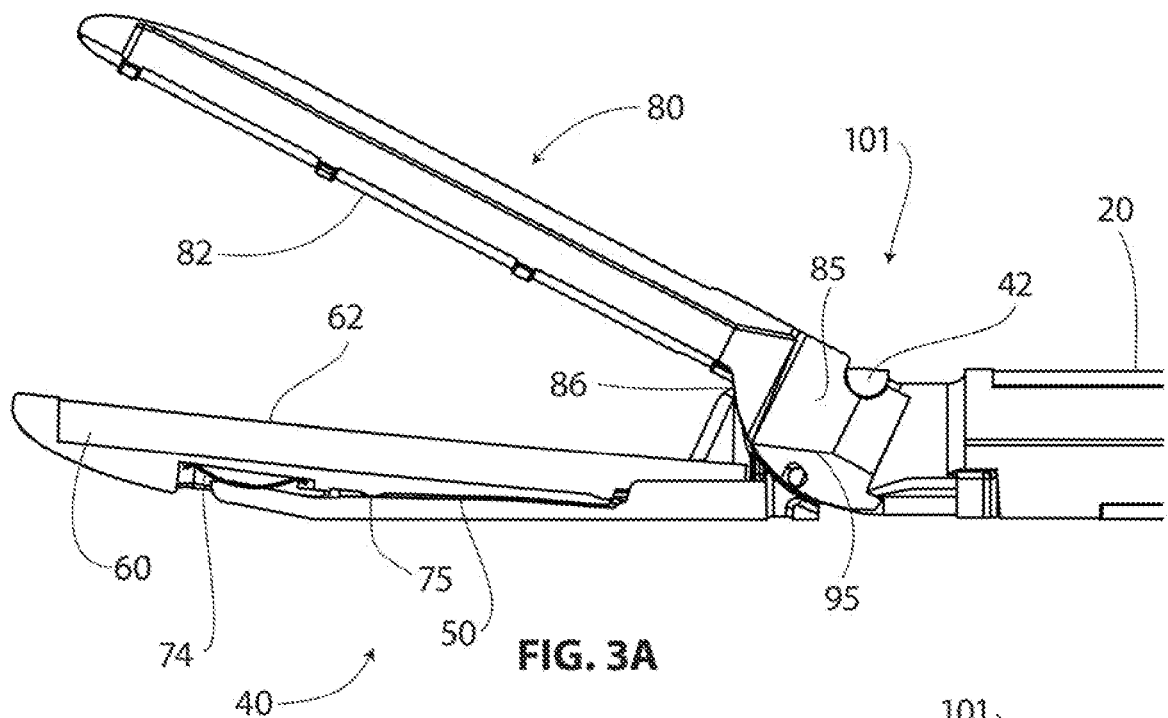
FIG. 3A is a side view through the longitudinal midline of an embodiment of a set of jaws of an electrosurgical device, with the jaws in an open position.
Figure 3B:
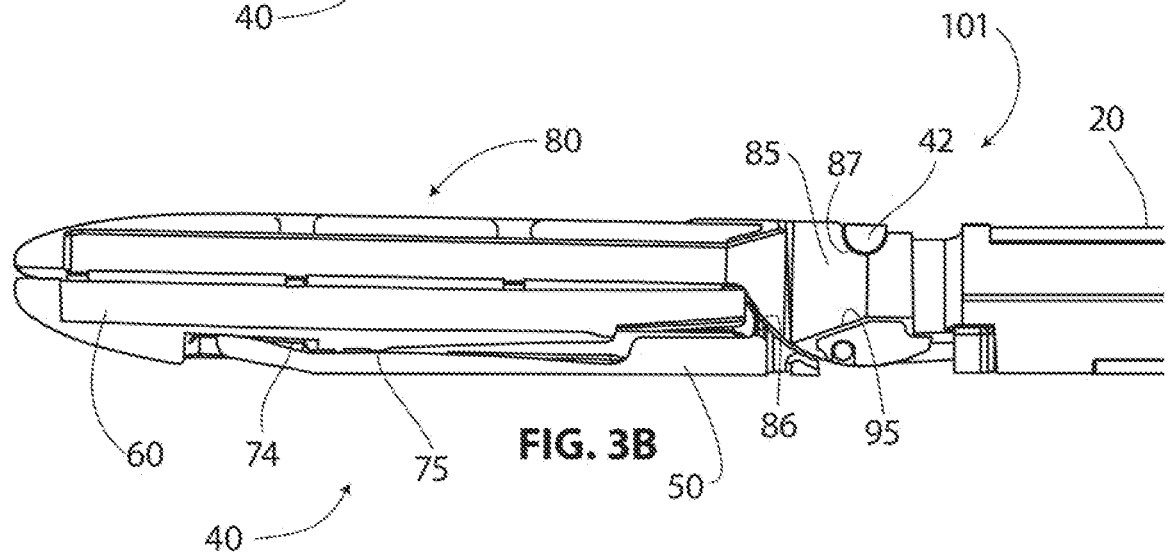
FIG. 3B is a side view through the longitudinal midline of an embodiment of a set of jaws of an electrosurgical device, with the jaws in a closed position.
Figure 3C:
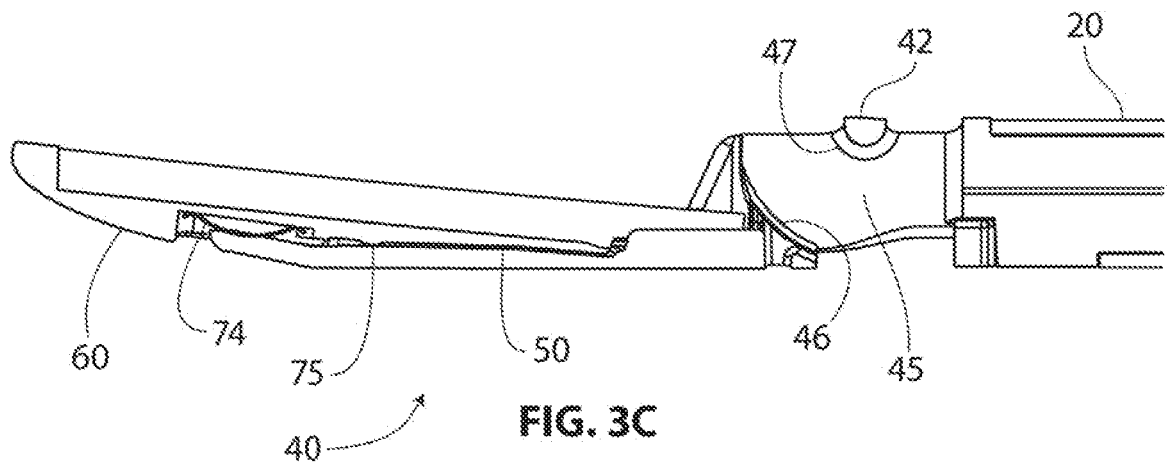
FIG. 3C is a side view through the longitudinal midline of an embodiment of a lower jaw of a set of jaws an electrosurgical device.

FIGS. 3A-3C provide a side views through the longitudinal midline of an embodiment of a set of jaws of a laparoscopic electrosurgical device; the blade is not shown in these views. FIG. 3A shows the jaws in an open position; FIG. 3B shows the jaws in a closed position. FIG. 3C shows the lower jaw 40 in isolation, without the upper jaw. FIGS. 3A-3C collectively focus on an embodiment of a pinless rotation assembly 101 that joins upper jaw 80 and lower jaw 40 together, and allows the jaws to pivot with respect to each other. More specifically, pinless rotation assembly 101 allows the upper jaw to pivot with respect to the proximal base portion 50 of lower jaw 40. Notably, the rotation assembly does not include a through pin. More particularly, these figures focus on arcuate track portions of both jaws that cooperate to allow the jaws to open and close. A first arcuate track 45 is formed on a proximal aspect of a proximal portion 50 of lower jaw 40. A second arcuate track 85 is formed on a proximal aspect of upper jaw 80. FIG. 3C shows the lower jaw 40 in isolation unimpeded by the intervening appearance of upper jaw, and provides the best view of a first arcuate track 45, with its upper and smaller concentric surface 47 and lower and larger concentric surface 46.

Both of the first and second arcuate tracks include concentric surfaces, one surface smaller and more central to the other, and the other surface larger and more peripheral to the other. First arcuate track 45 of lower jaw 40 (more particularly of proximal portion 50 of lower jaw 40) has a larger concentric engagement surface 46 on its lower aspect, and it has a smaller concentric surface 47 on its upper aspect. Second arcuate track 85 of upper jaw 80 has a larger concentric engagement surface 86 on its lower aspect, and it has a smaller concentric surface 87 on its upper aspect. As a whole, second arcuate track 85 (of upper jaw 80) is generally contained within an enclosure provided by first arcuate track 45 (of lower jaw 40). The first and second arcuate tracks are dimensioned such that the second arcuate track can freely rotate within first arcuate track. The two larger concentric surfaces, i.e., the lower surface 46 of the lower jaw and the lower surface 86 of the upper jaw are complementary. And the two smaller concentric surfaces, i.e., the upper surface 47 of the lower jaw and the upper surface 87 of the upper jaw are complementary.

A detail of both first and second arcuate tracks, not seen in FIGS. 3A-3C since they are side views, is that they arcuate track includes a central slot to accommodate through passage of a blade 105. Aspects of the arcuate tracks and the blade through path may be seen in FIGS. 6 and 12 and will be described further below. The arrangement of complementary surfaces, and the enclosure of the second arcuate track within the first arcuate track permit the pivoting of the upper jaw 80 with respect to lower jaw 40. A retaining strap 42 of the proximal portion 50 of lower jaw 40 is arranged laterally across the top of the upper and smaller concentric surface 87. Retaining strap 42 securely retains the second arcuate track within the first arcuate track such that it cannot be lifted from within its enclosure.

Also shown in FIGS. 3A-3C is the site of a pivotable connection 75 between distal jaw piece 60 and proximal jaw piece 50; aspects of pivotable connection 75 are described below in the context of FIGS. 7A-7C. Further shown in FIGS. 3A-3C is a biasing member 74, which is described below in the context of FIG. 9D and FIGS. 11A-11B.

Figure 4A:
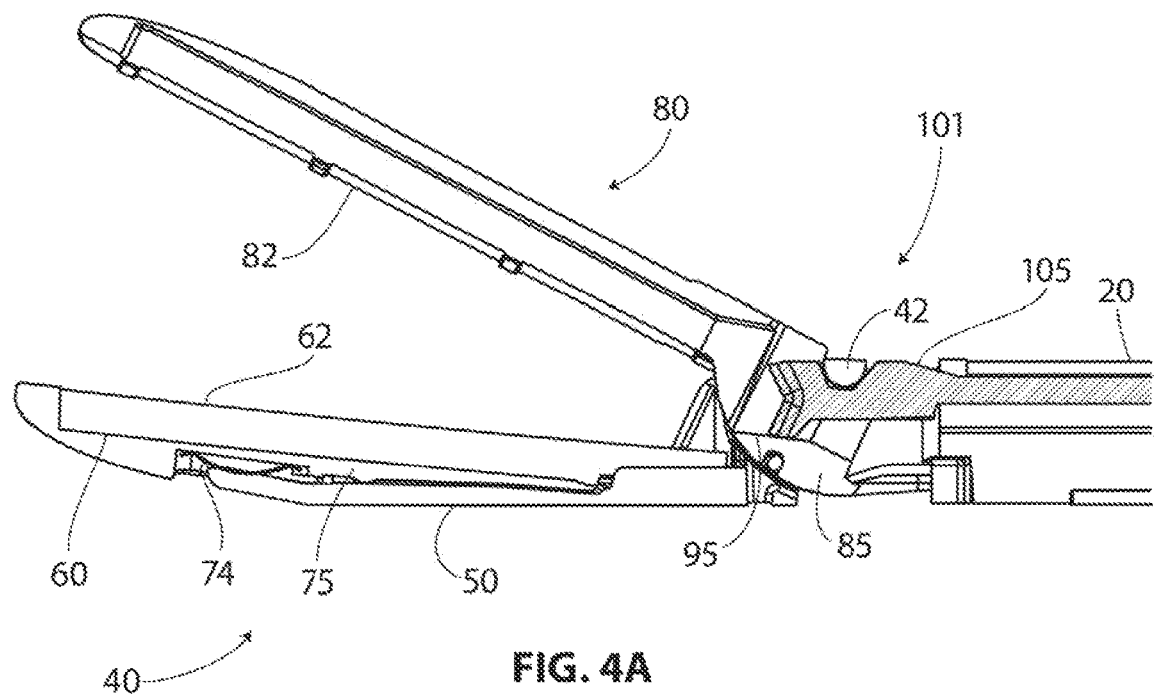
FIG. 4A is a side view through the longitudinal midline of an embodiment of a set of jaws of an electrosurgical device, with the jaws in an open position, and further showing a blade in a proximal and raised holding position.
Figure 4B:
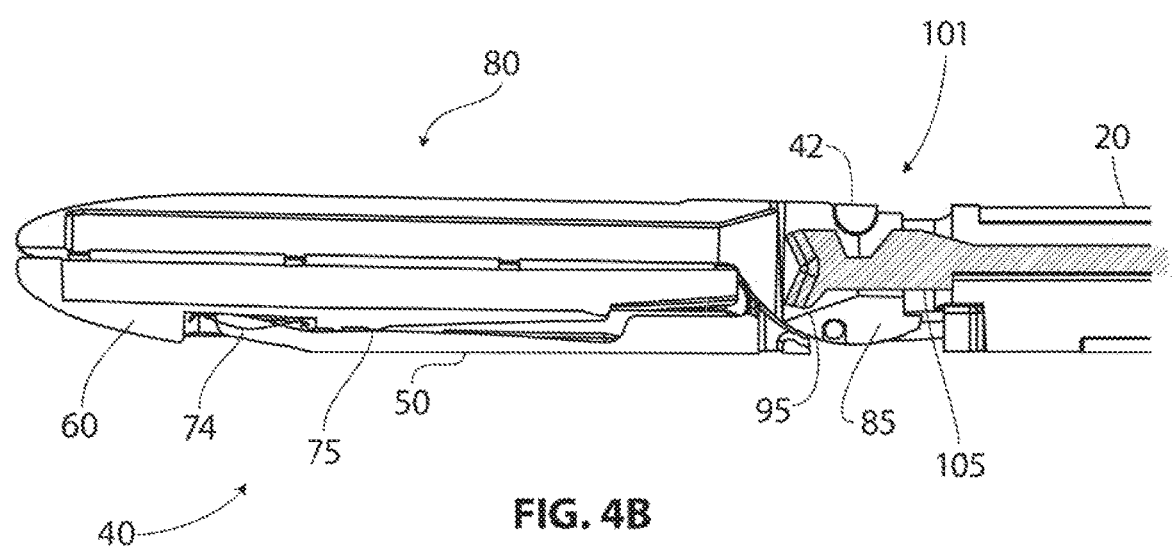
FIG. 4B is a side view through the longitudinal midline of an embodiment of a set of jaws of an electrosurgical device, with the jaws in a closed position, and further showing a blade in a proximal and lowered holding position, ready to be distally advanced.
Figure 4C:
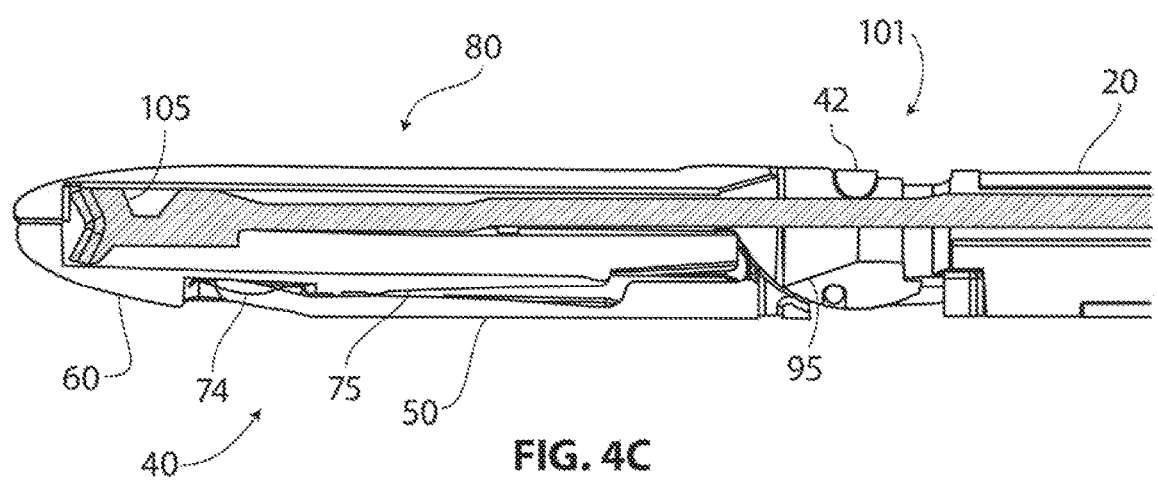
FIG. 4C is a side view through the longitudinal midline of an embodiment of a set of jaws of an electrosurgical device, with the jaws in a closed position, and further showing a blade in a distally advanced position.
Figure 5A:
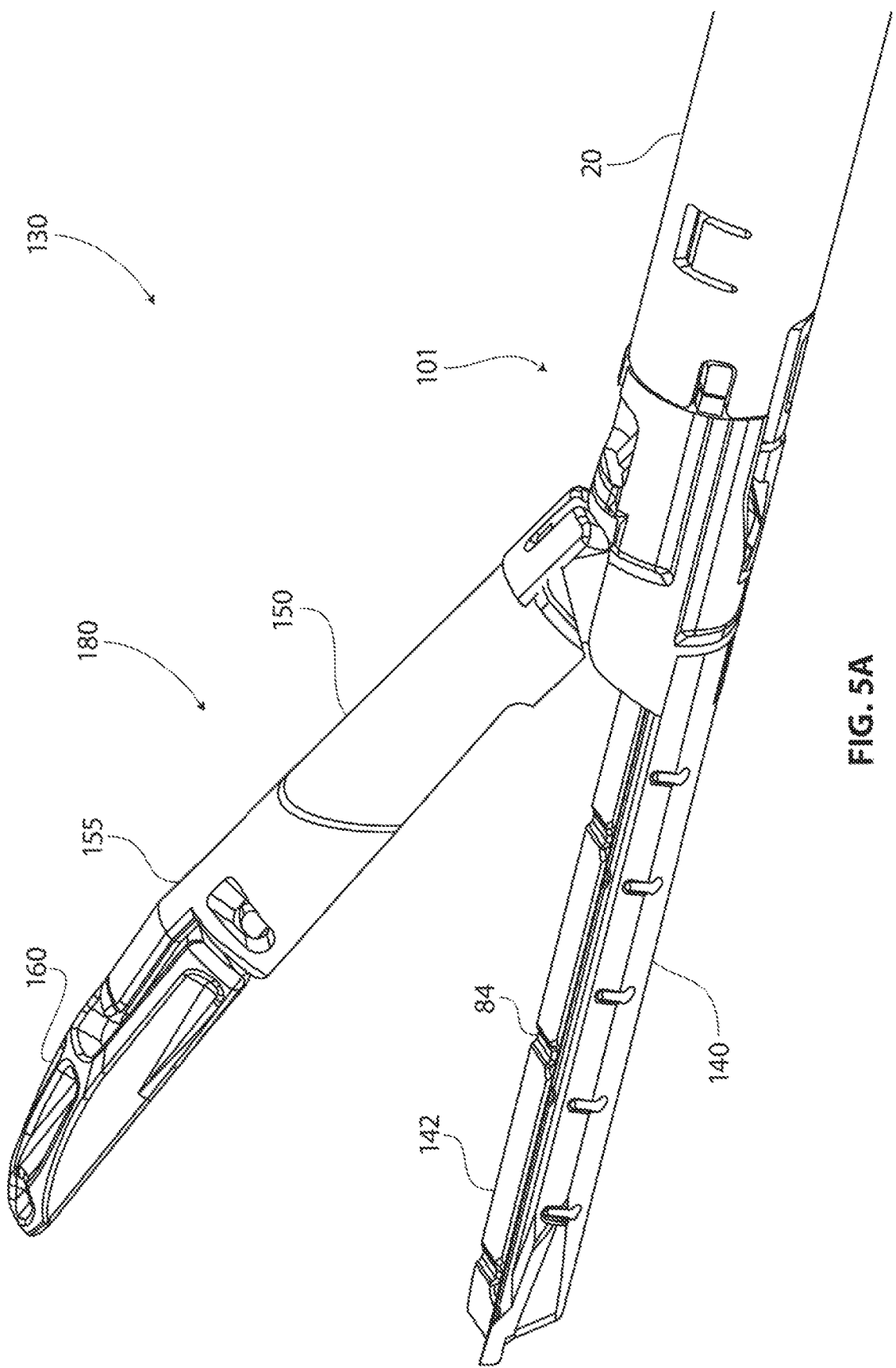
FIG. 5A is a perspective view of an alternative embodiment of an electrosurgical device with the jaws in an open position.
Figure 5B:
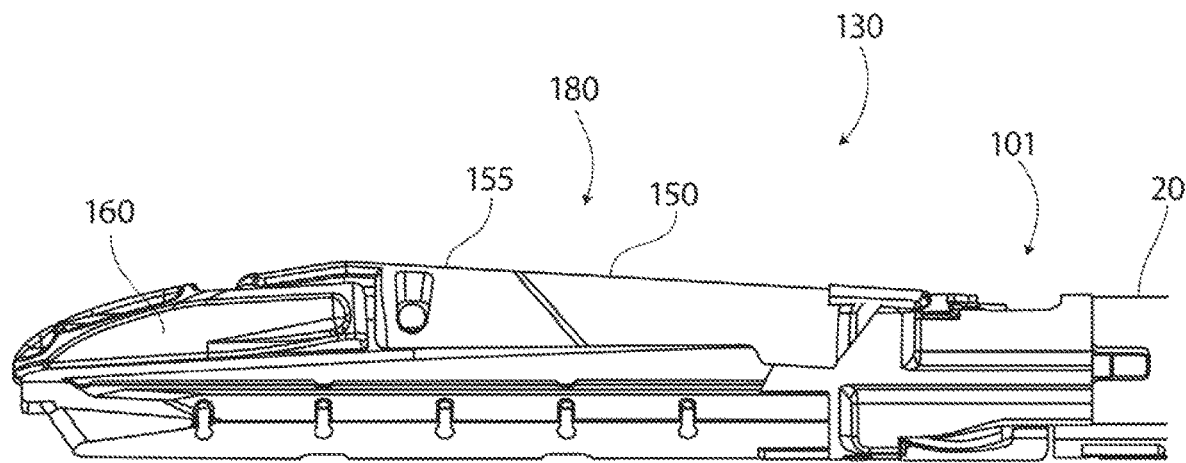
FIG. 5B is a side view of an embodiment of an alternative embodiment of an electrosurgical device with the jaws closed to a position where the distal tips of the jaws are in contact.
Figure 5C:
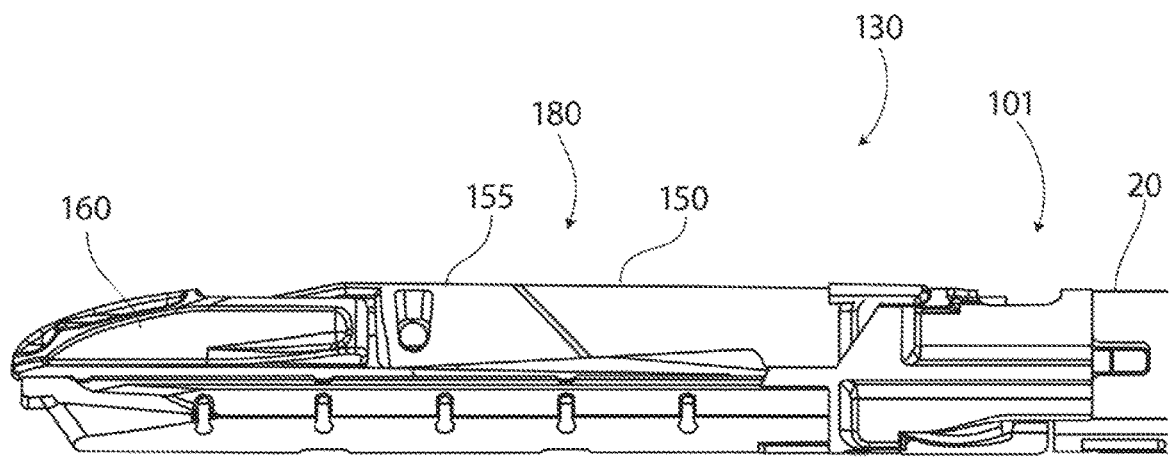
FIG. 5C is a side view of an embodiment of an alternative embodiment of an electrosurgical device with the jaws in a fully closed position.

FIGS. 4A-4D provide side views through the longitudinal midline of an embodiment of set of jaws and various views of an embodiment of a tissue dissecting blade, per the disclosed technology. The focus of these figures relates to aspects of the blade and its proximal holding space that prevents distal movement of the blade when the jaws are in an open position. FIG. 4A shows the device embodiment in an open position with a blade 105 in a proximal and raised holding position. FIG. 4B shows the device embodiment in closed position, with the blade 105 in a proximal and lowered holding position, ready to be distally advanced. FIG. 4C shows the device in closed position, with the blade in a distally advanced position. When blade 105 is in a proximal holding position, its bottom edge 105B rests on shelf 95, a feature of second arcuate track piece 85 of upper jaw 80. (Shelf 95 can also be seen in FIGS. 3A and 3B.) In comparing the views of FIG. 4A (jaws open) and FIG. 4B (jaws closed), it can be seen that when the jaws are open, shelf 95 is rotated to a raised position, and when the jaws are closed, shelf 95 is rotated to a lower position. The raised position of the shelf prevents distal movement of the blade; the lowered position of the shelf allows distal movement of the blade. FIG. 4D is a perspective view of a blade isolated from the shaft and jaws. At its proximal end, blade 105 is connected to a site 109 in the handle that is supported by a mechanical linkage that maintains the blade in a withdrawn or proximally biased position.

The pivoting of upper jaw 80 pivots upward so as to move jaw set into an open position is driven by the rotation of second arcuate track 85 within the enclosure of first arcuate track 45. As seen in FIG. 4A, as arcuate track 85 rotates upward (clockwise, in this view), its shelf 95 also rotates upward, lifting blade 105 upward. As blade 105 is lifted, its upper edge 105A is lifted above the ceiling of distal ward opening of blade track or through passage 106. Blade track 106 is not visible in the side views of FIGS. 4A and 4C, but it can be seen in FIGS. 5A and 5B. When upper jaw 80 is closed with respect to lower jaw 40 (as in FIG. 4B), second arcuate track 85 and its blade shelf 95 is rotated downward, allowing blade 105 to drop into a position such that it has a clear path into blade track 106. This described and depicted relationship among the blade, the shelf of the rotatable second arcuate track (of upper jaw 80), and the blade track, thus creates a mechanism that prevents distal movement of the blade when the jaws are in an open position, allowing distal movement only when the jaws are in a closed position, as seen in FIG. 4C.

FIGS. 5A-5C provide views of an alternative embodiment (Embodiment B) of a laparoscopic electrosurgical device in which a set of jaws 130 includes a first jaw 140 that is unitary and fixed with respect to the shaft and the second jaw 180 is a two-piece jaw that is pivotable with respect to the shaft. More particularly, the two-piece (second) jaw of this embodiment has a proximal piece 150 that is pivotable with respect to the shaft, a distal jaw piece 160 that is pivotable with respect to the proximal piece, and a pivotable assembly 155 connecting the proximal jaw piece and the distal jaw piece. FIG. 5A provides a perspective view of this device embodiment with the jaws in an open position. FIG. 5B provides a side view of the embodiment with the jaws closed to a point where the distal tips of the jaws are in contact. FIG. 5C provides a side view of the embodiment with the jaws in a fully closed position. FIG. 5A shows the jaws without a polymer coating; this affords a view of troughs 84 within the electrode surface 142. Similar troughs are present in the upper jaw of embodiment A.

Other than the variation in the configuration of the jaws as just described, other aspects of embodiments A and B are substantially the same. In particular, the dynamics of the closing of the jaws of Embodiment B are the substantially the same as those of Embodiment A, which are described in detail below, in the context of FIGS. 7A-7E.

Figure 6:
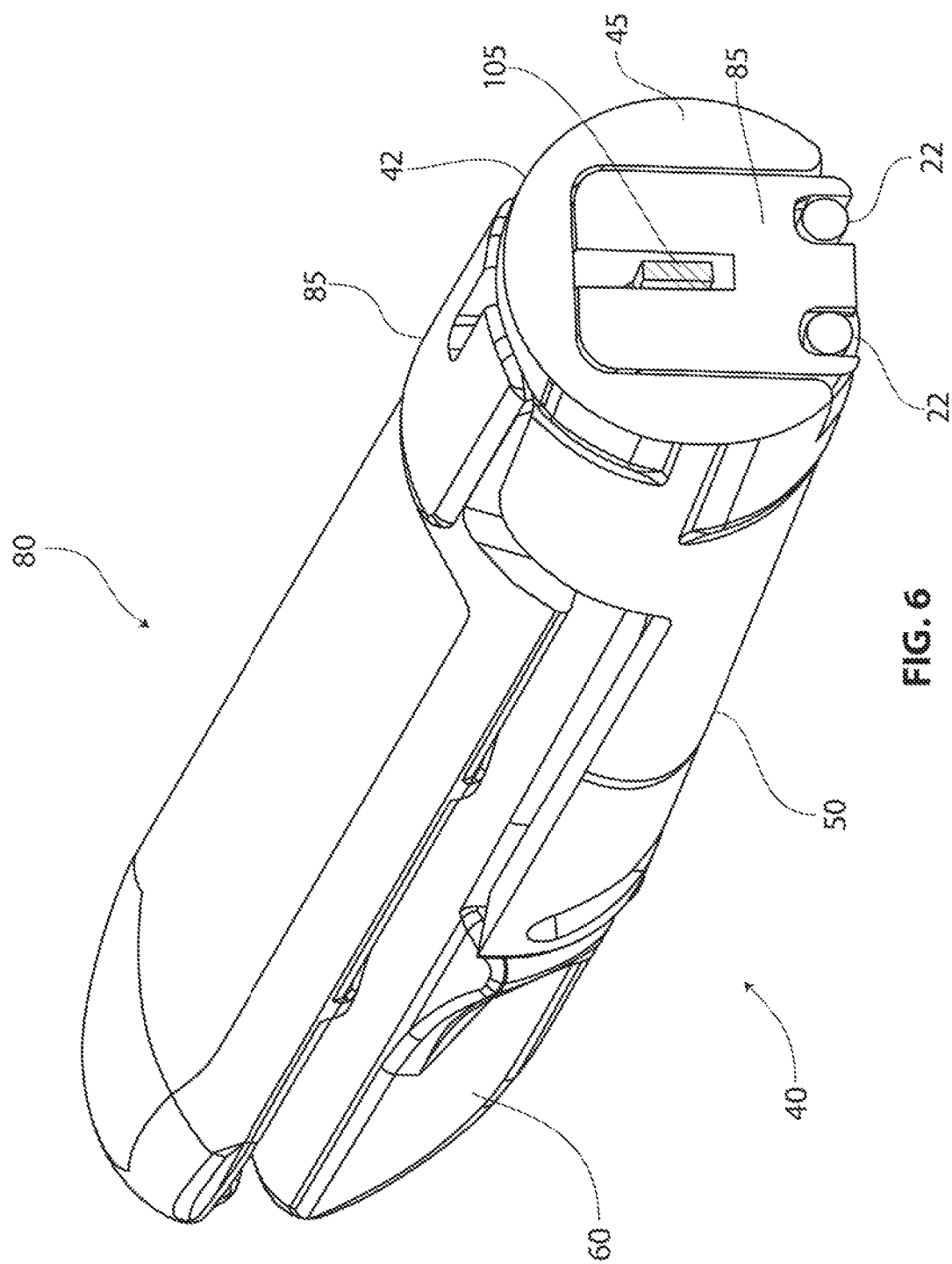
FIG. 6 is a distal looking perspective view of an embodiment of a set of jaws of an electrosurgical device with the jaws in a closed position, a cross sectional exposure showing a passage through which a blade may be distally advanced.

FIG. 6 provide distal looking perspective views of a set of jaws of an embodiment of laparoscopic electrosurgical device in closed position, more particularly, a cross sectional exposure shows a blade passage way or track 106 through which a blade may be distally advanced. The cross sectional slice on the right side of FIG. 6 reveals a section through first arcuate track 45 (of the proximal portion 50 of lower jaw 40) that substantially encloses second arcuate track 85 (of upper jaw 80). A proximal cross sectional slice through of blade 105 can be seen within slot 88 of second arcuate track 85. Slot 88 is contiguous with blade track 106 of the jaws, as seen best in FIG. 12C.

FIG. 6 also provides a view that allows a calculation of the proportion of the total cross sectional area of a critical portion of the device that provides forward supporting structure to the jaws. This portion of the device is a relevant site to consider for its structural content in that it includes the pinless rotational mechanism whereby the jaws pivot with respect to each other. In an otherwise more conventional structure, this area might include through pins or other structures that do not convey structural support to the jaws. In this area, thus, embodiments of a pinless rotation mechanism provide structural material content that might otherwise be missing. If a diameter of 0.218 inch is considered, which is consistent with the contiguous circular aspect of the base of the jaws is drawn, the cross sectional area included therein is about 0.0373 square inches. Through this section the cross sectional area of the upper jaw is about 0.0151 square inches, and that of the lower jaw is about 0.0155 square inches. The summed area of the upper and lower jaws is about 0.0306 square inches, or about 82% of the total cross sectional area.

FIGS. 7A-7E provide side views of a set of jaws of an embodiment of a laparoscopic electrosurgical device in an open position, and in several states of partial or initial closure and full closure. These figures focus on the pivotable relationship between distal pivotable piece or portion 60 and fixed proximal or base piece 50 of lower jaw 40, as enabled by pivotable rotation assembly or mechanism 75. The pivotable relationship between pivotable portion 60 and base portion 50 plays out in various ways that lower jaw 40 and upper jaw 80 approach each other as they close, particularly as they close around a portion of target tissue to be treated electrosurgically.

Figure 7A:
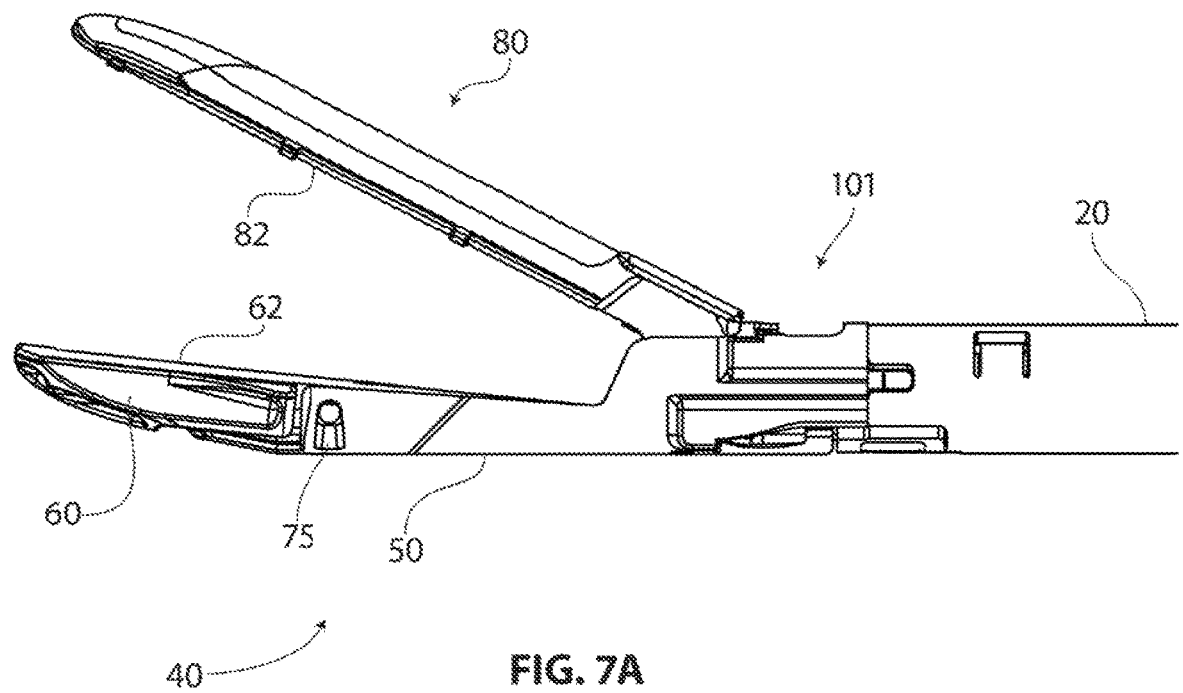
FIG. 7A is a side view of an embodiment of set of jaws of an electrosurgical device, with the jaws in an open position.
Figure 11A:
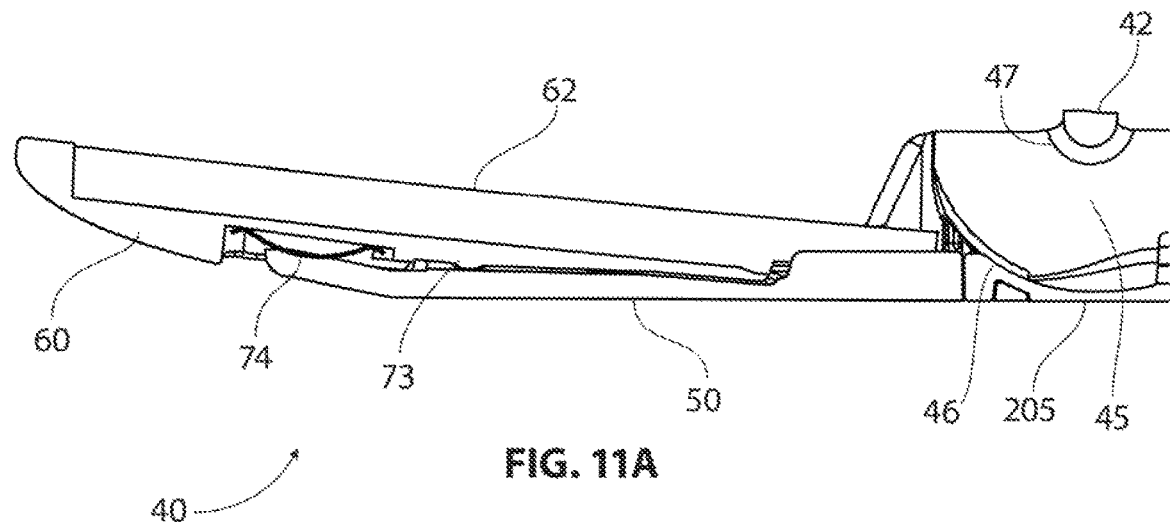
FIG. 11A is a side view of an embodiment of a lower jaw of an electrosurgical device similar to the view shown in FIG. 10A, showing a leaf spring attached an upper aspect of the proximal jaw piece, the spring pushing against the distal pivotable jaw piece so as to maintain the distal pivotable piece in its default biased position, the distal end of the distal pivotable jaw piece pivoted to its upper end point.

FIG. 7A shows the jaw embodiments in an open position. Pivotable jaw portion 60 of first jaw or lower jaw 40 is pivotable within its longitudinal axis at pivotable connection 75 through an arc with total rotational range of about 6 degrees. In various embodiments, the rotational range may be between about 2 degrees and about 8 degrees or more. In the open position as shown in FIG. 7A, pivotable jaw piece 60 is pivoted to its maximal degree of clockwise rotation, with the distal end of the pivotable jaw piece in a raised position. (The terms clockwise and counter clockwise are used in relative to the side view depicted, with the distal end of the jaw on the left hand side of the image.) This clockwise position is a default or biased position as shown in FIG. 11A, which show the lower jaw 40 isolated from upper jaw 80. This default position may be maintained by a push from a spring or biasing mechanism disposed at the proximal end of an actuator wire (not shown).

A clockwise rotation or pivoting of pivotable jaw piece 60 (of lower jaw 40) results in its distal end or tip 66 assuming a relatively high profile and its proximal aspect assuming a relatively low profile with respect to proximal jaw piece 50. The differences in profile are relatively subtle, but are apparent when the proximal aspect of the upper profile of the surface of electrode 62 is viewed in relationship to the upper surface of the proximal aspect of the proximal jaw piece 50.

In FIG. 7A, for example, there is a relatively small linear profile of electrode 62 visible over the base provided by proximal jaw piece 50. The height of this profile, indicative of the relative degree of pivoting of the pivotable jaw piece 60, will be pointed out in the descriptions associated with FIGS. 7B-7E, below. The relationship between the pivoting of the pivotable jaw piece 60 with respect to base jaw piece 50 is also apparent in FIGS. 10A and 10B.

Figure 7B:
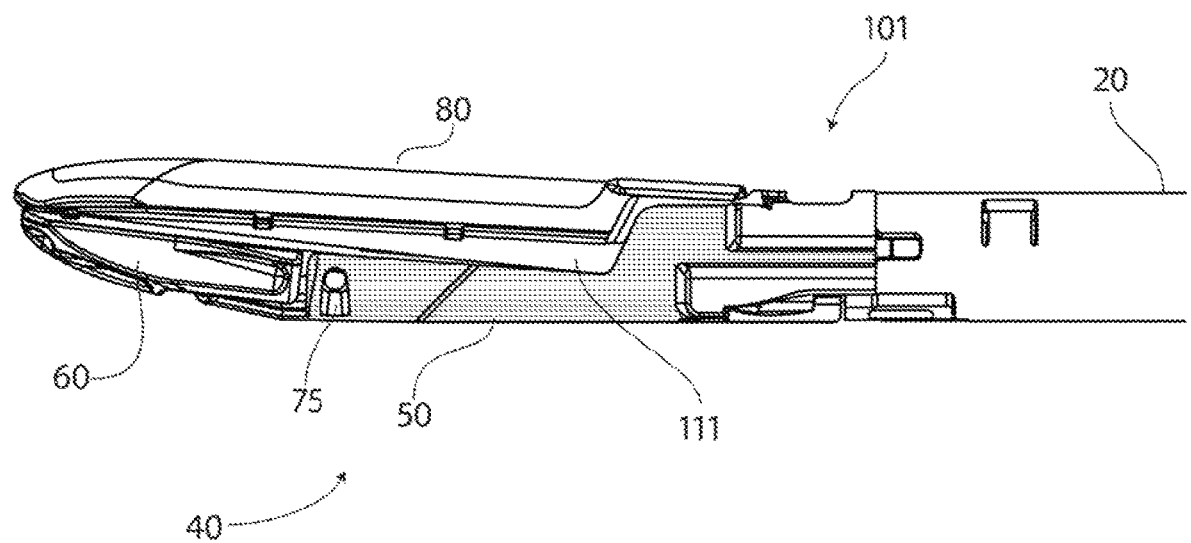
FIG. 7B is a side view of an embodiment of set of jaws of an electrosurgical device, with the jaws at an initial point of closure, when the distal tips of the jaws have first made contact each other and a gap remains between the jaws at their proximal end.

FIG. 7B shows an embodiment of a set of jaws at a point when they are moving toward a closed position, when the distal tips of the jaws (distal tip 96 of upper jaw 80 and distal tip 66 of lower jaw piece 60) first contact each other. Upon first contact of the tips of the jaws, a gap remains in the region between the jaws 111 at their proximal end. As in FIG. 7A, the pivotable piece 60 is in its default biased position, pivoted to its maximal degree of clockwise rotation. In this position, upon first contact of the tips, no pressure has yet been applied to the tips of the jaws. As in FIG. 7A, there is a relatively small linear profile of electrode 62 visible over the base provided by proximal jaw piece 50.

Figure 7C:
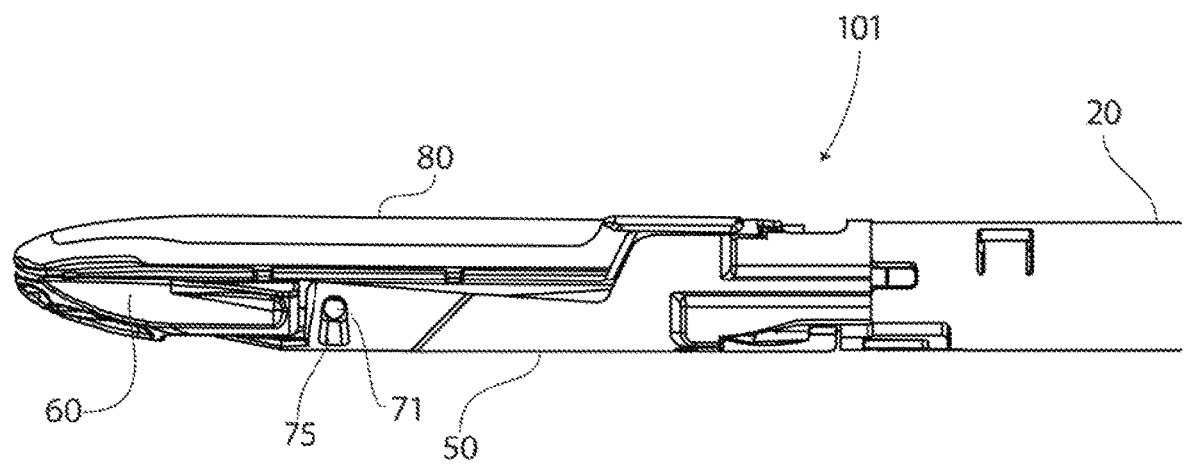
FIG. 7C is a side view of an embodiment of set of jaws set of an electrosurgical device, with the jaws in a fully closed position, wherein the jaws are in full contact with each other from distal tip to proximal end.

FIG. 7C shows the jaw embodiments in a fully closed position, with the jaws, from distal tip to proximal end, in full contact with each other. This relative positioning of the jaws may be understood as one that would occur when the jaws are being closed without intervening tissue between them, or when intervening tissue is very thin. Thus, this relative configuration is similar to that arrived at when the jaws are closed around a thin piece of tissue, as seen in FIG. 7E (described below), but without the intervening space occupied by tissue. This position is arrived at by a counter clockwise pivoting of the pivotable piece 60 of lower jaw 40 around pivotable connection 75 such that the distal tip of the pivotable piece has moved downward, and the proximal end of the pivotable piece has moved upward. Consistent with this raised aspect of the proximal piece of pivotable jaw piece 60, and in contrast to the view seen in FIGS. 7A and 7B, FIG. 7C shows there to be a relatively high linear profile of electrode 62 visible over the base provided by proximal jaw piece 50. Details of pivotable connection 75, in its components that are associated with both the pivotable jaw piece 60 and the distal base jaw piece 50 may be seen in FIGS. 9A-9D.

Figure 7D:
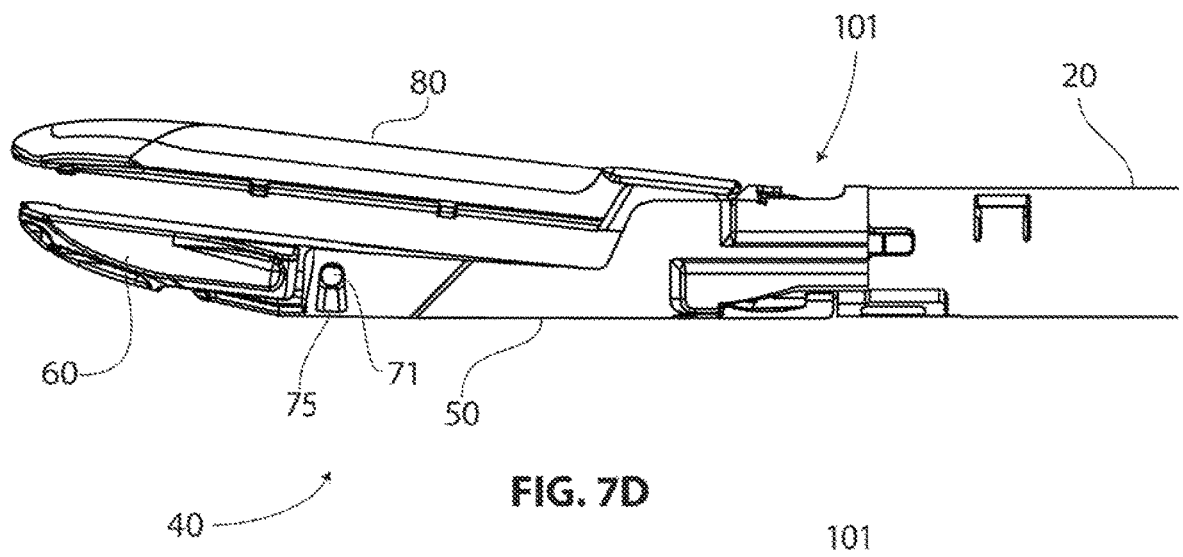
FIG. 7D is a side view of a set of jaws of an embodiment of an electrosurgical device in a partially closed position, with the jaws as they would be positioned when closing around a portion of relatively thick target tissue, the jaws in a parallel alignment, spaced relatively widely apart by the presence of thick tissue therebetween.
Figure 7E:
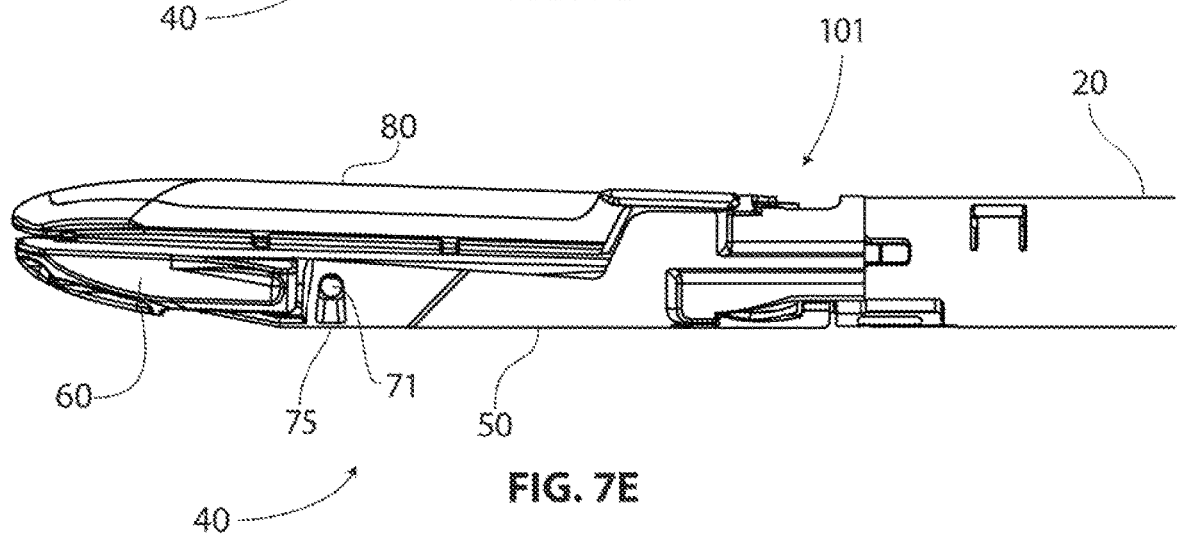
FIG. 7E is a side view of a set of jaws of an embodiment of an electrosurgical device in a partially closed position, with the jaws as they would be when closing around a portion of relatively thin target tissue, the jaws in a parallel alignment, spaced apart by a narrow gap, reflecting the presence of thin tissue therebetween.

FIG. 7D shows the jaw embodiments in a partially closed position, with the jaws as they would be when closing around a portion of relatively thick portion of target tissue (not shown), but of a thickness that does not exceed the effective capacity of the jaws. The intra-jaw pivotability, as represented by first jaw 40, provides a capability for a set of jaws to align in a parallel or substantially parallel configuration as they close around a portion of tissue, a capability that provides an advantage over a set of conventional jaws without such intra-jaw pivotability. The configuration of jaws as depicted in FIG. 7D is one in which thickness of target tissue would likely exceed the therapeutically acceptable limit of thickness for a conventional set of jaws, but which is well within the therapeutically effective capacity.

A non-parallel closure of jaws, as is typical of conventional jaws that do not have intra-jaw pivotability or another compensatory mechanism, can have therapeutically unsatisfactory consequences, such as uneven distribution of pressure on tissue along the line of jaw contact, as well as uneven distribution of radiofrequency energy when delivered by electrodes. Embodiments of a set of jaws as provided herein, however, can of course still be confronted with a portion of target of tissue that exceeds their capacity for parallel closure of tissue engaging surfaces of jaws. However, as noted, the thickness of tissue that would account for the configuration of the jaws as seen in FIG. 7D is one that demonstrates the therapeutic advantage of the intra jaw pivotability of lower jaw 40.

This relative positioning of the jaw embodiments as seen in FIG. 7D comes about for at least two reasons. First, the jaws are not completely closed at the level of the rotational assembly connecting the proximal aspects of the jaws. Second, as in FIG. 7C, this position has been arrived at by a counter clockwise pivoting of the pivotable piece 60 of lower jaw 40 around pivotable connection 75 at least partially through its range of angular rotation. From the default position of pivotable piece 60, this clockwise rotation has moved the distal tip of jaw piece 60 downward and the proximal end of jaw piece 60 upward. Accordingly, and by virtue of this parallel jaw configuration, pressure being applied to the tissue from the jaws is distributed with substantial evenness across the length of contact between the jaws and the tissue, and radiofrequency energy, when delivered, is also distributed with substantial longitudinal evenness or uniformity.

FIG. 7E shows the jaw embodiments in a partially closed position, with the jaws, as they would be when closing around a portion of relatively thin target tissue, the jaws in a parallel alignment, spaced apart by a narrow gap, reflecting the presence of thin tissue therebetween. This relative positioning of the jaws comes about at least for two reasons, as similarly described above in the context of FIG. 7D. First, the jaws are nearly but not completely closed at the level of the rotational assembly connecting the proximal aspects of the jaws. Second, this position has been arrived at by a counter clockwise pivoting of the pivotable piece 60 of lower jaw 40 around pivotable connection 75 through, or nearly through its range of angular rotation. This clockwise rotation has moved the distal tip of jaw piece 60 slightly downward and the proximal end of jaw piece 60 slightly upward. As seen in FIGS. 7A and 7B, there is a relatively small linear profile of electrode 62 visible over the base provided by proximal jaw piece 50.

Figure 8:
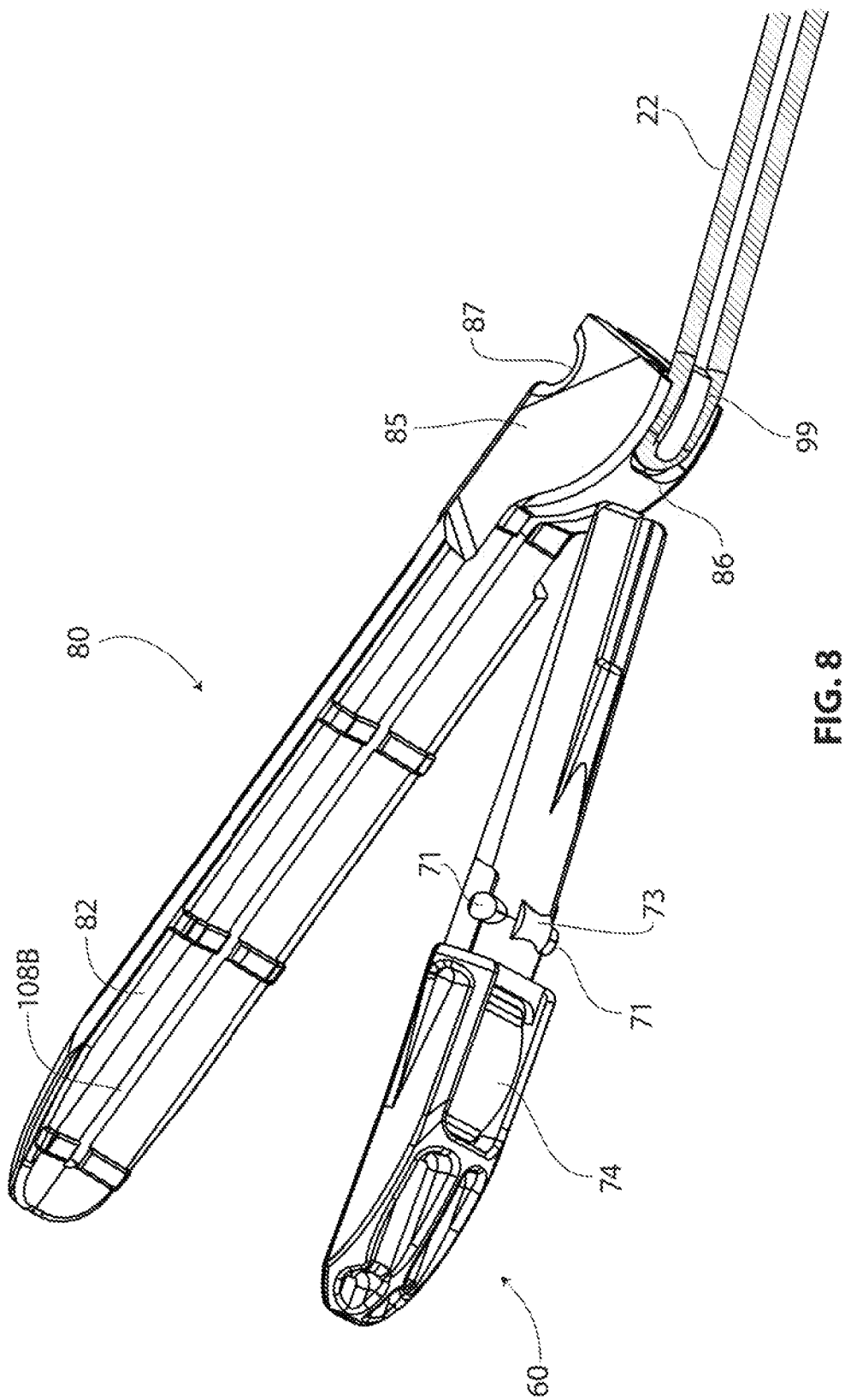
FIG. 8 is a perspective and upward looking view of a set of jaws of an embodiment of an electrosurgical device with the jaws in an open position, the view showing, more specifically, an isolated upper jaw, an isolated distal pivotable piece of a lower jaw, and an actuator wire looped around an attachment point at the proximal end of the upper jaw.

FIG. 8 is a perspective and upward looking view of a set of jaws of an embodiment of a laparoscopic electrosurgical device in an open position. More specifically, it shows an isolated upper jaw 80 and an isolated distal pivotable jaw piece 60 of a lower jaw, and an actuator wire or cable 22 looped around an attachment point 99 at the proximal end of the upper jaw. An advantage provided by this arrangement relates to ease of manufacture and assembly of this aspect of the device in that a fixed soldering point is not needed. A further structural advantage is that tension within the actuator wire is distributed through a portion of the length of the loop, rather than being focused at an attachment point. It can be seen that a distal push by actuator wire 22 would cause an upward pivoting of upper jaw 80 toward an open jaw position, and a proximal pull would cause a downward pivoting of upper jaw 80 toward a closed jaw position. At its proximal end, actuator wire 22 is connected to jaw actuator grip 15, shown in FIG. 1.

FIGS. 9A-9D provide various views of a lower jaw 40 of an embodiment of a laparoscopic electrosurgical device that includes proximal or base jaw piece 50 that is fixed with respect to the shaft and distal pivotable jaw piece 60 that is pivotably connected to the base piece. The focus of FIGS. 9A-9D relates to embodiments of a pivotable connection or assembly 75 that connects jaw pieces 50 and 60. The pivotable proximal jaw piece and the distal jaw piece are pivotably connected at pivotable joint located at a substantially central site on the pivotable piece and at a distal aspect of the proximal jaw piece.

Figure 9A:
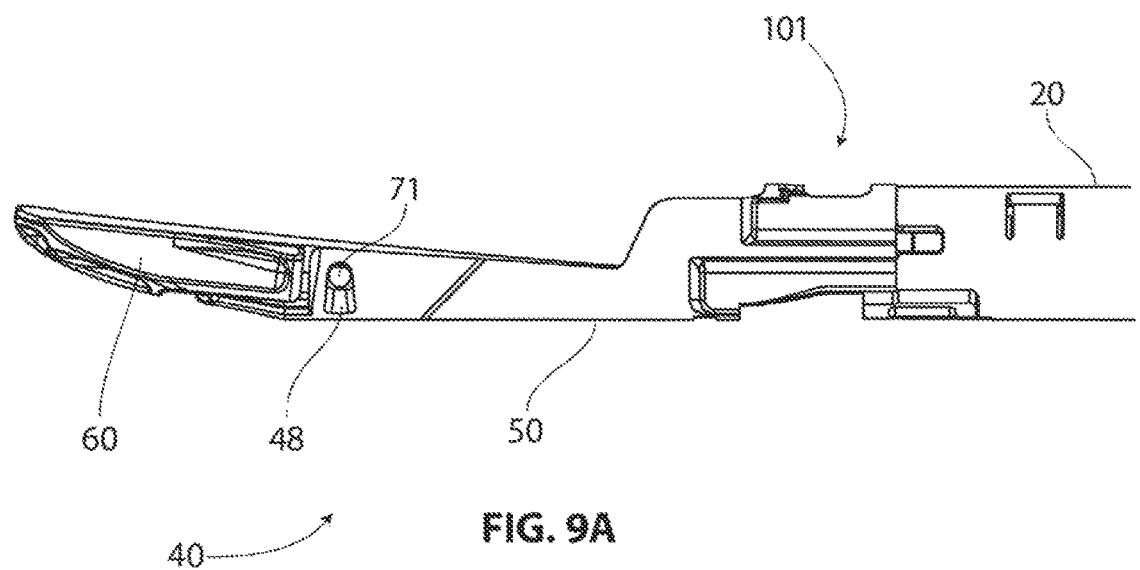
FIG. 9A is a side view of an embodiment of an isolated lower jaw of an electrosurgical device, the lower jaw including a proximal jaw piece that is fixed with respect to the shaft and a distal pivotable jaw piece mounted at a substantially central point of the distal piece on the proximal jaw piece.

FIG. 9A is a side view of an isolated lower jaw 40 of a laparoscopic electrosurgical device, the lower jaw including a proximal jaw piece 50, fixed with respect to the shaft, and distal pivotable jaw piece 60 mounted at a substantially central point on a distal aspect of the proximal jaw piece. It can be seen that pivotable assembly 75 includes a boss 71 of pivotable jaw piece 60 rotatably disposed in a recess 48 of base jaw piece 50. This is a bilateral arrangement, bosses 71 projecting outward on both sides of pivotable jaw piece 60, and mating recesses 48 on both sides of base jaw piece 50. This arrangement thus represents a pivotable mechanism that does not include a through pin. This arrangement further provides advantage in ease of assembly, in that the component parts can be snap fitted together.

Figure 9B:
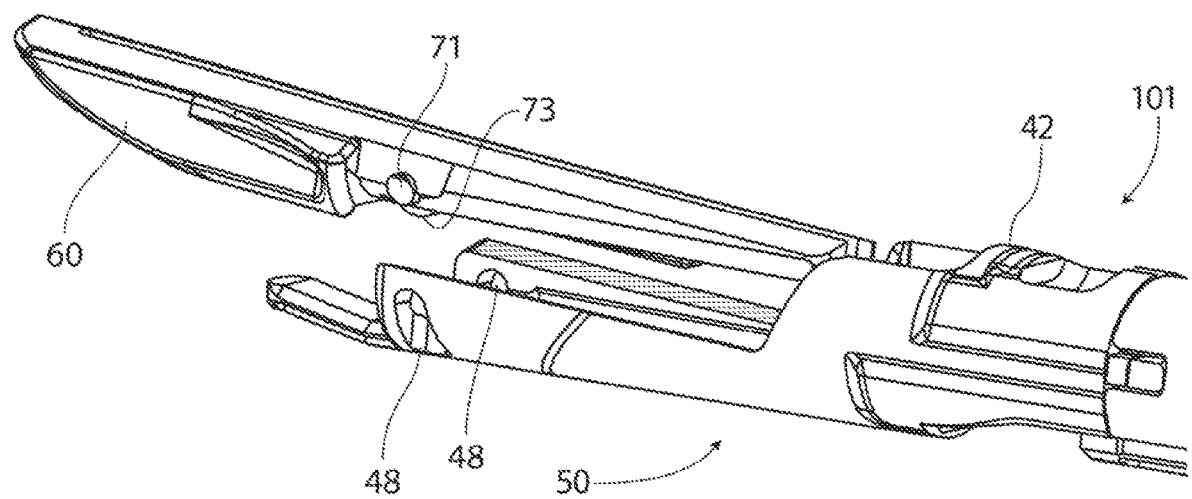
FIG. 9B is a perspective and exploded view of an embodiment of a isolated lower jaw of a laparoscopic electrosurgical device, the lower jaw having a proximal jaw piece fixed to a shaft and distal pivotable jaw piece, the proximal and distal jaw pieces shown in an exploded relationship.
Figure 9C:
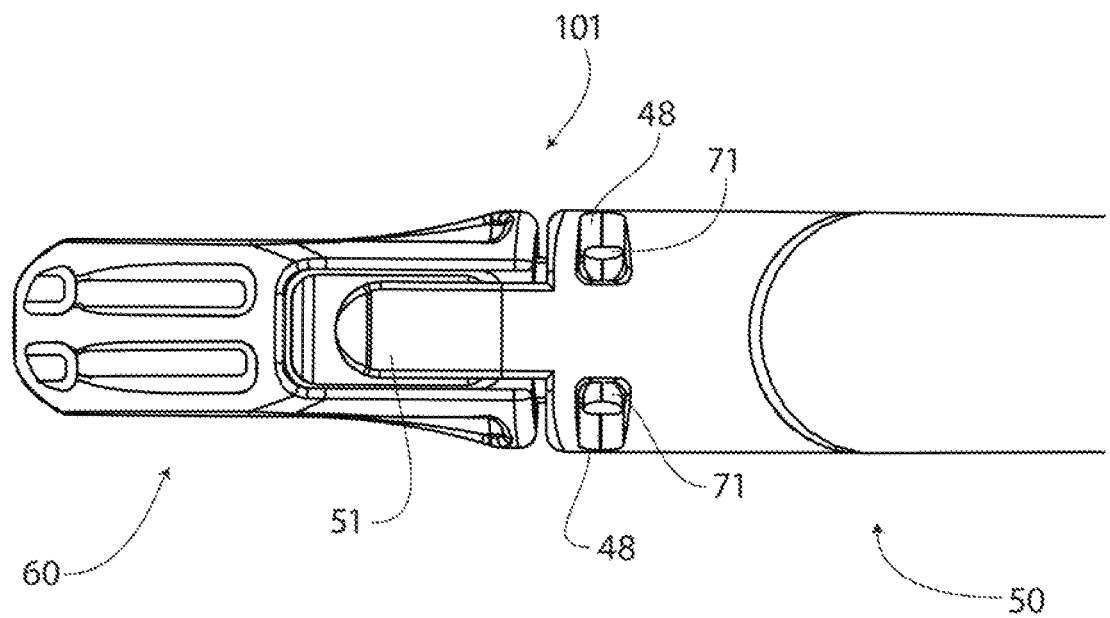
FIG. 9C is a bottom view of a lower jaw of an embodiment of an electrosurgical device, showing a connection between a proximal fixed jaw piece and distal pivotable jaw piece.

FIG. 9B is a perspective view of an embodiment of an isolated lower jaw 40 of a laparoscopic electrosurgical device that shows a lower jaw 40 having a proximal jaw piece 50 and distal pivotable jaw piece 60 in an exploded relationship. Distal piece 60 is shown moved up and moved distally with respect to its assembled position within proximal piece 50. A boss 71 is visible on one side of pivotable jaw piece 60, and both of receptacles or recesses 48 of lower base jaw piece 50 are visible. The proximal aspect of base jaw piece 50 is sufficiently flexible that it can expand to accommodate entry of pivotable jaw piece 60. After engagement of both bosses 71 into their respective receptacles 48, the expanded base piece snaps back to its native configuration, thus securing the pivotable jaw piece in place. Also visible in this view is pivot ridge 30, centrally disposed beneath bosses 71. When assembled, pivot ridge is in contact with an upper surface of base jaw piece 50, and provides the elevation that allows pivoting to occur. FIG. 9C provides a bottom view of a lower jaw 40 of a laparoscopic electrosurgical device, showing a view of the connection between a tongue portion 51 of proximal jaw piece 50 and distal pivotable jaw piece 60 assembled together. Bosses 71 of pivotable jaw piece 60 are visible within recesses 48 of lower base jaw piece 50.

Figure 9D:
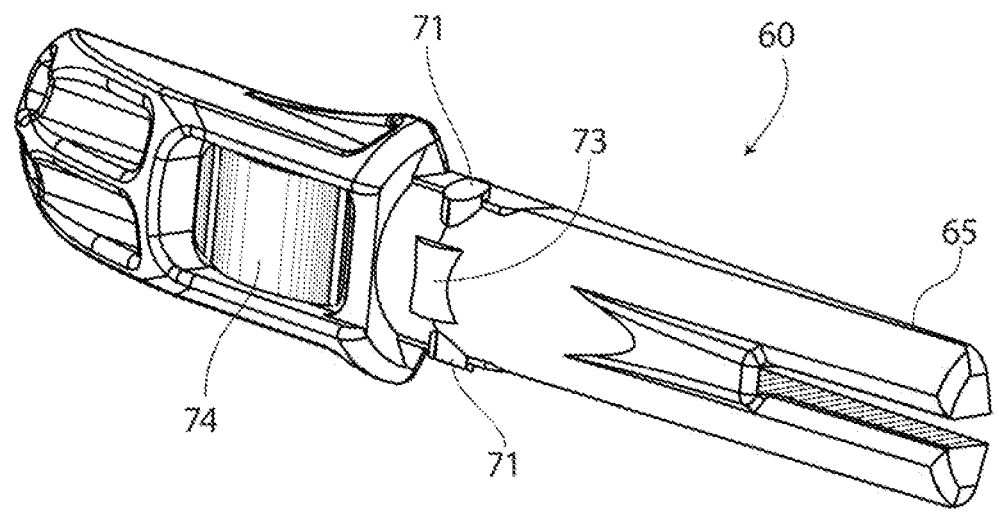
FIG. 9D is an upward looking perspective view of an embodiment of a distal piece of a lower jaw of an electrosurgical device.

FIG. 9D is an upward looking perspective view of an isolated distal pivotable piece 60 of a lower jaw 40 of a laparoscopic electrosurgical device. Bosses 71 are visible; as is pivot ridge 73. Also visible is a biasing member such as leaf spring 74 that is positioned in a recess of the lower aspect of pivotable jaw piece 60 of lower jaw piece 50. Embodiments of a biasing member disposed in this position serve to maintain a bias or default position of pivotable piece 60 such that its distal tip is pushed away from the distal end of companion fixed jaw piece 50 of lower jaw 40, and toward the distal tip of upper jaw 80, as seen, for example, in FIG. 7B. The proximal end 65 of pivotable piece 60 includes a centrally disposed longitudinal cleft, which is a part of and contiguous with blade track 108A in the lower law, as seen from a top view perspective in FIGS. 2A and 12C.

Figure 10A:
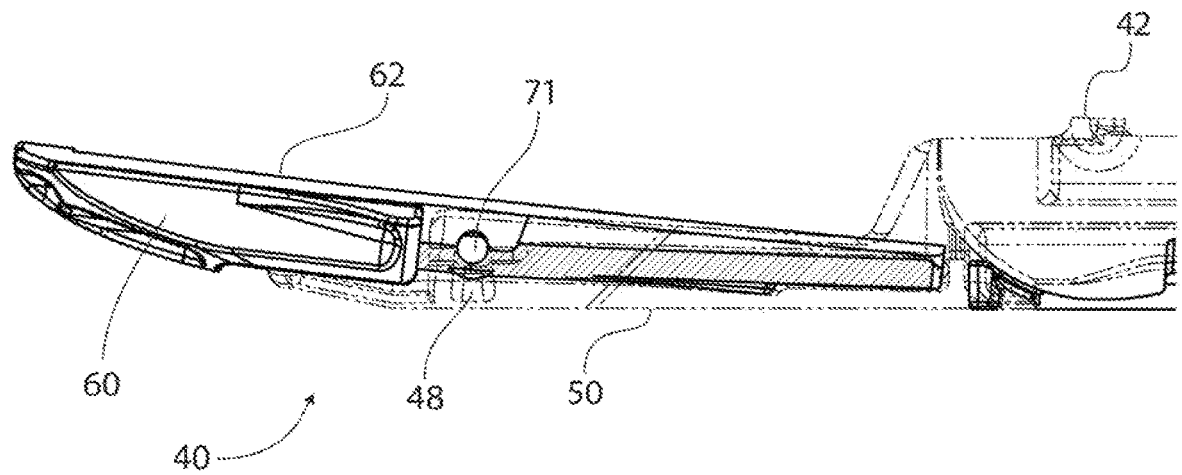
FIG. 10A is a semitransparent side view of an embodiment of a lower jaw of an electrosurgical device, showing a proximal jaw piece and pivotably connected distal pivotable jaw piece, the distal pivotable piece in its default biased position, the distal end of the distal pivotable jaw piece pivoted to its upper end point, toward an upper jaw (not shown).
Figure 10B:
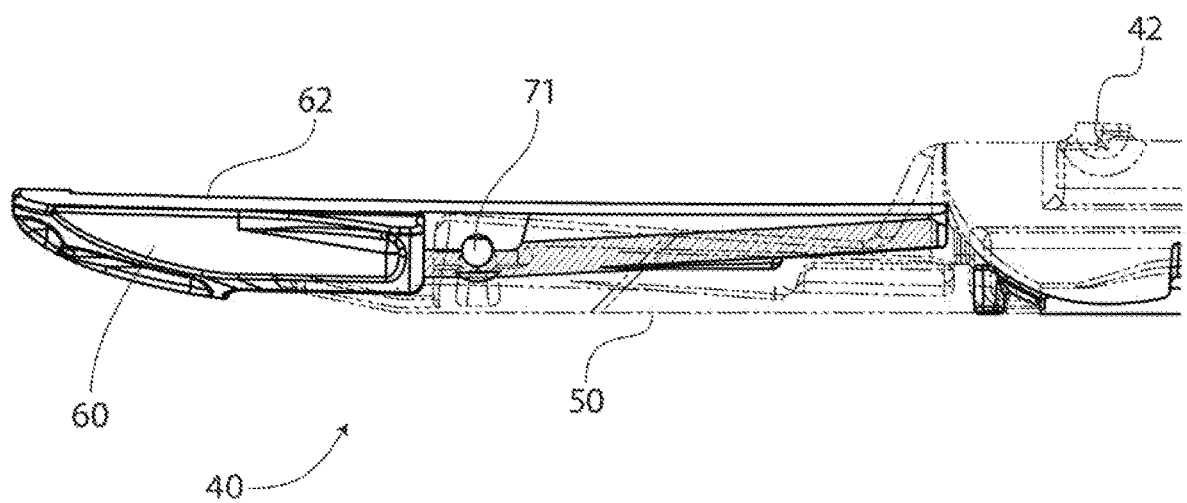
FIG. 10B is a semitransparent side view of an embodiment of a lower jaw of an electrosurgical device, showing a pivotably connected proximal jaw piece and distal pivotable jaw piece, the distal end of the distal pivotable jaw piece pivoted toward its lower end point, the proximal end of the distal pivotable jaw piece pivoted toward its upper end point, such a position putting the lower jaw in a substantially parallel relationship with the upper jaw (not shown).

FIGS. 10A and 10B provide semitransparent side views of a lower jaw 40 of an embodiment of a laparoscopic electrosurgical device, showing a proximal base jaw piece 50 and pivotably connected to distal pivotable jaw piece 60. FIG. 10A shows the distal pivotable jaw piece 60 in its default biased position, the distal end of the distal pivotable jaw piece being pivoted to its upper end point, toward the upper jaw (not shown). This default position is maintained as a bias by a spring, as seen best in FIGS. 11A and 11B. This is the pivoted position of distal jaw piece when the jaws are open, and which is held as the jaws are closed until a point when the distal tips of the jaws first make mutual contact, such contact representing a default tip-first closure feature of the jaws.

In contrast, FIG. 10B shows the distal end of the distal pivotable jaw piece 60 pivoted toward its lower end point, the proximal end of the distal pivotable jaw piece being pivoted toward its upper end point, such a position would putting the lower jaw in a generally parallel relationship with the upper jaw (not shown). This is the pivoted position of distal jaw piece when the jaws when the jaws are closed, or generally the position when jaws are closed around tissue, particularly when they closed around thing tissue. A boss 71 and pivot ridge 73 on the pivotal jaw piece 60 can be seen. Boss 71 is positioned within receptacle or recess 48 of base jaw piece 50. The boss and receptacle arrangement and the pivot ridge together form a pivotable connection or assembly 75.

As summarized above, embodiments of the pivotable connection or assembly 75 provide a pivotable range of about 2 degrees to about 8 degrees; particular embodiments are configured to pivot within a range of about 6 degrees. The relationship between the pivoting of distal jaw piece 60 and the dynamics associated with opening and closing the jaws, with and without tissue being grasped between them, is described above in the context of FIGS. 7A-7E. Particularly clear in FIGS. 10A and 10B is the difference in elevation of the proximal aspect of pivotable jaw 60 and its electrode bearing and tissue engaging surface 62 above the upper edge of the proximal portion of base jaw piece 50.

Figure 11B:
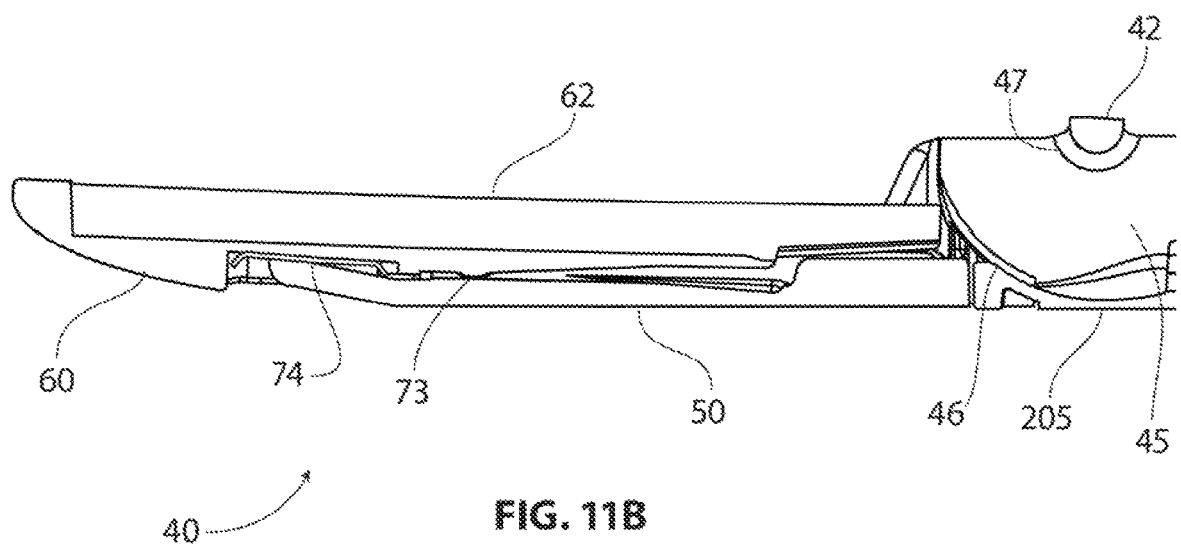
FIG. 11B is a side view of an embodiment of a lower jaw of an electrosurgical device similar to the view shown in FIG. 10B, showing a leaf spring attached an upper aspect of the proximal jaw piece, the spring collapsed by the pressure being exerted on the distal end of the distal pivotable piece of the jaw, as would occur during closure of the jaw.

FIGS. 11A and 11B provide side views of a lower jaw of a laparoscopic electrosurgical device that are similar to those shown in FIGS. 10A and 10B, but which have a greater degree of transparency through the distal and pivotable piece 60 of lower jaw 40. These figures focus on a biasing member 74 in the form of a leaf spring attached to an upper aspect of the distal piece of proximal and fixed jaw piece 50. Embodiments of the technology include other arrangements that would serve the same biasing function. For example, the biasing member may include other types of springs, and it could be attached to the pivotable piece of the jaw rather than the fixed piece. In the depicted example, FIG. 11A shows leaf spring 74 attached an upper aspect of the proximal jaw piece; the spring is in an expanded configuration, pushing against the distal pivotable jaw piece so as to maintain the distal pivotable piece in its default biased position whereby the distal end of the distal pivotable jaw piece pivoted to its upper end point. In contrast, FIG. 11B the spring collapsed or compressed configuration, the result of pressure being exerted on the distal end of the distal pivotable piece of the jaw, as would occur during closure of the jaw.

FIGS. 12A-12C provide various proximal looking views of the distal tips of the jaws of an embodiment of laparoscopic electrosurgical device. These views focus on mutually complementary longitudinal aligning features that prevent lateral slippage or misalignment when the jaws close, particularly when they close around a portion of target tissue. Complementary V-shaped surfaces are used in the depicted examples of longitudinal features that encourage the self-alignment of jaws, but those familiar with the art will recognize that other complementary surfaces will serve the same purpose, and as functional equivalents, are included as embodiments of the disclosed technology.

FIG. 12A is a proximal-looking perspective view of the distal tips of a closed set of jaws, while FIG. 12B is a facing view. Upper jaw 80 shows a V-shaped recession on distal tip 96; distal piece 60 of lower jaw 40 shows a V-shaped projection on its distal tip 66. The mutually complementary V-shaped profiles are represent a profile that extends substantially through the length of the respective electrode surfaces, i.e., electrode surface 82 of upper jaw 80 and electrode surface 62 of pivotable piece 60 of lower jaw 40, respectively. The full length of the respective electrode surfaces is best seen in FIG. 12C. Embodiments of the technology include configurations where the mutually complementary jaw surfaces do not extend the full length of the jaws, and the shape of the complementary surfaces need not necessarily be of consistent shape through the length of the jaws.

FIG. 12C is a proximal-looking perspective view of a distal aspect of an open set of jaws of laparoscopic electrosurgical device showing a V-shaped projection on the lower jaw, and a V-shaped recession on the upper jaw, as well as a central longitudinally-oriented gap in both V-shaped surfaces that form a through passage for a blade that is distally advanceable when the jaws are in a closed position. FIG. 12C further shows insulative strips 92 arranged across electrode tray or bipolar electrode surface 82 of upper jaw 80. Additionally, centrally disposed longitudinal gaps are visible in both the upper jaw and lower jaw. Gap 108A in lower jaw piece 60 and gap 108B in upper jaw 80 collectively form a through path for distal passage 106 of for blade 105 (not seen here, but shown in FIG. 2B).

Figure 13A:
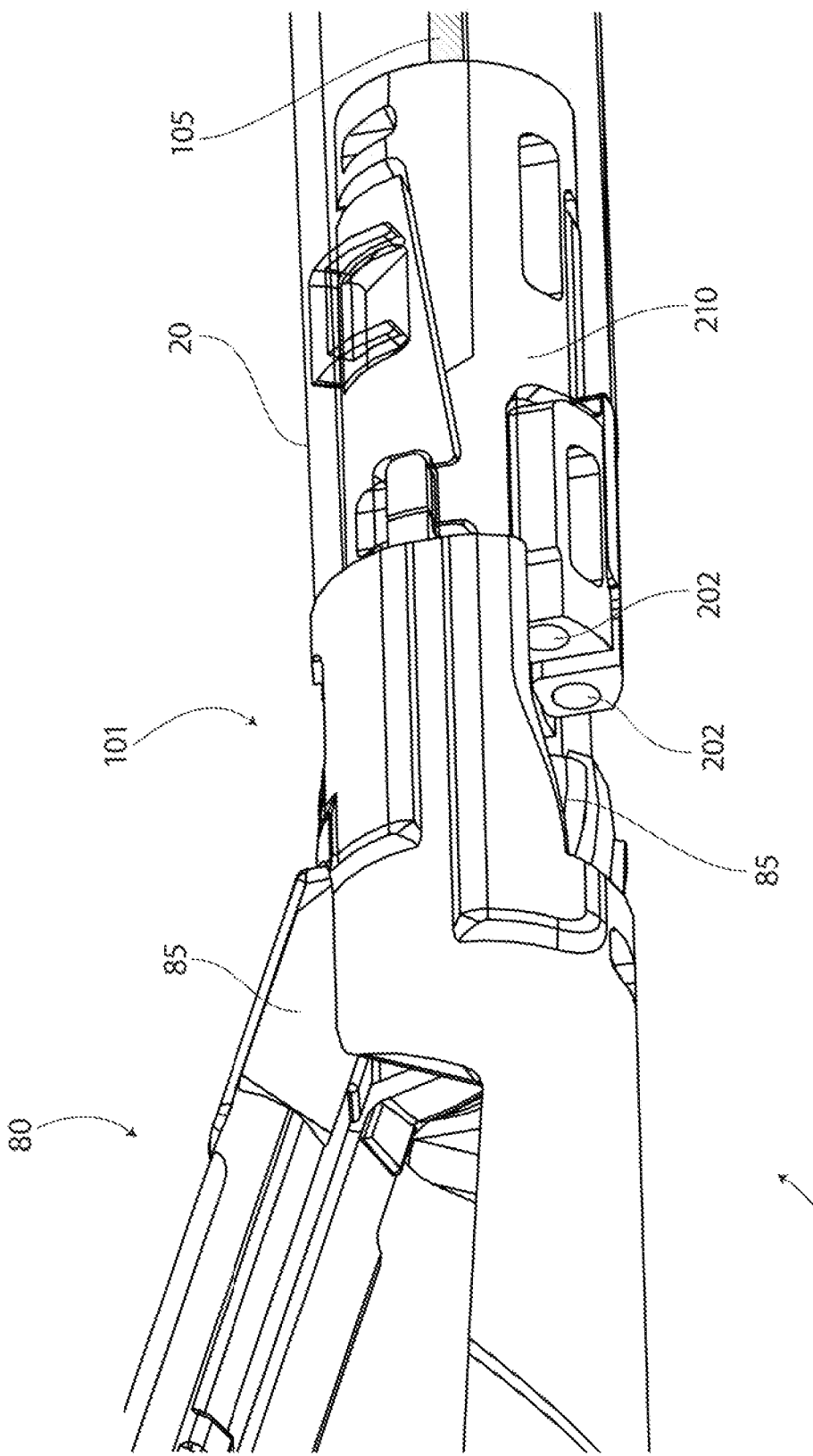
FIG. 13A is a proximal looking perspective view, partially exposed, of an embodiment of an electrosurgical device that shows aspects of the proximal portion of a set of jaws through which jaw actuator cables transit; the jaw actuator cables also serve as an electrical conduit to the upper jaw.

FIGS. 13A-15C all relate to in various ways to aspects of the junction between the proximal end of a jaw set and the distal end of a shaft, and to the separate and insulated electrical pathways to the upper jaw and lower jaw, respectively, per embodiments of the technology. FIGS. 13A-13F provide various views of an embodiment of an electrosurgical device that show aspects of the proximal portion of a set of jaws and the very distal portion of the shaft through which jaw actuator cables or wires transit. FIG. 13A provides an exposed proximal looking perspective view of a wire isolator or channelizing unit 210 disposed at the bottom (in this view) of the distal end of shaft 20. This isolator unit 210 guides the twinned actuator wires (not shown) from the center of the shaft to this cross-sectionally eccentric position such that the wire is positioned for its attachment to a proximal site of the arcuate track 85 of upper jaw 80 (see FIG. 8). Twin wire channels 202 may be seen in the distal face of channelizing unit 210. As noted above, embodiments of the actuator wire for upper jaw 80 also convey electrical current to upper jaw 80. Another function of wire isolator unit 210 is thus to insulate shaft 20 and proximal base 50 of the lower jaw from current being conveyed to the upper jaw.

Figure 13B:
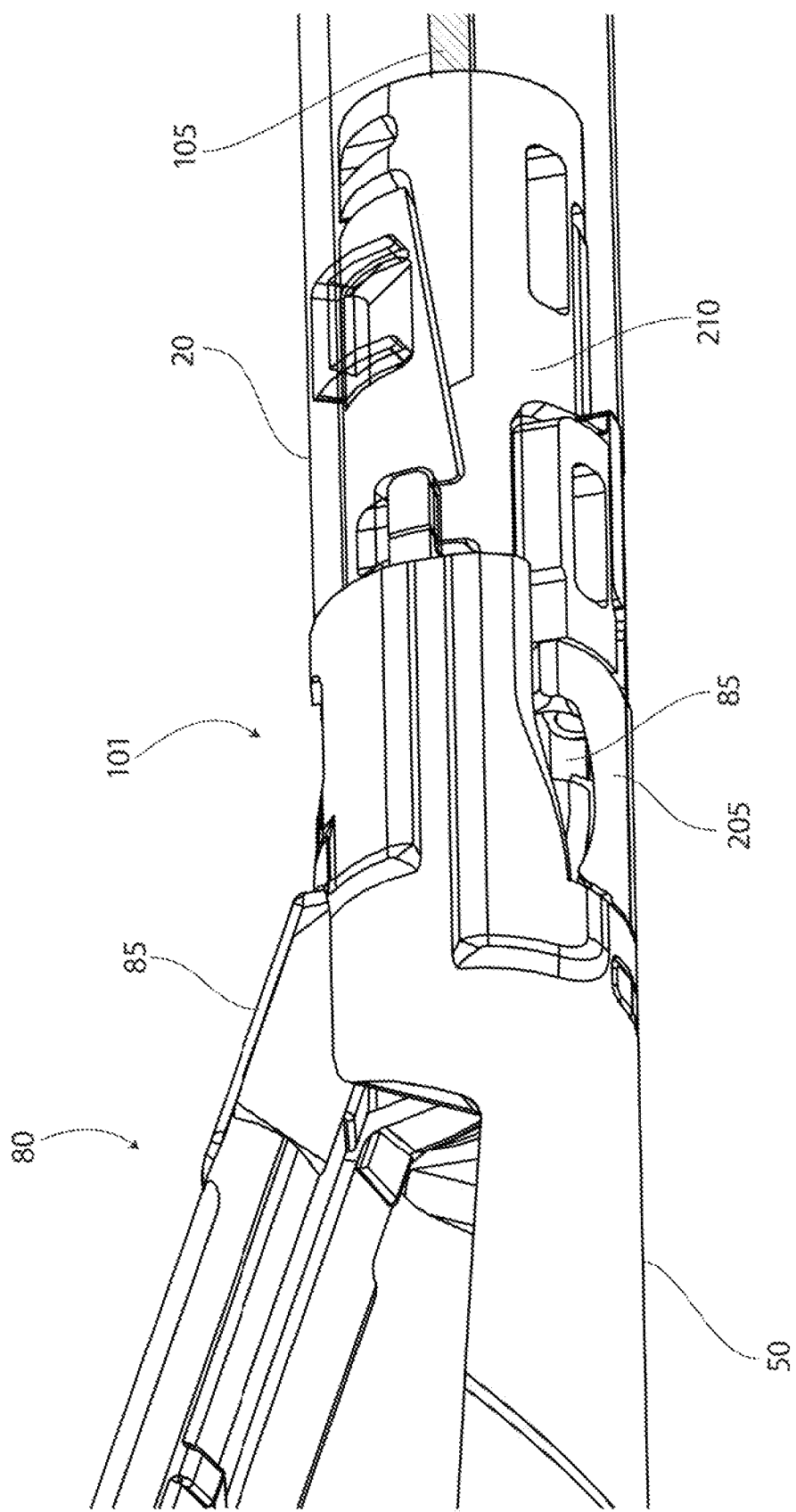
FIG. 13B is a proximal looking perspective view of an embodiment of an electrosurgical device that shows aspects of the proximal portion of a set of jaws through which jaw actuator cables transit.
Figure 13C:
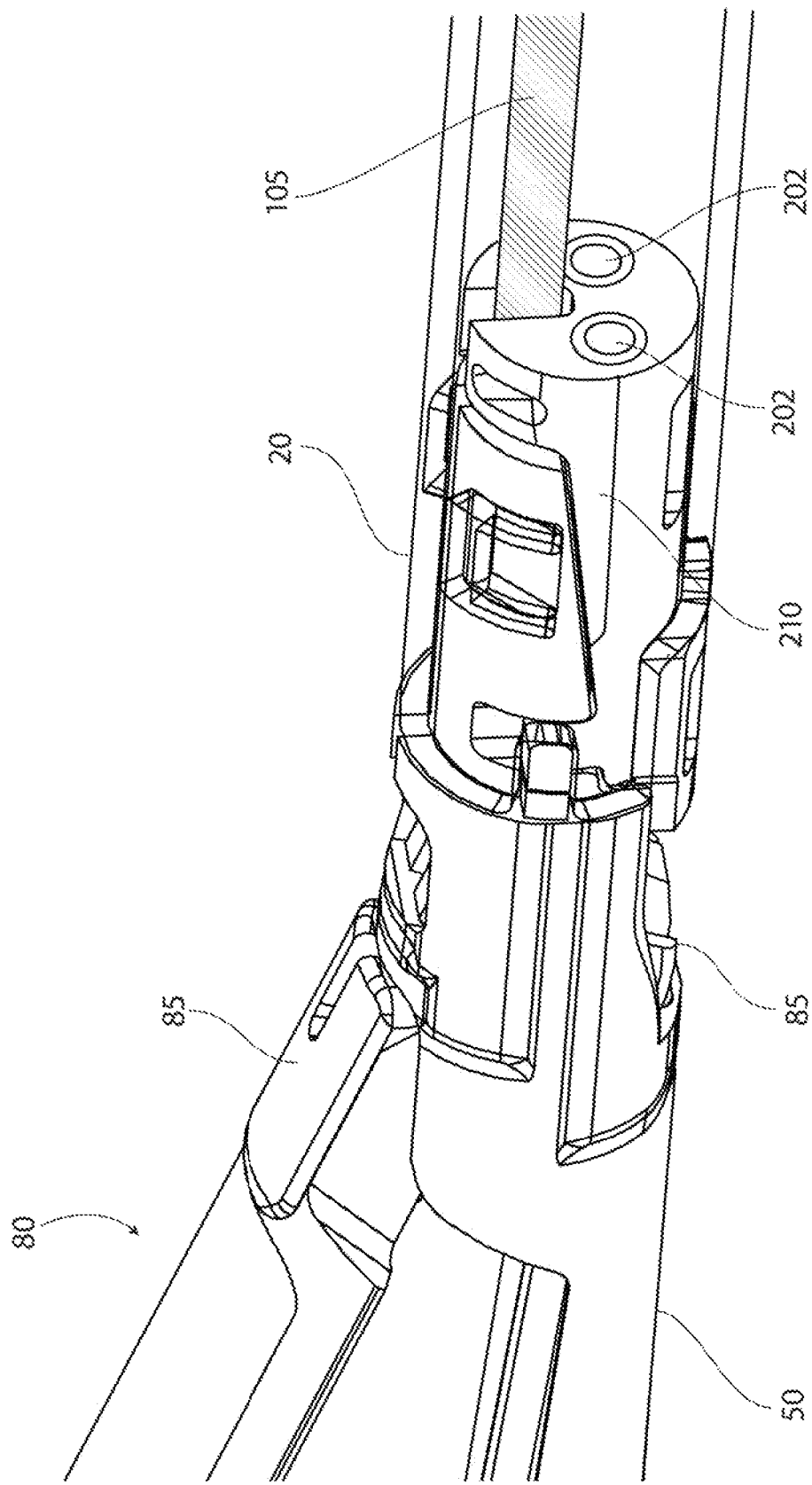
FIG. 13C is a distal looking transparent perspective view of an embodiment of an electrosurgical device that shows aspects of the proximal portion of a set of jaws through which jaw actuator cables transit.
Figure 13D:
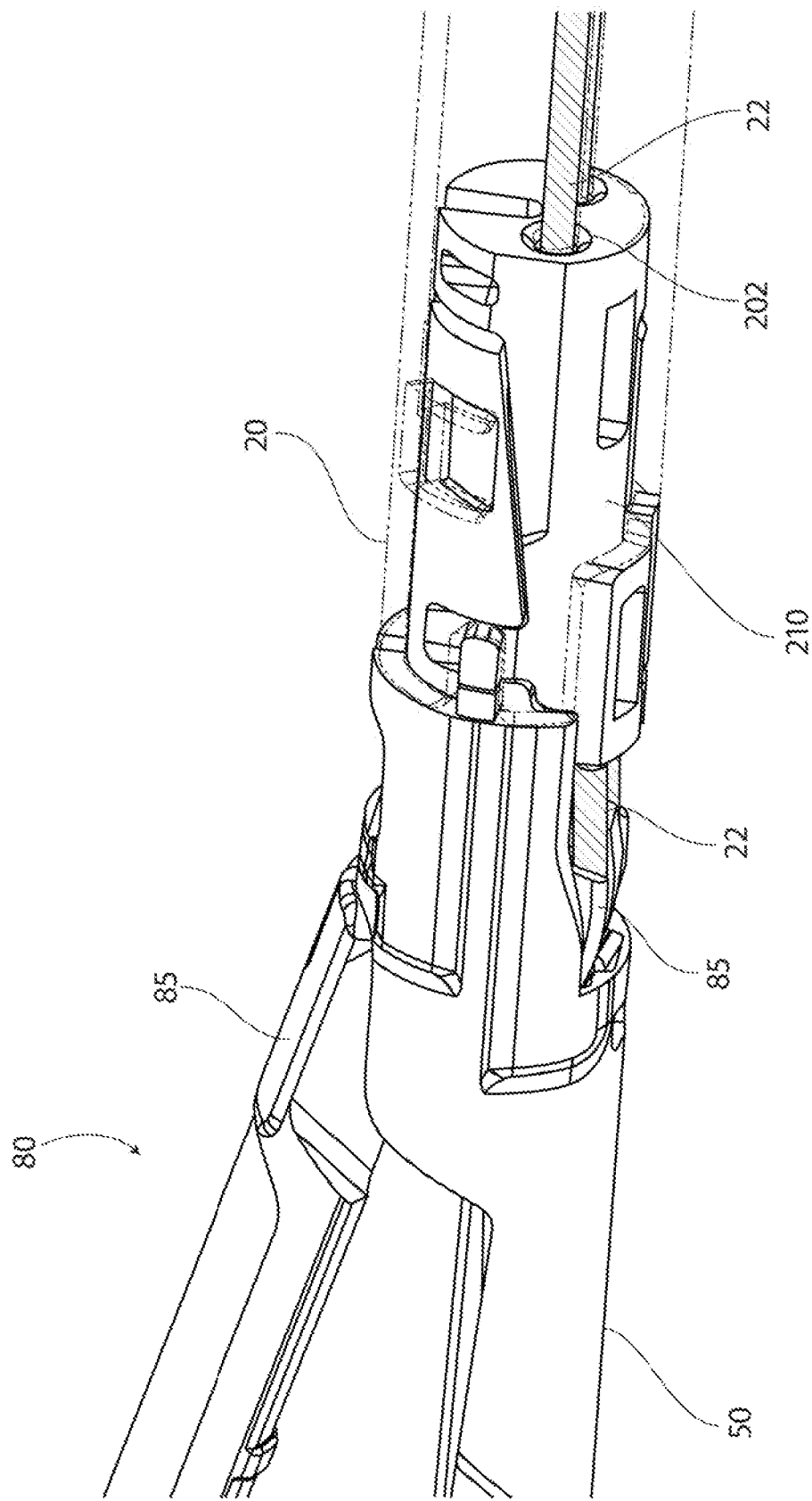
FIG. 13D is a distal looking transparent perspective view of an embodiment of an electrosurgical device similar to FIG. 13C, that shows aspects of the proximal portion of a set of jaws through which jaw actuator cables transit, with the cables in place.

FIG. 13B has the same perspective orientation as that of FIG. 13A, but shows a cable retaining plate 205 in place over an area where cables emerge from a central transit through the shaft and are diverted to an eccentric site, where they are attached to a proximal aspect of the pivotable upper jaw. Cable retaining plate 205 secures cables through this portion of their path, and also provides electrically insulates the wires within this space. FIG. 13C is a distal looking transparent view that shows a cable isolator unit with parallel cable channels. FIGS. 13C and 13D both provide a view of blade 105 and its path through isolator unit 210, as well as the distal openings of wire channels 202. FIG. 13D provides a view similar to that of FIG. 13C, but with the cables 22 in place.

Figure 13E:
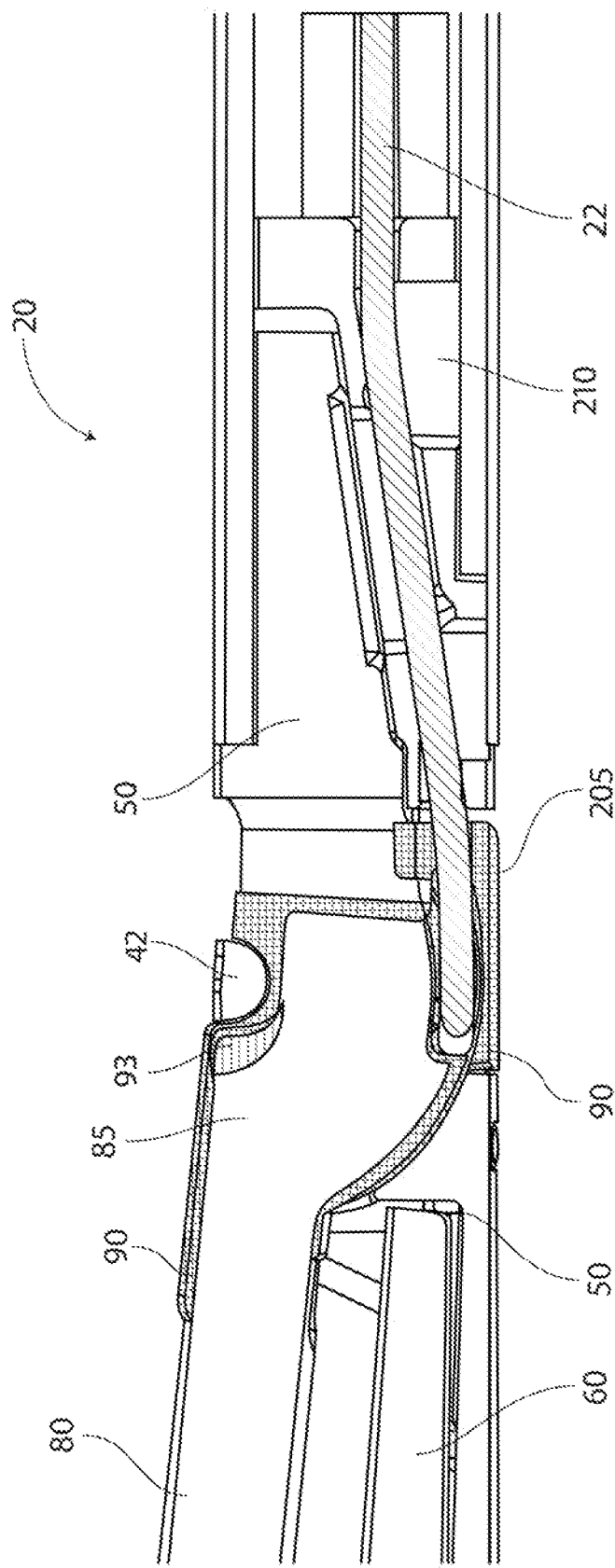
FIG. 13E is a longitudinal section view, slightly offset from midline, showing the paths of cables through the distal portion of the shaft and into the proximal aspect of the jaws.

FIG. 13E is a longitudinal section side view, slightly offset from midline, showing the paths of cables 22 through the distal portion of the shaft and into the proximal aspect of the jaws. The closer of the twinned cables 22 can be seen being channeled from its substantially central position within the main body of the shaft to a peripheral position at the very distal end of the shaft. As cable 22 transitions into the proximal base of the jaws, it wraps around attachment site 99 of the base of upper jaw 80. Polymer layer 90 can be seen as an outline surrounding a major portion of the arcuate track portion 85 of upper jaw 80, however cable attachment site is not covered with polymer. The bare aspect of cable attachment site 99 can also be seen in FIGS. 14A, 14B, and 15A, and 15B. Other aspects of the arcuate track portion of the upper jaw that engage surfaces of the base portion 50 of the lower jaw are coated with polymer 90 such that upper and lower jaw surfaces are insulated from each other. Accordingly, twinned cable 22 makes direct electrical contact with upper jaw 80 to the exclusion of contact with lower jaw piece 50. Cable retaining plate 205 (see FIG. 13B) is formed from plastic, and it thus also serves an insulative function.

Figure 13F:
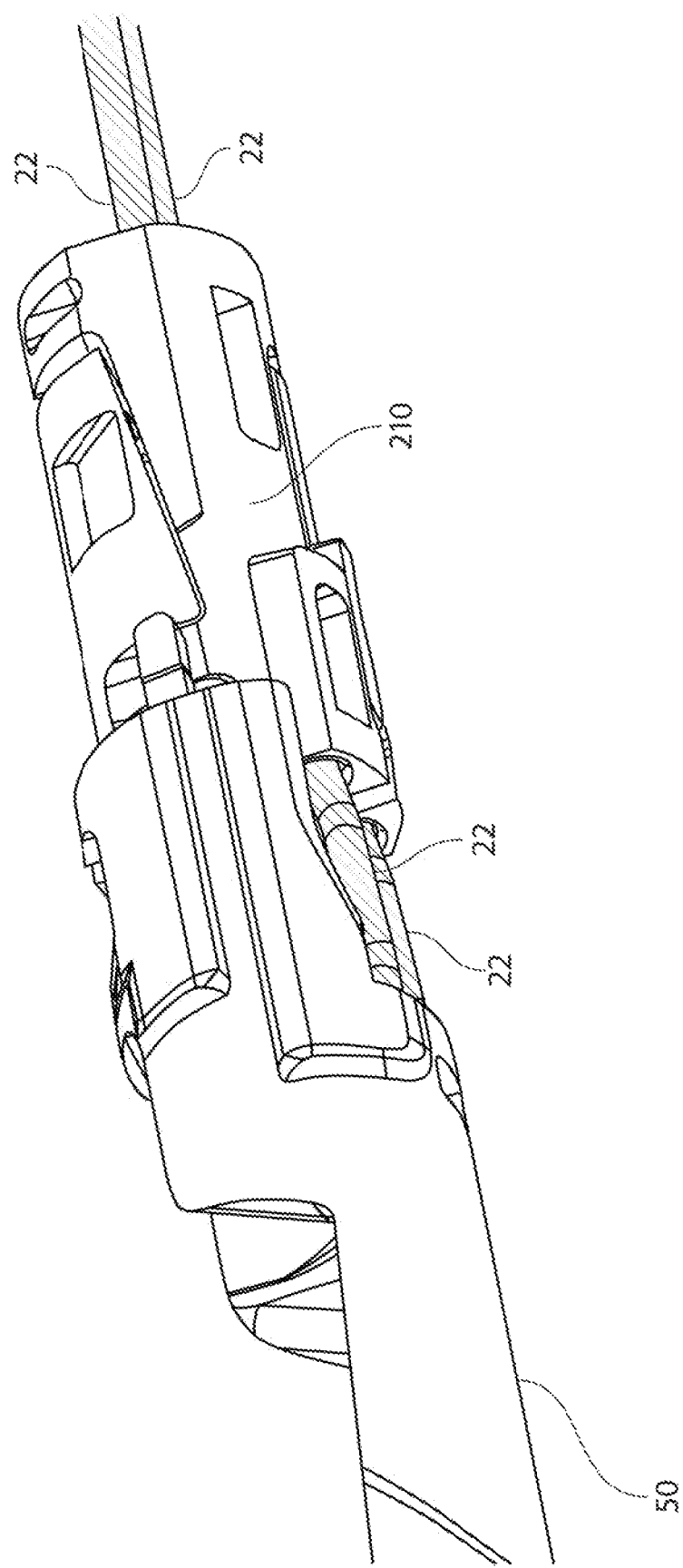
FIG. 13F is proximal looking perspective view of the proximal end of a lower jaw that is inserted into the distal end of a shaft, further showing engagement of the proximal end of the shaft with a cable isolator unit.

FIG. 13F is proximal looking perspective view of the proximal end of a lower jaw piece 50 that is inserted into the distal end of a shaft, further showing engagement of the proximal end of the shaft with a cable isolator unit. FIG. 13E and FIG. 13F also generally depict a distal aspect of the electrical path that provides radiofrequency energy to the upper jaw, to the exclusion of the lower jaw. The electrical path that provides radiofrequency to the lower jaw is the shaft 20 as a whole. Aspects of the proximal portions of the electrical paths to the upper and lower jaws are shown in FIGS. 16A-16D.

Figure 14A:
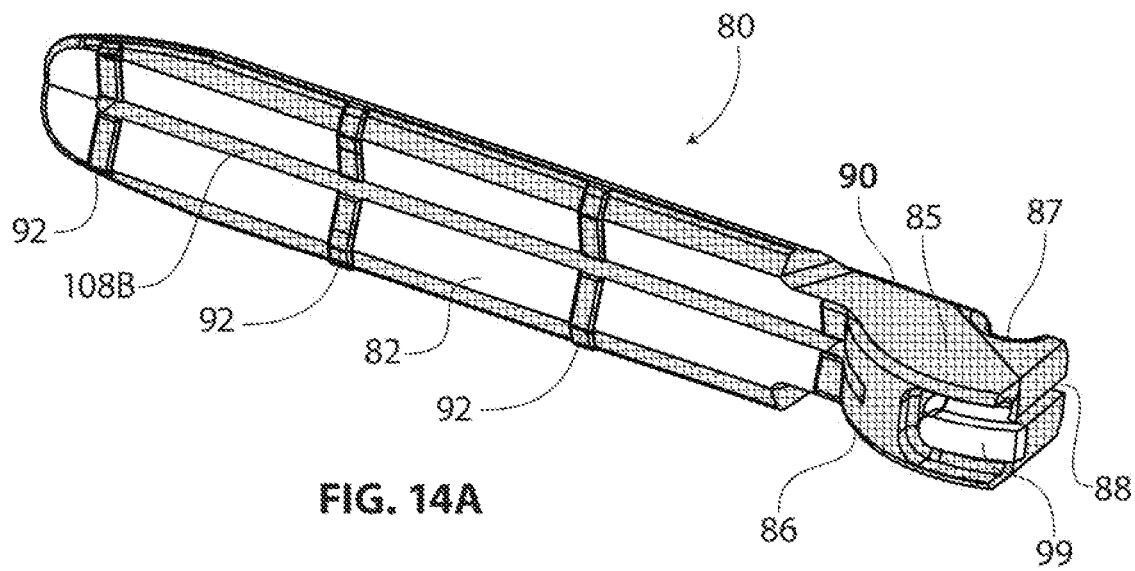
FIG. 14A is a bottom perspective view of an embodiment of an upper jaw of an electrosurgical device that shows plastic insulator layer overlaying the electrode.
Figure 14B:
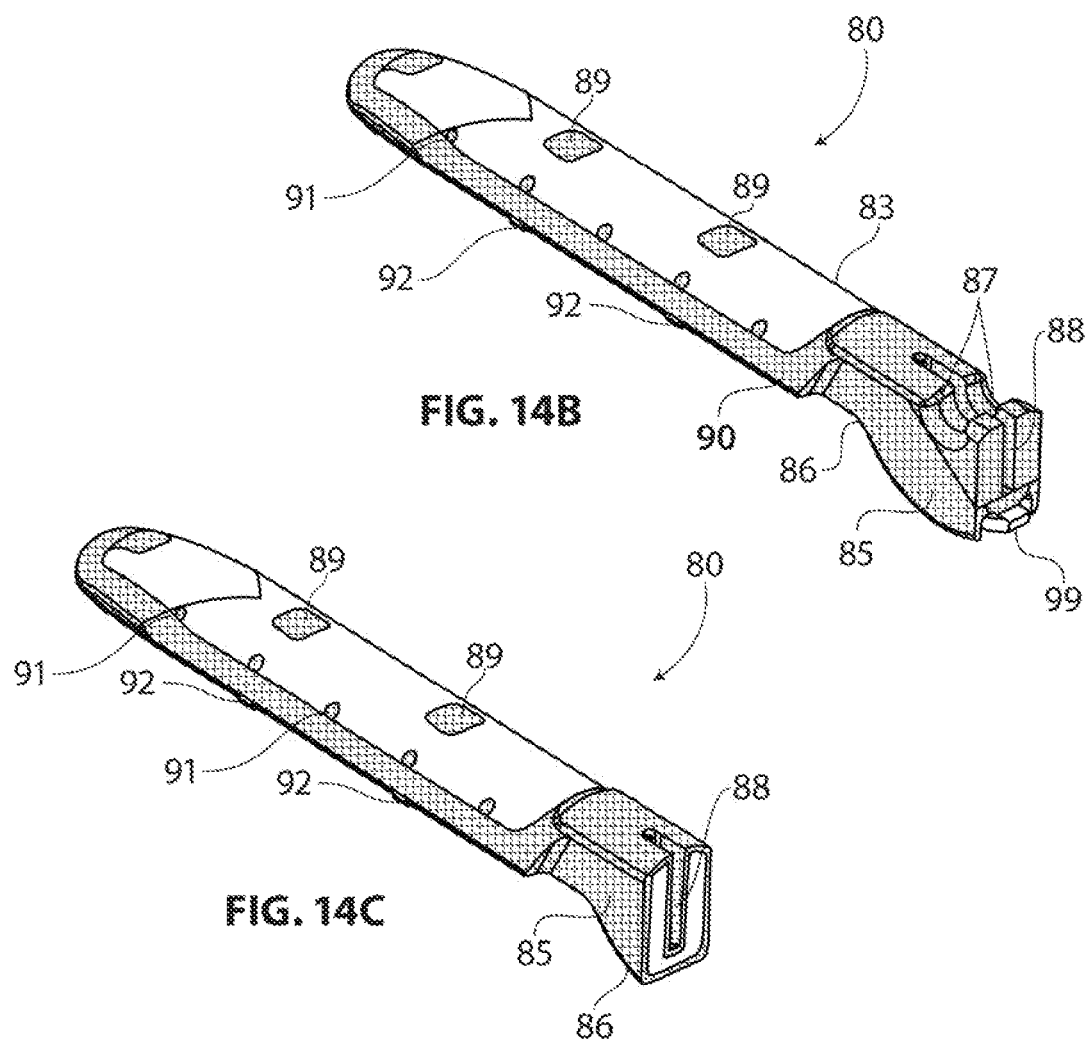
FIG. 14B is a top perspective view of an embodiment of an upper jaw of an electrosurgical device that shows polymer insulator layer overlaying the electrode.
Figure 14C:
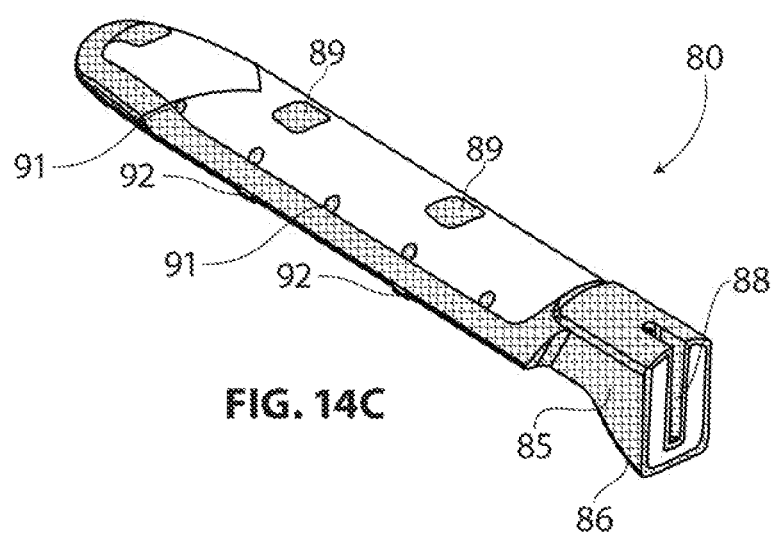
FIG. 14C is a top perspective view of an embodiment of an upper jaw of an electrosurgical device that shows polymer insulator layer overlaying the electrode, with the proximal portion of the jaw truncated to expose a cross section.

FIGS. 14A-14C provide various non-transparent views of an embodiment of an insulative layer 91 that covers aspects of an upper jaw 80 of an electrosurgical device. FIG. 14A is a bottom perspective view of an embodiment of an upper jaw of that shows plastic insulator layer overlaying aspects of an electrode. FIG. 14B is a top perspective view of an embodiment of an upper jaw of an electrosurgical device that shows polymer insulator layer overlaying peripheral and proximal aspects of the electrode. FIG. 14C is a top perspective view of an embodiment of an upper jaw that shows polymer insulator layer overlaying the electrode, with the proximal portion of an jaw truncated to expose a cross section. FIGS. 14A-14C show polymer layer 90 (bolded indicator) in a relatively light rendering that covers a major portion of upper jaw 80; uncoated metal is shown in a darker rendering. These figures also provide a good view of aspects of the arcuate track 85 portion of upper jaw 80, including the upper and smaller arcuate track surface 87, the lower and greater arcuate track surface 86, and a central slot 88, which is contiguous with blade track 106 (as also seen in FIG. 12C).

In FIG. 14A, polymer coating 90 is seen around the periphery of the exposed metal electrode surface 82 and actuator attachment site 99 in FIG. 14A. The more lightly rendered polymer overlay also takes the form of insulative strips 92 that are arranged across the surface of electrode 82. The thickness of the polymer coating 90 is in the range of about 0.005 inch to about 0.015 inch. The polymer layer that takes the form of insulative strips 92 stands off from the broader electrode surface 82 by about 0.004 inch to about 0.008 inch, but its overall thickness is greater because it is positioned in a trough, as seen in FIG. 5A (trough 84 within electrode surface 142).

FIGS. 14B and 14C show exposed or uncoated metal on the upper surface 83 of upper jaw 80. FIG. 14B shows that insulative layer 90 fully coats the proximal aspect of upper jaw 80, including the surfaces of arcuate track portion 85. Receptacles 89 on the upper aspect of the jaw are filled with polymer 90, as the polymer fills these receptacles such that it is a continuous fill from the lower electrode side of the jaw (as seen in FIG. 14A) through to a top surface exposure.

FIG. 14C differs from FIG. 14B in that the proximal aspect of the jaw is truncated with a cross section exposure 85C just distal of smaller or upper concentric surface of arcuate track 85. FIGS. 14B and 14C also show insulator strip anchoring receptacles 89 on the top of jaw 80. These receptacles penetrate the metal and fill with polymer during the coating process, anchoring the coating against the electrode surface. On the bottom surface of the electrode, receptacles 89 are positioned within blade track 108B (see FIG. 14A). Peripheral anchoring recesses 91 are arranged around the edge of jaw 80, also serving to stabilize polymer layer 90 in place.

Figure 15A:
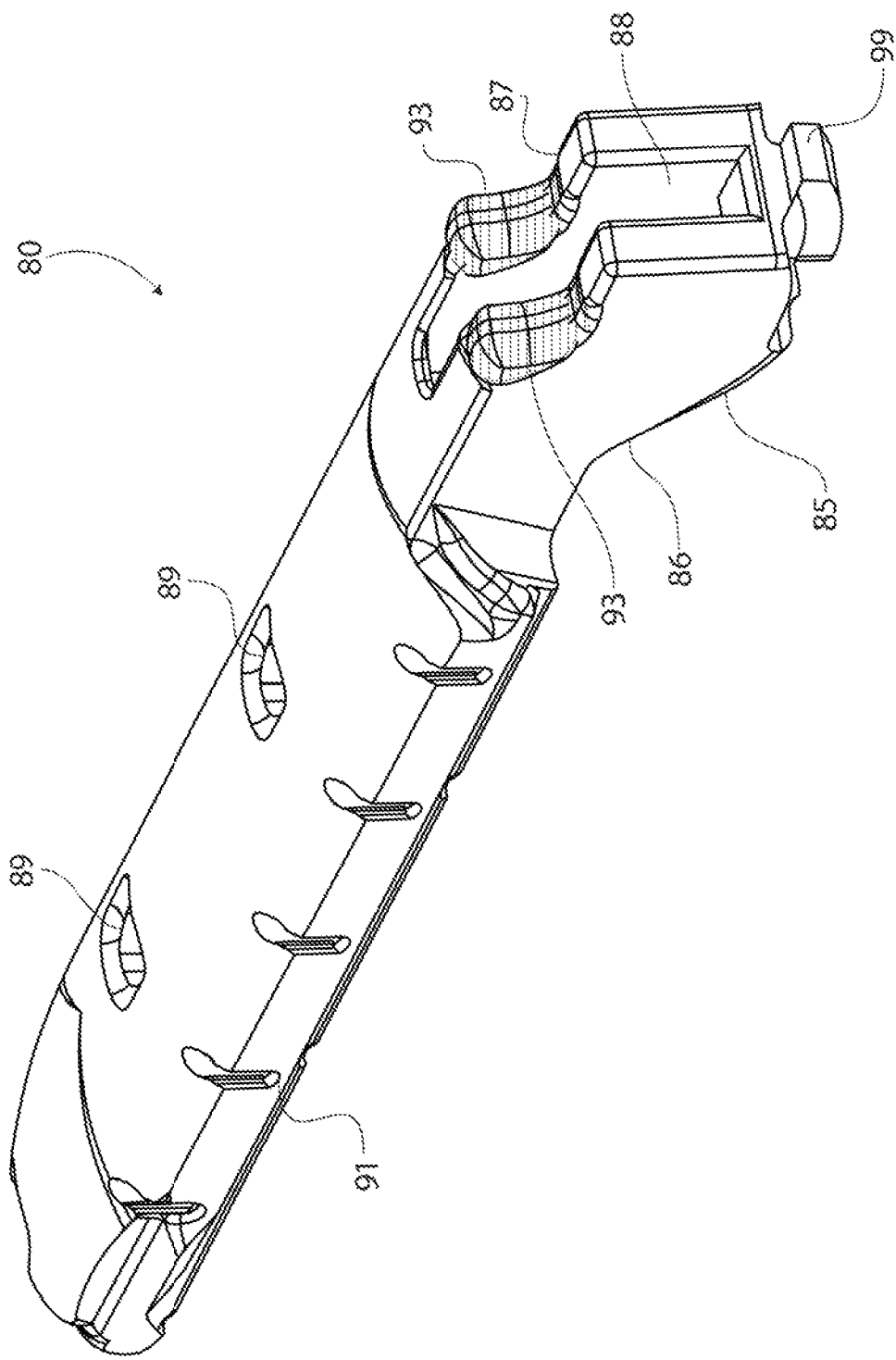
FIG. 15A is a top perspective view of an embodiment of an upper jaw of an electrosurgical device that shows points of ceramic overlaying the electrode at abrasive stress points.
Figure 15C:
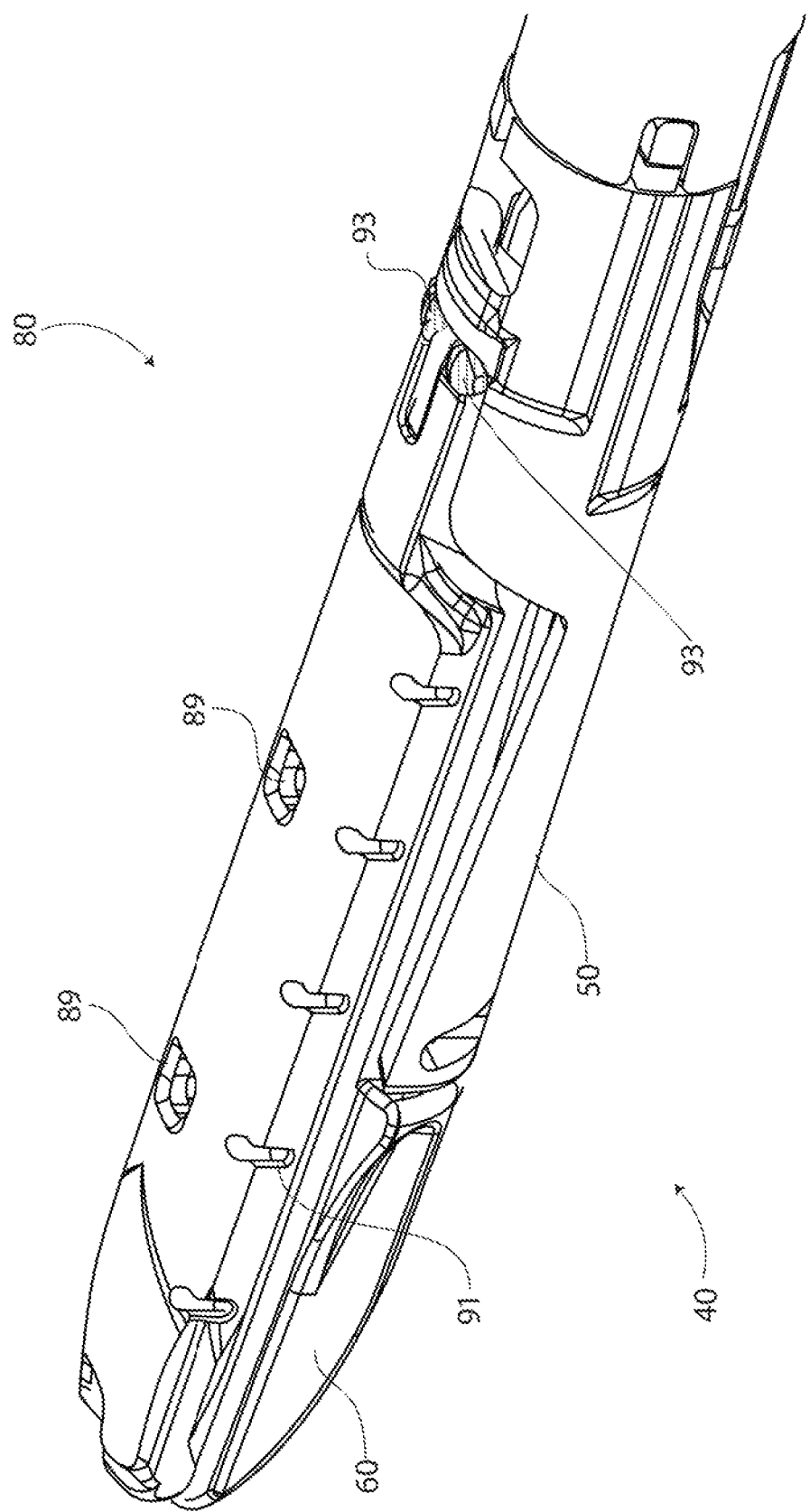
FIG. 15C is a top perspective view of an embodiment of a pair of closed jaws of an electrosurgical device that shows points of ceramic overlaying the electrode at abrasive stress points as they are embedded in a more extensive polymer layer.

FIGS. 15A-15C provide various views of an embodiment of an insulative layer 90 that covers aspects of an upper jaw of an electrosurgical device and which includes areas of ceramic reinforcement 93 at particular sites that can be subject to abrasive stress or erosion. These abrasively stressed sites are on the upper surface of arcuate track 85 (more particularly the smaller concentric surface 86) of upper jaw 80. When the jaws pivot, these sites rotate against the upper concentric surface of the arcuate track of the lower jaw (see FIGS. 3A-3C and FIG. 8). The stress applied to this area of rotational engagement of the upper and lower jaws comes from the tension that can be applied by the jaw actuator wire.

FIG. 15A is a top perspective view of an embodiment of an upper jaw that shows ceramic points 93 overlaying the electrode at abrasive stress points. This view does not include an overlaying polymer layer. FIG. 15B is a top perspective view of an embodiment of an upper jaw that shows points of ceramic 93 overlaying the electrode at abrasive stress points as they are embedded in a more extensive polymer layer 90. FIG. 15C is a top perspective view of an embodiment of a pair of closed jaws that shows ceramic points 93 overlaying the electrode at abrasive stress points as they are embedded or disposed within a more extensive polymer layer 90.

Figure 16A:
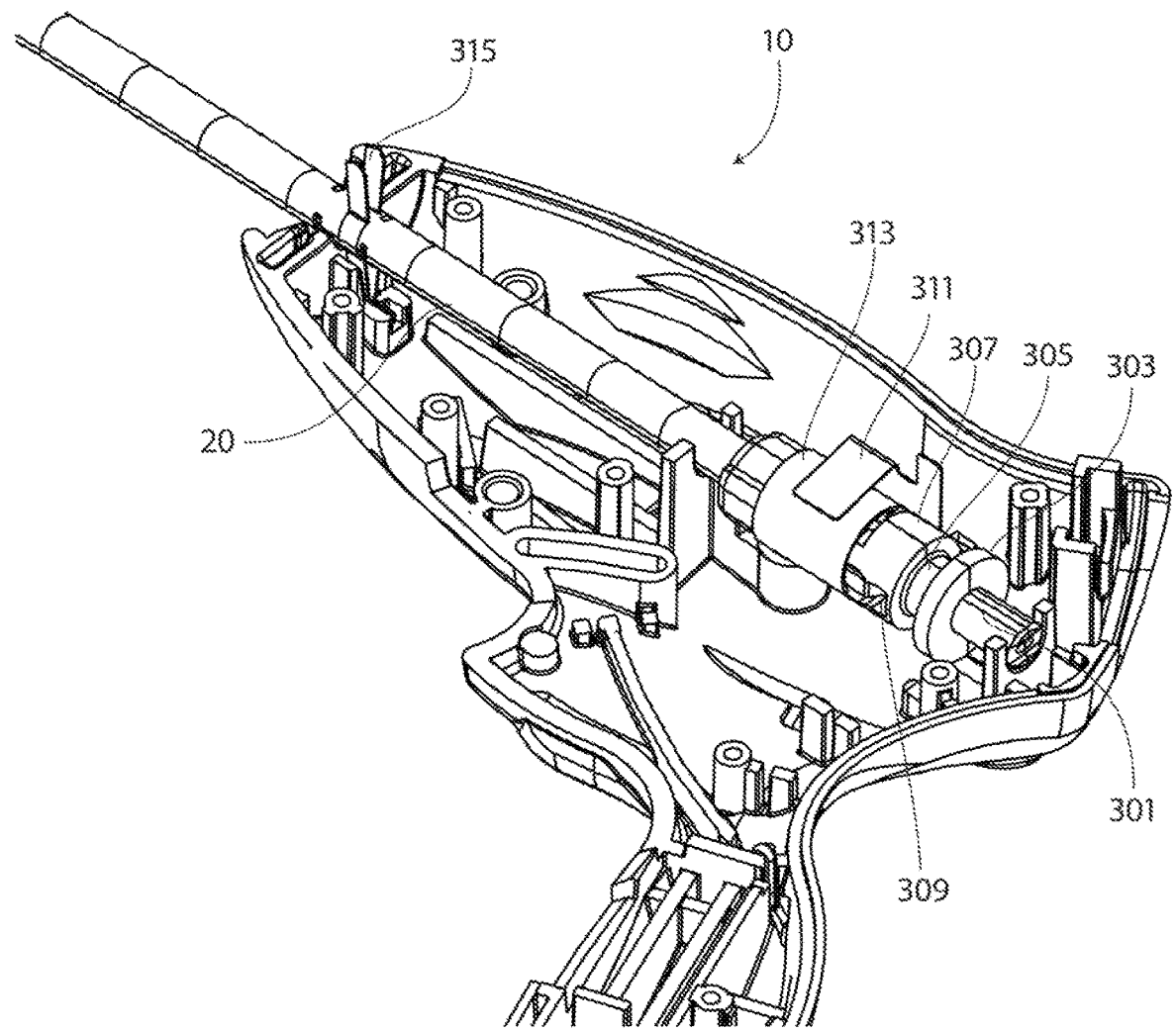
FIG. 16A is an exposed perspective view of a handle of an embodiment of an electrosurgical device that shows aspects of the proximal end of a rotatable shaft.
Figure 16B:
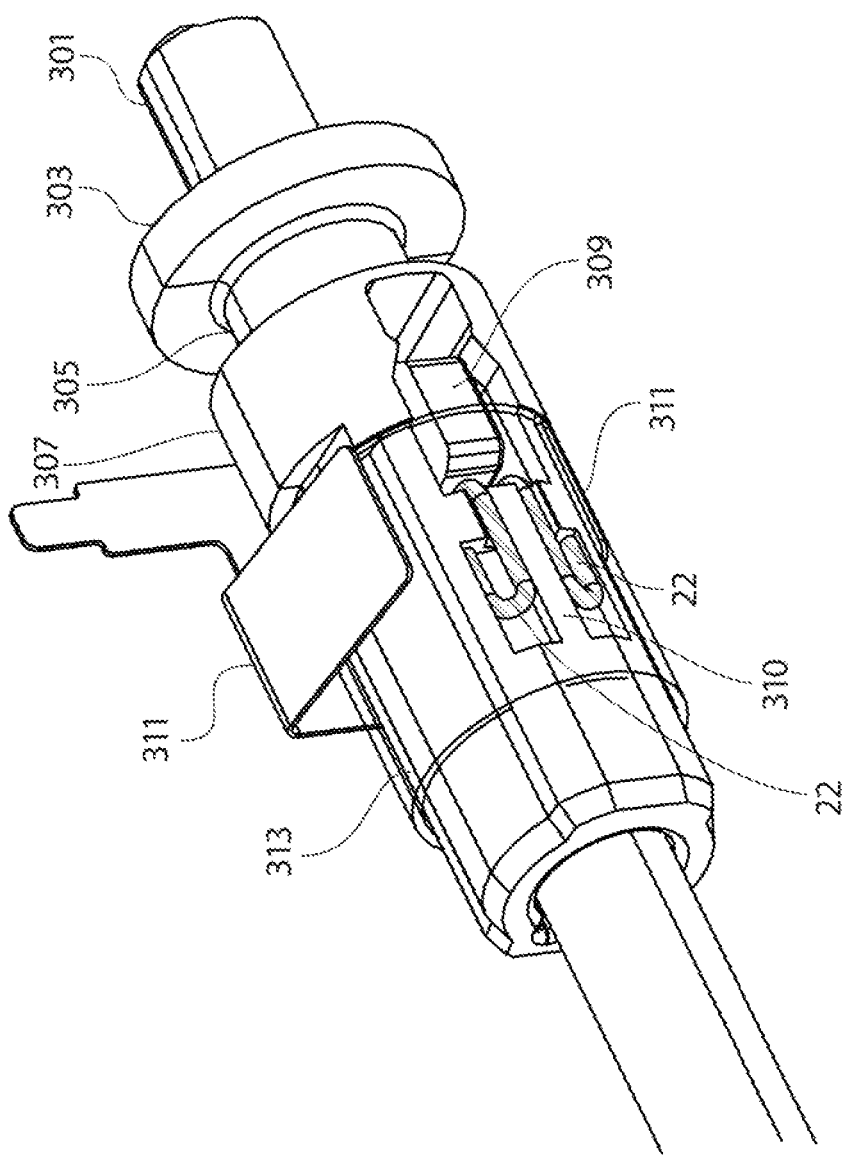
FIG. 16B is a perspective view of an isolated proximal end of a rotatable shaft.
Figure 16C:
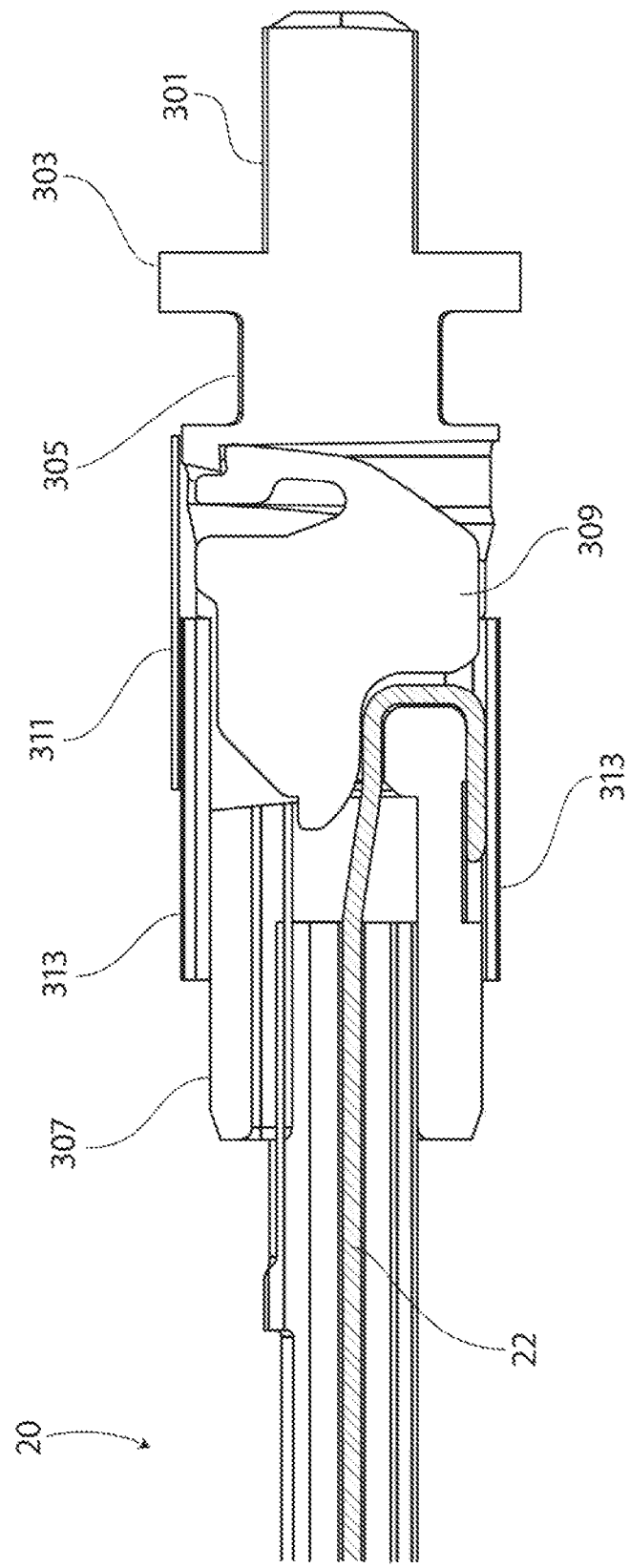
FIG. 16C is a midline sectional view of an isolated proximal end of a rotatable shaft.
Figure 16D:
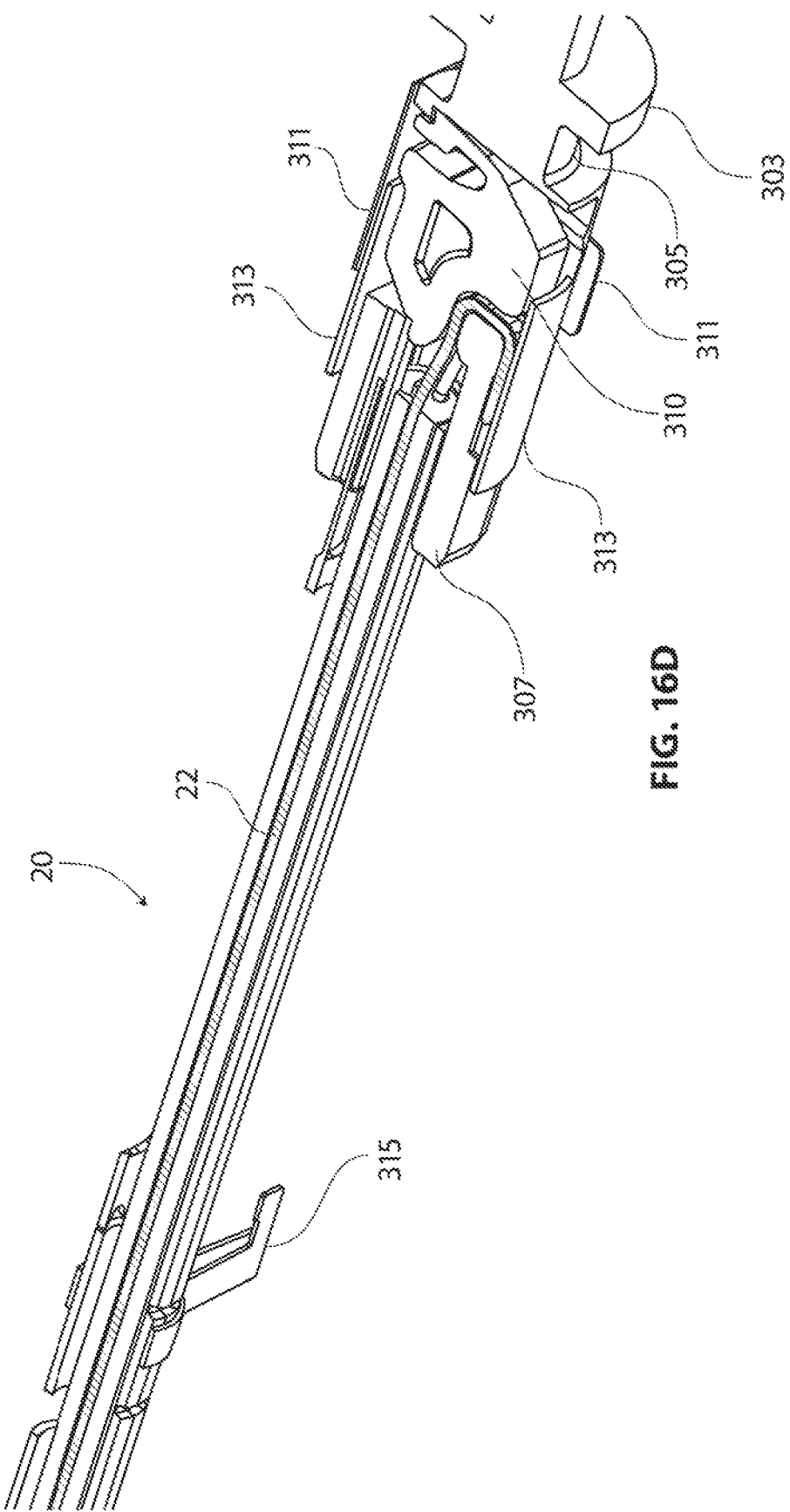
FIG. 16D is a midline sectional view of a proximal portion of a rotatable shaft.

FIGS. 16A-16D show various views of the proximal portion of an embodiment of a rotatable shaft 20 and electrical and mechanical components associated with the shaft that are housed in the handle 10 of an electrosurgical device. FIG. 16A is an exposed distal looking perspective view of a handle of an embodiment that shows aspects of the proximal end of a rotatable shaft. FIG. 16B is a proximal looking perspective view of an isolated proximal end of a rotatable shaft. FIG. 16C is a midline sectional side view of an isolated proximal end of a rotatable shaft. FIG. 16D is a midline exposed sectional view of a portion of the rotatable shaft that is housed in the handle.

As seen in these various views, the proximal end of shaft 20 terminates into a proximal shaft-associated assembly that includes an actuation collar 307 around which is slidably wrapped within a power tube 313. Proximal to actuation collar 307 are a control flange 303 and a control post 301. A jaw actuator engagement groove 305 is disposed between control flange 303 and control post 301. The actuation collar and its wrap around power tube are disposed within the partially enclosing U-shaped proximal electrical connector 311. The actuation collar and power tube are both rotatable and slidable within the proximal electrical connector. Actuation of the rotation of the shaft (and the actuation collar and power tube) is controlled by rotation actuator 12, as shown in FIGS. 1A-1D, but not shown in this view. Actuation of the distal-proximal slidability of the collar and power tube is controlled by a mechanical linkage that is ultimately connected to jaw actuator grip 15 as shown in FIGS. 1B-1D. The jaw actuator linkage engages the shaft-associated assembly within groove 305.

The proximal electrical connector 311 delivers radiofrequency electrical energy to power tube 313 through a secure but slidable contact that is maintained regardless of the rotational position of the power tube, and regardless of the distal to proximal translational position of the power tube. Electrical energy is conveyed by this path from a generator that is part of a larger electrosurgical system to cables 22 that terminate proximally within actuation collar 307 at a proximal cable attachment site 310. A collar plug 309 that fills an asymmetric space within a proximal aspect of actuation collar 307 serves in several mechanical capacities, one of them being to secure cables 22 in their attachment to attachment site 310. Cables 22 terminate distally in an attachment to an upper jaw, as shown in FIG. 8.

Electrical energy is also conveyed to distal electrical connector 315 from a system generator, and electrical connector 315 delivers energy to the shaft 20, which then conducts energy to the lower jaw piece 50. By these approaches, electrical paths to the upper jaw and lower jaw, respectively are segregated within the handle. Separate paths are maintained throughout the main body of the shaft, where electrical energy to the upper jaw travels through the centrally disposed twin cables 22, and where electrical energy to the lower jaw travels through the columnar shaft 20. Segregation of these two paths at the junction of the shaft and the jaws is described above in the context of FIGS. 13A-13F.

Unless defined otherwise, all technical terms used herein have the same meanings as commonly understood by one of ordinary skill in the art of surgery, including electrosurgery. Specific methods, devices, and materials are described in this application, but any methods and materials similar or equivalent to those described herein can be used in the practice of the present invention. While embodiments of the invention have been described in some detail and by way of illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices or equipment, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations may have been advanced in furtherance of providing an understanding of the technology, the appended claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims appended to the patent application, including the full range of equivalency to which each element thereof is entitled.

The invention claimed is:

1. An electrosurgical device comprising:
a set of opposing jaws disposed distal to a shaft, the jaws comprising a first jaw and a second jaw, the first jaw comprising a proximal jaw piece having a distal end and a distal jaw piece having a proximal end, the proximal end of the distal jaw piece received in the proximal jaw piece, and the distal end of the proximal jaw piece received in the distal jaw piece, wherein the jaw pieces of the first jaw are pivotably connected with each other, each jaw comprising a tissue-engaging surface with at least one bipolar electrode disposed thereon, wherein the distal jaw piece of the first jaw comprises the tissue-engaging surface of the first jaw, the jaws configured to deliver radiofrequency energy to a target tissue, each of the jaws comprising a longitudinal axis, the tissue-engaging surface of each jaw having a complementary self-aligning configuration with respect to the longitudinal axis of the other jaw;
a blade positioned on a longitudinally disposed blade track, the track having a proximal end and a distal end, wherein the blade may be positioned at a home position at the proximal end of the track, at the distal end of the track, or at any point along the track between the distal and proximal ends of the track;
a pinless rotation mechanism comprising rotatably cooperative features of the first jaw and the second jaw that connect the jaws together and enable the jaws to pivot between an open position and a closed position, the pinless rotation mechanism creating a common center of rotation; and
a biasing member attached to one of the proximal jaw piece and distal jaw piece, and bearing against the other of the proximal jaw piece and distal jaw piece, the biasing member exerting a biasing force that urges a distal end of the distal jaw piece toward the second jaw so as to maintain the distal jaw piece in a default biased position when the first and second jaws are in the open position,
wherein, when the jaws are moving from the open position toward the closed position, a first point of mutual contact between the jaws occurs at a distal end of each jaw due to the default biased position of the distal jaw piece, and
wherein the distal jaw piece of the first jaw is mounted at a substantially central point on a distal aspect of the proximal jaw piece of the first jaw such that, when the jaws are moving from the open position toward the closed position, a proximal end of the tissue-engaging surface of the first jaw moves away from the proximal jaw piece and elevates above an upper edge of a proximal portion of the proximal jaw piece of the first jaw.

2. The electrosurgical device of claim 1, wherein the rotatably cooperative features of the first jaw and the second jaw comprise:
a proximal aspect of the first jaw having a first arcuate track; and
a proximal aspect of the second jaw having a second arcuate track, the first and second arcuate tracks being mutually complementary and slidably engageable with each other, the second arcuate track substantially residing within an enclosure formed by the first arcuate track.

3. The electrosurgical device of claim 1, wherein the first arcuate track comprises two concentric surfaces facing each other, one smaller and the other larger, and the second arcuate track comprises two concentric surfaces facing away each other, one smaller and the other larger, and wherein the smaller concentric surfaces of the first and second track are complementary to each other, and wherein the larger concentric surfaces of the first and second track are complementary to each other, and wherein the second arcuate track substantially resides within an enclosure formed by the first arcuate track.

4. The electrosurgical device of claim 1, wherein a proximal base of the first jaw is fixed with respect to the shaft, and wherein the second jaw is pivotable with respect to the shaft.

5. The electrosurgical device of claim 1, wherein the second jaw is unitary.

6. The electrosurgical device of claim 1, wherein the proximal piece of the first jaw is fixed with respect to the shaft, and wherein the second jaw pivotable with respect to the shaft.

7. The electrosurgical device of claim 6, wherein the first jaw is fixed with respect to the shaft, and
wherein the second jaw comprises a proximal jaw piece that is pivotable with respect to the shaft, a distal jaw piece that is pivotable with respect to the proximal piece, and a pivotable assembly connecting the proximal jaw piece and the distal jaw piece.

8. The electrosurgical device of claim 1, wherein when the jaws are in the open position, the proximal home position of the blade is configured such that the movement of the blade in a distal direction is blocked.

9. The electrosurgical device of claim 1, wherein the set of jaws, when closed, has a diameter no greater than about 5 mm.

10. The electrosurgical device of claim 1, wherein the shaft has a diameter no greater than about 5 mm.

11. The electrosurgical device of claim 1, wherein the self-aligning configuration of the tissue-engaging surfaces of the jaws comprises complementary longitudinally aligned features disposed along a substantial entirety of a length of each jaw.

12. The electrosurgical device of claim 1, wherein the self-aligning configuration of the tissue-engaging surfaces of the jaws comprises complementary longitudinally aligned aspects of the jaws that comprise a substantial entirety of the tissue engaging surfaces of each jaw.

13. The electrosurgical device of claim 1, further comprising:
a handle portion proximal to the shaft;
a jaw actuator associated with the handle portion configured to actuate a mechanical capability of the jaws; and
an actuator wire connected proximally to the actuator mechanism and connected distally to the set of jaws.

14. The electrosurgical device of claim 13, wherein the actuator wire is configured to actuate a pivoting of the jaws between the open position and the closed position by pivoting a second jaw with respect to at least a proximal piece of the first jaw, the proximal piece of the first jaw being fixed with respect to the shaft.

15. The electrosurgical device of claim 13, wherein the actuator wire is configured to actuate a pivoting of the jaws between the open position and the closed position, and wherein the actuator wire is further configured to deliver RF energy to at least one of the two opposing jaws.

16. The electrosurgical device of claim 13, wherein the actuator wire is configured as a push and pull mechanism, wherein a distally-directed push from the wire moves the jaws to their open position, and a proximally-directed pull from the wire moves the jaws to their closed position.

17. The electrosurgical device of claim 1, further comprising a handle portion proximal to the shaft, and an energy-delivery wire extending distally from the handle portion to the jaws, the energy-delivery wire configured to perform a mechanical function with regard to a capability of the jaws.

18. The electrosurgical device of claim 1, wherein each of the first jaw and the second jaw comprises a metal portion, and wherein a substantial entirety of the metal portion of the first jaw and a substantial entirety of the metal portion of second jaw each comprise an electrode.

19. The electrosurgical device of claim 1, further comprising a shaft rotational actuator positioned in association with a handle portion of the device.

20. The electrosurgical device of claim 19, wherein the shaft rotational actuator is configured to be able to rotate freely in both clockwise and counter clockwise directions, such actuator rotation being translatable to shaft rotation.

21. The electrosurgical device of claim 1, wherein the distal end of the proximal jaw piece comprises a tongue portion received in a recess in the distal jaw piece.

22. An electrosurgical device comprising:
a set of opposing jaws disposed distal to a shaft, the jaws comprising a first jaw and a second jaw, the first jaw comprising a proximal jaw piece having a distal end and a distal jaw piece having a proximal end, the proximal end of the distal jaw piece received in the proximal jaw piece, and the distal end of the proximal jaw piece received in the distal jaw piece, wherein the jaw pieces of the first jaw are pivotably connected with each other, each jaw comprising a tissue-engaging surface with at least one bipolar electrode disposed thereon, wherein the distal jaw piece of the first jaw comprises the tissue-engaging surface of the first jaw, the jaws configured to deliver radiofrequency energy to a target tissue, each of the jaws comprising a longitudinal axis, the tissue-engaging surface of each jaw having a complementary self-aligning configuration with respect to the longitudinal axis of the other jaw;
a pinless rotation mechanism comprising rotatably cooperative features of the first jaw and the second jaw that connect the jaws together and enable the jaws to pivot between an open position and a closed position, the pinless rotation mechanism creating a common center of rotation; and
a biasing member attached to one of the proximal jaw piece and distal jaw piece, and bearing against the other of the proximal jaw piece and distal jaw piece, the biasing member exerting a biasing force that urges a distal end of the distal jaw piece toward the second jaw so as to maintain the distal jaw piece in a default biased position when the first and second jaws are in the open position,
wherein, when the jaws are moving from the open position toward the closed position, a first point of mutual contact between the jaws occurs at a distal end of each jaw due to the default biased position of the distal jaw piece, and
wherein the distal jaw piece of the first jaw is mounted at a substantially central point on a distal aspect of the proximal jaw piece of the first jaw such that, when the jaws are moving from the open position toward the closed position, a proximal end of the tissue-engaging surface of the first jaw moves away from the proximal jaw piece.

23. The electrosurgical device of claim 22, wherein the distal end of the proximal jaw piece comprises a tongue portion received in a recess in the distal jaw piece.

24. An electrosurgical device comprising:
a set of opposing jaws disposed distal to a shaft, the shaft comprising a central longitudinal axis, the jaws comprising a first jaw and a second jaw, the first jaw comprising a proximal jaw piece having a distal end and a distal jaw piece having a proximal end, the proximal end of the distal jaw piece received in the proximal jaw piece, and the distal end of the proximal jaw piece received in the distal jaw piece, wherein the jaw pieces of the first jaw are pivotably connected with each other, each jaw comprising a tissue-engaging surface with at least one bipolar electrode disposed thereon, wherein the distal jaw piece of the first jaw comprises the tissue-engaging surface of the first jaw, the jaws configured to deliver radiofrequency energy to a target tissue, each of the jaws comprising a longitudinal axis, the tissue-engaging surface of each jaw having a complementary self-aligning configuration with respect to the longitudinal axis of the other jaw;
a pinless rotation mechanism comprising rotatably cooperative features of the first jaw and the second jaw that connect the jaws together and enable the jaws to pivot between an open position and a closed position, the pinless rotation mechanism creating a common center of rotation; and
a biasing member attached to one of the proximal jaw piece and distal jaw piece, and bearing against the other of the proximal jaw piece and distal jaw piece, the biasing member exerting a biasing force that urges a distal end of the distal jaw piece toward the second jaw so as to maintain the distal jaw piece in a default biased position when the first and second jaws are in the open position,
wherein, when the jaws are moving from the open position toward the closed position, a first point of mutual contact between the jaws occurs at a distal end of each jaw due to the default biased position of the distal jaw piece, and
wherein the distal jaw piece of the first jaw is mounted at a pivot connection on a distal aspect of the proximal jaw piece of the first jaw such that, when the jaws are moving from the open position toward the closed position, a proximal end of the tissue-engaging surface of the first jaw rotates about the pivot connection toward the central longitudinal axis of the shaft.

25. The electrosurgical device of claim 24, wherein the distal end of the proximal jaw piece comprises a tongue portion received in a recess in the distal jaw piece.

* * * * *